United States Patent
Terasaka et al.

(10) Patent No.: US 7,064,144 B2
(45) Date of Patent: *Jun. 20, 2006

(54) IMIDAZOLE DERIVATIVES AS ADENOSINE DEAMINASE INHIBITORS

(75) Inventors: Tadashi Terasaka, Osaka (JP); Takeshi Kato, Osaka (JP); Kiyoshi Tsuji, Osaka (JP); Katsuya Nakamura, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/483,336

(22) PCT Filed: Jul. 10, 2002

(86) PCT No.: PCT/JP02/06983

§ 371 (c)(1), (2), (4) Date: Jun. 30, 2004

(87) PCT Pub. No.: WO03/006437

PCT Pub. Date: Jan. 23, 2003

(65) Prior Publication Data

US 2004/0236114 A1    Nov. 25, 2004

(30) Foreign Application Priority Data

Jul. 13, 2001    (AU) ..................... PR6363

(51) Int. Cl.
  *A01N 43/36*  (2006.01)
  *A61K 31/40*  (2006.01)
  *C07D 233/22* (2006.01)
  *C07D 233/64* (2006.01)

(52) U.S. Cl. .................. 514/423; 548/333.5
(58) Field of Classification Search .......... 514/400; 548/333.5, 337.1, 334.5
See application file for complete search history.

(56) References Cited

U.S. PATENT DOCUMENTS 6,359,145 B1 * 3/2002 Terasaka et al. ......... 548/333.5
6,596,738 B1 * 7/2003 Terasaka et al. ............ 514/337
2004/0097571 A1   5/2004 Tsuji et al.

FOREIGN PATENT DOCUMENTS

| WO | 00/05217 | 2/2000 |
|----|----------|--------|
| WO | 00/55155 | 9/2000 |
| WO | 01/26605 | 4/2001 |
| WO | 01/53271 | 7/2001 |

OTHER PUBLICATIONS

U.S. Appl. No. 10/169,757, filed Oct. 22, 2002, Tsuji, et al.
U.S. Appl. No. 10/483,336, filed Jan. 12, 2004, Terasaka, et al.
U.S. Appl. No. 10/503,585, filed Aug. 12, 2004, Tsuji, et al.
U.S. Appl. No. 10/483,336, filed Jun. 30, 2004, Terasaka, et al.

* cited by examiner

*Primary Examiner*—Kamal A. Saeed
*Assistant Examiner*—Susannah L. Chung
(74) *Attorney, Agent, or Firm*—Oblon, Spivak, McClelland, Maier & Neustadt, P.C.

(57) ABSTRACT

Imidazole compounds having adenosine deaminase inhibitory activity represented by the formula (I) wherein R1 is aryl or heterocyclic group which is optionally substituted with substituent(s); $R_2$ is lower alkyl; $R_3$ is hydroxy or protected hydroxy; -A- is lower alkylene; and —X— is —O— or —S—; provided that when then $R_1$ is aryl which is substituted with substituent(s), or heterocyclic group which is optionally substituted with substituent(s), its prodrug, or their salt. The compounds are useful for treating and/or preventing diseases for which adenosine is effective.

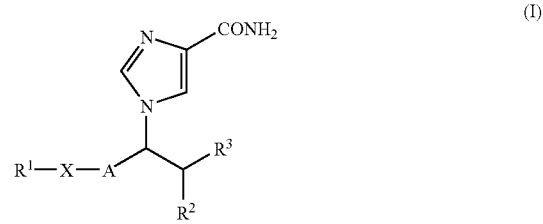

(I)

12 Claims, 13 Drawing Sheets

(1)

(2)

(3)

(4)

(5)

(6)

(7)

(8)

(9)

(10)

(11)

(12)

(13)

(14)

(15)

(16)

(17)

(18)

(19)

(20)

(21)

(22)

(23)

(24)

(25)

(26)

(27)

(28)

(29)

(30)

(31)

(32)

(33)

(34)

(35)

(36)

(37)

(38)

(39)

(40)

(41)

(42)

(43)

(44)

(45)

(46)

(47)

(48)

(49)

(50)

(51)

(52)

(53)

(54)

(55)

(56)

(57)

(58)

(59)

(60)

(61)

(62)

(63)

(64)

(65)

(66)

(67)

(68)

(69)

(70)

(71)

(72)

(73)

(74)

(75)

(76)

(77)

(78)

(79)

(80)

(81)

(82)

(83)

(84)

(85)

(86)

(87)

(88)

(89)

(90)

(91)

(92)

(93)

(94)

(95)

(96)

(97)

(98)

(99)

(100)

(101)

(102)

(103)

(104)

IMIDAZOLE DERIVATIVES AS ADENOSINE DEAMINASE INHIBITORS

TECHNICAL FIELD

This invention relates to novel imidazole compounds having pharmacological activity, to a process for their production and to a pharmaceutical composition containing the same.

BACKGROUND ART

Adenosine (Ado) is an endogenous purine nucleoside released by cells as part of the normal metabolic machinery. Ado has wide variety of biological activities, namely potent antiinflammatory and immunosuppressive properties, protective effects in cardiovascular and cerebrovascular ischemia, anticonvulsant effects and modulation effects of platelet aggregation, lipolysis, glycogenesis, blood flow and neurotransmission. Ado shows the biological activities by binding to its receptors anchored in the cell membrane. Therefore, it is the beneficial treatment for many diseases to perform the pharmacological elevation of extracellular Ado concentrations.

Adenosine deaminase (ADA) catalyzes an essentially irreversible deamination of adenosine and deoxyadenosine to inosine and deoxyinosine, respectively. In the last 10 years, ADA, which was considered to be cytosolic, has been found on the cell surface of many cells. Thus, blocking ADA activity with specific inhibitor is the potent way to elevate Ado concentrations in biological systems and the beneficial treatment for many diseases.

Some compounds have been known to have inhibitory activity of ADA (J. Med. Chem. 27, 274–278, 1984; ibid. 31, 390–393, 1988; ibid. 34, 1187–1192, 1991; ibid. 35, 4180–4184, 1992; ibid. 37, 305–308, 1994; ibid. 37, 3844–3849, 1994; WO98/02166).

Known imidazole compounds with pharmaceutical activity other than ADA inhibitory activity are described in U.S. Pat. No. 4,451,478 and WO97/26883.

Furthermore, some imidazole derivatives having ADA inhibitory activity have been reported, for example, as described in Drug Developement Research 28, 253–258, 1993.

DISCLOSURE OF THE INVENTION

This invention relates to novel imidazole compounds, which have pharmaceutical activity such as ADA inhibiting activity, to a process for their production, to a pharmaceutical composition containing the same, and to a use thereof.

One object of this invention is to provide the novel imidazole compounds, which have an ADA inhibiting activity.

Another object of this invention is to provide a process for production of the imidazole compounds.

A further object of this invention is to provide a pharmaceutical composition containing the imidazole compound as an active ingredient.

Still further object of this invention is to provide a use of the imidazole compound for manufacturing a medicament for treating or preventing various diseases, or a method of treating or preventing various diseases by administering the imidazole compound in an effective amount to elevate adenosine concentration.

The imidazole compound of this invention can be represented by the following formula (I):

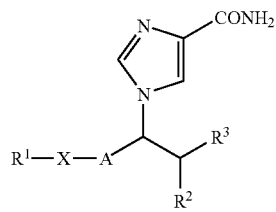

wherein $R^1$ is aryl or heterocyclic group which is optionally substituted with substituent(s);
$R^2$ is lower alkyl;
$R^3$ is hydroxy or protected hydroxy;
-A- is lower alkylene; and
—X— is —O— or —S—;
provided that when —X— is —O—, then $R^1$ is aryl which is substituted with substituent(s), or heterocyclic group which is optionally substituted with substituent(s), its prodrug, or their salt.

In the compound of formula (I), $R^1$ is preferably (1) aryl optionally substituted with substituent(s) selected from the group consisting of lower alkyl, halogen, optionally substituted aryl, optionally substituted heterocyclic group, lower alkoxy, and cyano, (2) condensed heterocyclic group optionally substituted with suitable substituent(s) selected from the group consisting of lower alkyl, optionally substituted aryl, and aryl(lower)alkyl, or (3) unsaturated heteromonocyclic group containing 1 to 4 nitrogen atoms which is optionally substituted with optionally substituted aryl. -A- is preferably methylene or ethylene. $R^2$ is preferably methyl.

The compound (I), its prodrug, or their salt can be prepared by the following processes. In the following formulae, compounds may be prodrugs or their salts.

Process 1

The compound (I) wherein —X— is —O—, and $R^3$ is not hydroxy can be obtained by reacting a compound of formula (II)

wherein $R^1$ is as defined above, with a compound of formula (III)

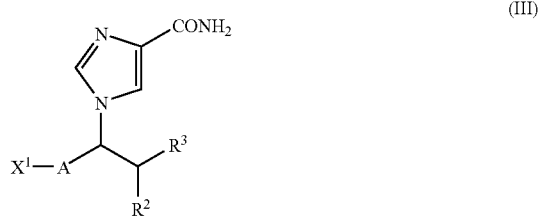

wherein $R^2$, $R^3$, and -A- are as defined above, and $X^1$ is hydroxy or a leaving group (such as halogen, alkanesulfonyloxy, arylsulfonyloxy, and the like), provided that $R^3$ is not hydroxy.

The reaction may be carried out in a manner such as the Mitsunobu reaction or the modification thereof. This reaction can be preferably carried out in the presence of di(lower)alkyl azodicarboxylate (e.g., diethyl azodicarboxylate, etc.) and trialkyl or triarylphosphines (e.g., triphenylphosphine, etc.) in a solvent, which does not adversely affect the reaction, such as tetrahydrofuran, diethyl ether, or the like. The reaction temperature is not critical and the reaction is usually carried out under cooling to warming.

Alternatively, in the case where $X^1$ is a leaving group, the compound (I) can also be produced by reacting the compound (III) with the compound (II) in the presence of a base such as sodium hydride, potassium tert-butoxide, or potassium carbonate in a solvent such as N,N-dimethylformamide (DMF) from room temperature to 100° C.

Process 2

The compound (I) wherein —X— is —O—, and $R^3$ is hydroxy can be obtained by reacting a compound of formula (I-1)

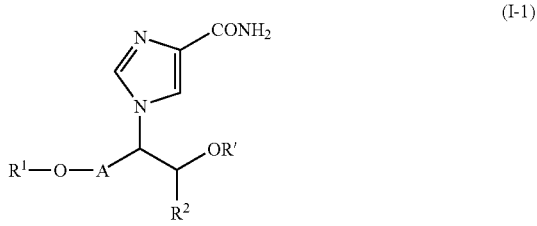

wherein $R^1$, $R^2$, and -A- are as defined above, and R' is hydroxy protective group, with a deprotecting agent.

The compound (I-1) can be reacted with a deprotecting agent such as palladium hydroxide on carbon/cyclohexene, trimethylsilyl iodide, or tetra-n-butylammonium fluoride in a solvent, which does not adversely affect the reaction, such as ethanol, chloroform, or tetrahydrofuran. The reaction temperature is not critical and the reaction is usually carried out under cooling to warming.

Process 3

The compound (I) can be obtained by reacting a compound of formula (IV)

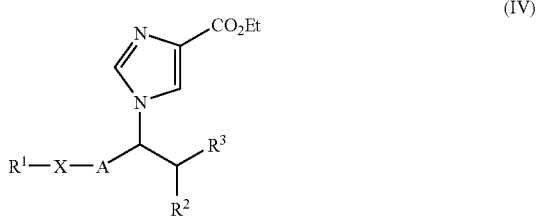

wherein $R^1$, $R^2$, $R^3$, -A-, and —X— are as defined above, with aqueous ammonia solution.

The reaction can be carried out in a solvent, which does not adversely affect the reaction, such as methanol, 1,2-dimethoxyethane, or the like from 50° C. to 120° C.

In the following, suitable examples of the definitions to be included within the scope of the invention are explained in detail.

The term "lower" means a group having 1 to 6 carbon atom(s), unless otherwise provided.

Suitable "lower alkyl" and lower alkyl moiety of "lower alkoxy", "halo(lower)alkyl," and "aryl(lower)alkyl" include a straight or branched one such as methyl, ethyl, propyl, isopropyl, butyl, isobutyl, tert-butyl, pentyl, hexyl, or the like, with methyl, ethyl, and tert-butyl being preferred.

Suitable "lower alkylene" may be straight or branched one having 1 to 8 carbon atom(s), such as methylene, ethylene, trimethylene, tetramethylene, pentametylene, hexamethylene, or the like, with methylene and ethylene being preferred.

Suitable "halogen" and halogen moiety of "halo(lower)alkyl" include fluorine, chlorine, bromine, or iodine.

Suitable "aryl" and aryl moiety of "aryl(lower)alkyl" include phenyl, naphthyl, tolyl, xylyl, fluorenyl, or the like, with phenyl, naphthyl, and fluorenyl being preferred.

Suitable "heterocyclic group" includes one containing at least one heteroatom selected from the group consisting of nitrogen, sulfur, and oxygen atoms, and include saturated or unsaturated, monocyclic or polycyclic heterocyclic group such as:

(1) unsaturated, 3 to 7-membered, preferably 5 or 6-membered heteromonocyclic group containing 1 to 4 nitrogen atoms, for example, pyrrolyl, pyrrolinyl, imidazolyl, pyrazolyl, pyridyl, pyrimidinyl, pyrazinyl, pyridazinyl, triazolyl [e.g., 4H-1,2,4-triazolyl, 1H-1,2,3-triazolyl, 2H-1,2,3-triazolyl, etc.], tetrazolyl [e.g., 1H-tetrazolyl, 2H-tetrazolyl, etc.], etc.;

(2) saturated, 3 to 7-membered, preferably 5 or 6-membered heteromonocyclic group containing 1 to 4 nitrogen atoms, for example, pyrrolidinyl, imidazolidinyl, piperidino, piperazinyl, etc.;

(3) unsaturated, condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl, etc.], etc.;

(4) unsaturated, 3 to 7-membered, preferably 5 or 6-membered heteromonocyclic group containing an oxygen atom, for example, pyranyl, furyl, etc.;

(5) unsaturated, 3 to 7-membered, preferably 5 or 6-membered heteromonocyclic group containing 1 to 2 sulfur atoms, for example, thienyl, etc.;

(6) unsaturated, 3 to 7-membered, preferably 5 or 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.], etc.;

(7) saturated, 3 to 7-membered, preferably 5 or 6-membered heteromonocyclic group containing 1 to 2 oxygen atoms and 1 to 3 nitrogen atoms, for example, morpholinyl, etc.;

(8) unsaturated, condensed heterocyclic group containing 1 to 2 oxygen atoms and 1 to 3 nitrogen atoms, for example, benzoxazolyl, benzoxadiazolyl, etc.;

(9) unsaturated, 3 to 7-membered, preferably 5 or 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.], etc.;

(10) saturated, 3 to 7-membered, preferably 5 or 6-membered heteromonocyclic group containing 1 to 2 sulfur atoms and 1 to 3 nitrogen atoms, for example, thiazolidinyl, etc.;

(11) unsaturated, condensed heterocyclic group containing 1 to 2 sulfur atoms and 1 to 3 nitrogen atoms, for example, benzothiazolyl, benzothiadiazolyl, etc.;

(12) unsaturated, condensed heterocyclic group containing 1 to 2 sulfur atoms or 1 to 2 oxygen atoms, for example, benzo[b]thiophenyl, benzofuranyl, dibenzofuranyl, etc.; or the like.

Among the above, more preferable "heterocyclic group" is above-mentioned (1), (3) (5), (6), (7), (8), (9), (11), and (12), in which the most preferable one is pyrrolyl (e.g., 1-pyrrolyl, etc.), pyridyl (e.g., 2-pyridyl, 3-pyridyl, etc.), indolyl (e.g., 1H-indol-5-yl, etc.), benzimidazolyl (e.g., 1H-benzimidazol-2-yl, etc.), quinolyl (e.g., 2-quinolyl, 6-quinolyl, etc.), isoquinolyl (e.g., 3-isoquinolyl, 7-isoquinolyl, etc.), thienyl (e.g., 2-thienyl, etc.), morpholinyl (e.g., 4-morpholinyl, etc.), benzoxazolyl (e.g., 2-benzoxazolyl, 6-benzoxazolyl, etc.), thiazolyl (e.g., 4-thiazolyl, etc.), benzothiazolyl (e.g., 5-benzothiazolyl, etc.), benzo[b]thiophenyl (e.g., 2-benzo[b]thiophenyl, etc.), benzofuranyl (e.g., 2-benzofuranyl, etc.), or dibenzofuranyl (e.g., 2-dibenzofuranyl, etc.).

Suitable "protected hydroxy" includes lower alkoxy optionally substituted with aryl (e.g., benzyloxy, etc.); acyloxy; or tri(lower)alkylsilyloxy (i.e., trimethylsilyloxy, tert-butyldimethylsilyloxy, etc.); or the like.

Suitable hydroxy protective groups in the protected hydroxy group include lower alkyl optionally substituted with aryl; acyl; tri(lower)alkylsilyl (i.e., trimethylsilyl, tert-butyldimethyl-silyl, etc.); or the like. Here, suitable "acyl" includes acetyl, trifluoroacetyl, or the like.

Suitable "leaving group" includes halogen, acyloxy (e.g., acetyloxy, trifluoroacetyloxy, etc.), lower alkylsulfonyloxy (e.g., methanesulfonyloxy, etc.), triarylphosphinoxy (e.g., —O—P$^+$(C$_6$H$_5$)$_3$, etc.), or the like.

Suitable substituent(s) of "optionally substituted aryl" and "optionally substituted heterocyclic group" include lower alkyl, halo(lower)alkyl, lower alkoxy, halogen, aryl, aryl(lower)alkyl, cyano, or the like.

The term "optionally substituted aryl" means aryl which is optionally substituted with one or more substituent(s) selected from the group consisting of lower alkyl, halo(lower)alkyl, lower alkoxy, halogen, cyano, and the like.

Examples of the "optionally substituted aryl" include unsubstituted aryl such as phenyl or the like; haloaryl such as 4-fluorophenyl, 2-chlorophenyl, 3-chlorophenyl, 4-chlorophenyl, 3,5-dichlorophenyl, or the like; lower alkylaryl such as 4-methylphenyl, or the like; lower alkoxyaryl such as 3-methoxyphenyl, 4-methoxyphenyl, or the like; halo(lower)alkylaryl such as 4-(trifluoromethyl)phenyl or the like; cyanoaryl such as 4-cyanophenyl, or the like; etc.

The term "optionally substituted heterocyclic group" means heterocyclic group which is optionally substituted with one or more substituent(s) selected from the group consisting of lower alkyl, lower alkoxy, halogen, aryl, aryl(lower)alkyl, and the like.

Examples of the "optionally substituted heterocyclic group" include unsubstituted heterocyclic group such as 1H-benzimidazol-2-yl, 2-thienyl, 4-morpholinyl, 2-benzoxazolyl, 1-benzothien-2-yl, 2-benzofuranyl, 1H-pyrrol-1-yl, or the like; heterocyclic group substituted with lower alkyl, such as 5-methyl-2-thienyl or the like; heterocyclic group substituted with lower alkoxy, such as 6-methoxy-3-pyridyl or the like; heterocyclic group substituted with halogen, such as 5-chloro-2-thienyl, 6-chloro-3-pyridyl, or the like; heterocyclic group substituted with aryl, such as 2-phenylthiazol-4-yl or the like; heterocyclic group substituted with aryl(lower)alkyl, such as 2-benzylthiazol-4-yl or the like.

Suitable salts of the compounds of the present invention are pharmaceutically acceptable conventional non-toxic salts and can be an organic acid addition salt (e.g., formate, acetate, trifluoroacetate, maleate, tartarate, oxalate, methanesulfonate, benzenesulfonate, toluenesulfonate, etc.), an inorganic acid addition salt (e.g., hydrochloride, hydrobromide, sulfate, phosphate, etc.), a salt with an amino acid (e.g., aspartic acid salt, glutamic acid salt, etc.), or the like.

The "prodrug" means the derivatives of compounds of the present invention having a chemically or metabolically degradable group, which becomes pharmaceutically active after biotransformation.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies.

The compound of the present invention can be purified by any conventional purification methods employed for purifying organic compounds, such as recrystallization, column chromatography, thin-layer chromatography, high-performance liquid chromatography, and the like. The compounds can be identified by conventional methods such as NMR spectrometry, mass spectrometry, IR spectrometry, elemental analysis, measurement of melting point, and the like.

The compound (I), its prodrug, or their salt can be administered alone or in the form of a mixture, preferably, with a pharmaceutical vehicle or carrier.

The active ingredient of this invention can be used in the form of a pharmaceutical preparation, for example, in solid, semisolid, or liquid form, which contains a compound (I), as an active ingredient, in admixture with an organic or inorganic carrier or excipient suitable for oral, external (topical), enteral, intravenous, intramuscular, parenteral, or intramucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops, and any other form suitable for use. The carriers which can be used are water, wax, glucose, lactose, gum acacia, gelatin, mannitol, starch paster, magnesium trisilicate, talc, corn starch, keratin, paraffin, colloidal silica, potato starch, urea, and other carriers suitable for use in manufacturing preparations, in solid, semisolid, or liquid form, and in addition, auxiliary, stabilizing, thickening, and coloring agents and perfumes may be used. The active compound is included in a pharmaceutical composition in an effective amount sufficient to produce the desired effect upon the process or condition of the diseases.

The active ingredient can be formulated into, for example, preparations for oral application, preparations for injection, preparations for external application, preparations for inhalation, preparations for application to mucous membranes, etc.

Mammals which may be treated by the present invention include livestock mammals such as cows, horses, etc., domestic animals such as dogs, cats, rats, etc., and humans, and preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

An ADA inhibitor, such as the compound (I) or its pharmaceutically acceptable salts of this invention, possesses ADA inhibiting activity and are thus useful in immunomodulation, especially immunosuppression, antiinflammation and treatment and prevention of various diseases for which Ado is effective. Examples of the diseases are as follows:

a) Autoimmune diseases and inflammatory conditions, e.g., various pains collagen diseases, autoimmune diseases, various immunity diseases, and the like in human beings or animals, and more particularly for the treating and/or preventing inflammation and pain in joint and muscle (e.g., rheumatoid arthritis, rheumatoid spondylitis, osteoarthritis, gouty arthritis, etc.), inflammatory skin condition (e.g., sunburn, eczema, etc.), inflammatory eye condition (e.g., conjunctivitis, etc.), lung disorder in which inflammation is involved (e.g., asthma, bronchitis, pigeon fancier's disease, farmer's lung, etc.), condition of the gastrointestinal tract associated with inflammation (e.g., aphthous ulcer, Crohn's disease, atrophic gastritis, ulcerative colitis, coeliac disease, regional ileitis, irritable bowel syndrome, etc.), gingivitis, (inflammation, pain and tumescence after operation or injury), pyrexia, pain and other conditions associated with inflammation, systemic lupus erythematosus, scleroderma, polymyositis, polychondritis, periarteritis nodosa, ankylosing spondylitis, inflammatory chronic renal condition (e.g., nephrotic syndrome, glomerulonephritis, membranous nephritis, etc.), acute nephritis, rheumatic fever, Sjogren's syndrome, Behcet disease, thyroiditis, type I diabetes, dermatomyositis, chronic active hepatitis, acute hepatitis, myasthenia gravis, idiopathic sprue, Grave's disease, multiple sclerosis, primary billiary cirrhoris, Reiter's syndrome, autoimmune hematological disorders (e.g., hemolytic anemia, pure red cell anemia, idiopathic thrombocytopenia; aplastic anemia, etc.), myasthenia gravis, uveitis, contact dermatitis, psoriasis, Kawasaki disease, sarcoidosis, Wegner's granulomatosis, Hodgkin's disease, or the like;

b) Organ or tissue allo- or xeno-transplant rejection, e.g., kidney, liver, heart, lung, combined heart-lung, bone marrow, islet cells, pancreatic, skin, chromaffin or dopamine producing cells, small bowel, or corneal transplantation. Treating and/or preventing graft-versus-host disease, such as occurs following bone marrow transplantation;

c) Chronic pain (e.g., cancer pain, diabetic neuropathy, etc);

d) Various leukemias, including virus induced or various induced lymphomas; and e) Diseases that arise from, or are aggravated by, insufficient blood flow through a particular organ or portion thereof, e.g., heart attacks or strokes, the microvascular disease of diabetes mellitus, atherosclerosis, or events resulting in a less prolonged loss of blood flow (e.g., angina pectoris, transient ischemic attacks, bowel ischemia, kidney ischemia, intermittant claudication of skeletal muscle, migraine headaches, Raynaud's phenomenon), or the like.

An ADA inhibitor, such as the compound (I) or its pharmaceutically acceptable salt of this invention, is useful for protection against the progression of glomerulosclerosis by suppressing glomerular hypertension and hyperfiltration, and thus useful for treatment and/or prevention of glomerulosclerosis.

An ADA inhibitor, such as the compound (I) or its pharmaceutically acceptable salt of this invention, is useful for complementing the defect of an IL-2 inhibitor, such as FK506, cyclosporin, or the like, in immunosuppresive effects. Thus, the combination use of the two compounds enables treatment and prevention of various diseases and conditions in need of immunosuppression.

Any patents, patent applications, and publications cited herein are incorporated by reference.

In order to illustrate the usefulness of the object compound (I), the pharmacological test data of the compound (I) are shown in the following.

Adenosine Deaminase (ADA) Enzyme Assay

Test Compound:
1-[(2S,3R)-5-(1,1'-biphenyl-3-yloxy)-2-hydroxy-3-pentyl]imidazole-4-carboxamide (Example 20)
1-{(2S,3R)-2-hydroxy-5-[3-(2-thienyl)phenoxy]-3-pentyl}imidazole-4-carboxamide (Example 32)
1-[(2S,3R)-2-hydroxy-5-(2-quinolyloxy)-3-pentyl]imidazole-4-carboxamide (Example 49)
1-[(2S,3R)-2-hydroxy-5-(2-naphthylthio)-3-pentyl]imidazole-4-carboxamide (Example 76)
1-[(2S,3R)-2-hydroxy-5-(2-quinolylthio)-3-pentyl]imidazole-4-carboxamide (Example 78)

Test Method:

The reaction velocity (V) is measured by a change in absorbance at 265 nm (A265) resulting from the deamination of adenosine. Human ADA was expressed and purified from ADA-deficient bacterial strain. Reaction mixtures of a total volume of 200 µl contained 0.16 µg/ml of ADA and 0.1 mM of adenosine and test compound in 10 mM phosphate buffer saline (pH 7.4). The reaction was started by addition of ADA to a mixture of adenosine and test compound. The reaction was followed at room temperature by recording decrease in A265 for 3 minutes in SPECTRAmax 250 (Molecular Devices, USA) to automatically calculate $V_{max}$. Inhibitory potency of test compound was expressed as $IC_{50}$ value, the drug concentration required to produce 50% inhibition of $V_{max}$ in comparison to vehicle treatment.

| Results: | |
|---|---|
| Test Compound | $IC_{50}$ (nM) |
| Example 20 | <20 |
| Example 32 | <20 |
| Example 49 | <20 |
| Example 76 | <20 |
| Example 78 | <20 |

BEST MODE FOR CARRYING OUT THE INVENTION

Figure 1:
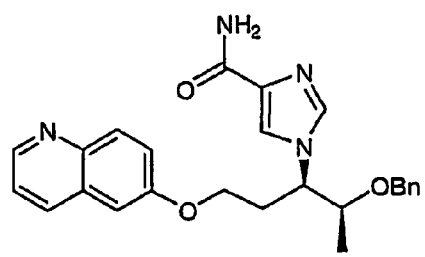
FIG. 1 shows chemical formulae of compound (1) to compound (8).
Figure 1:
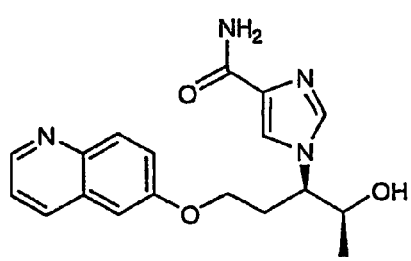
Figure 1:
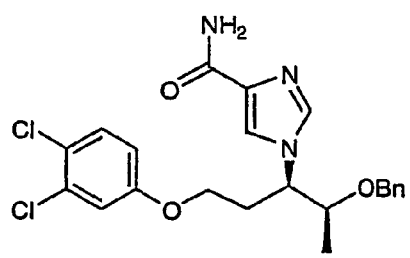
Figure 1:
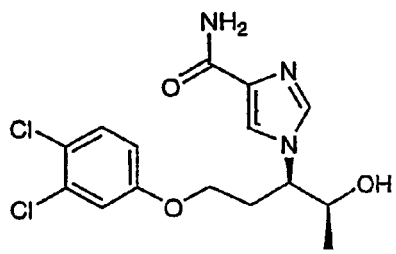
Figure 1:
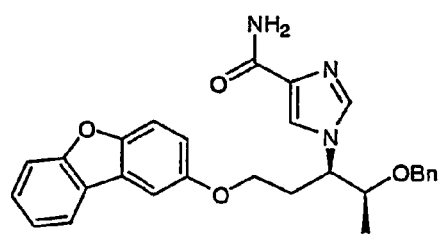
Figure 1:
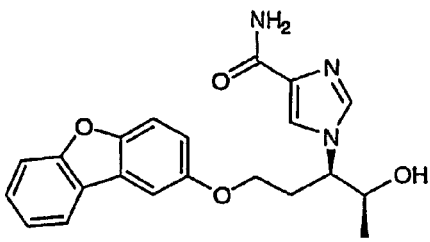
Figure 1:
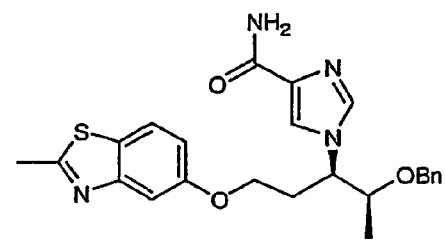
Figure 1:
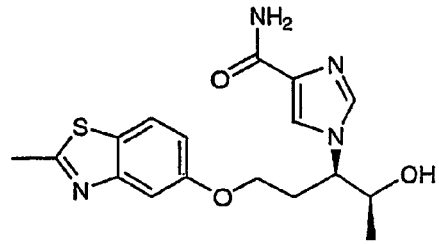
Figure 2:
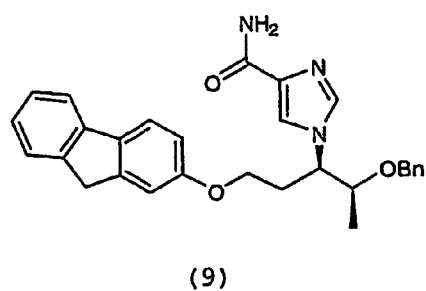
FIG. 2 shows chemical formulae of compound (9) to compound (16).
Figure 2:
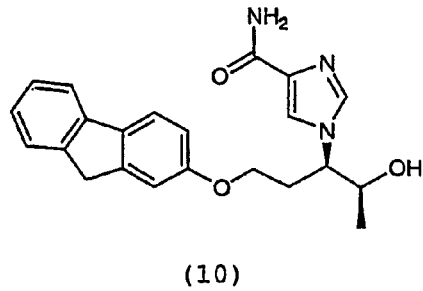
Figure 2:
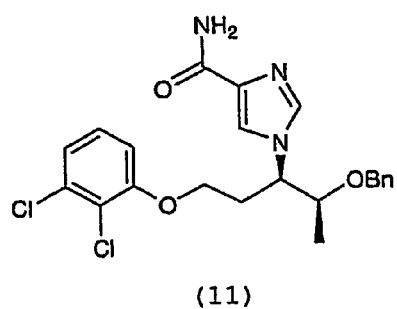
Figure 2:
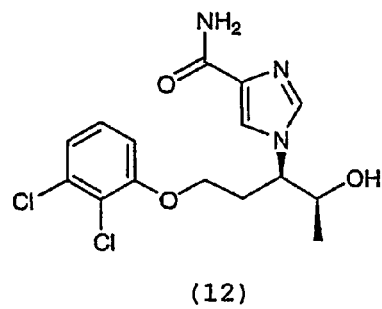
Figure 2:
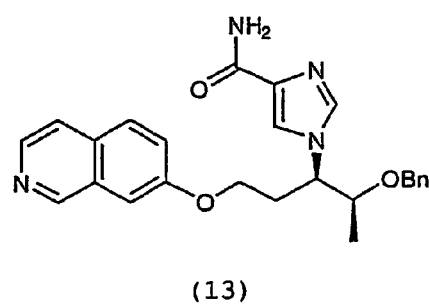
Figure 2:
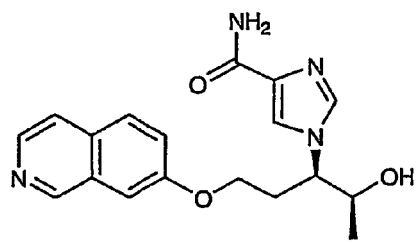
Figure 2:
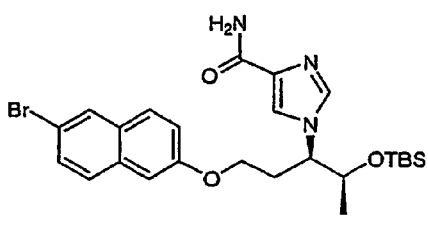
Figure 2:
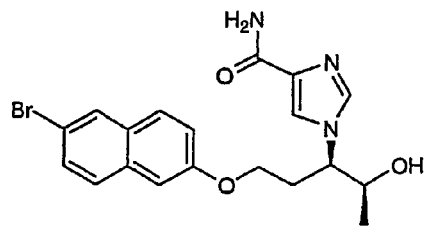
Figure 3:
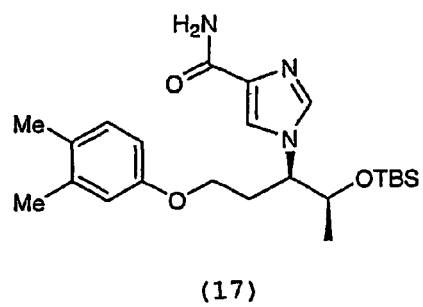
FIG. 3 shows chemical formulae of compound (17) to compound (24).
Figure 3:
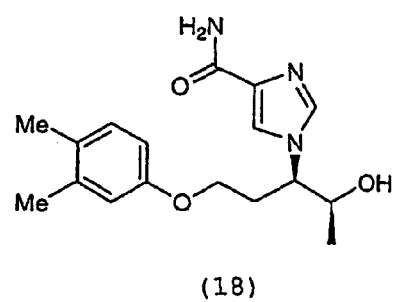
Figure 3:
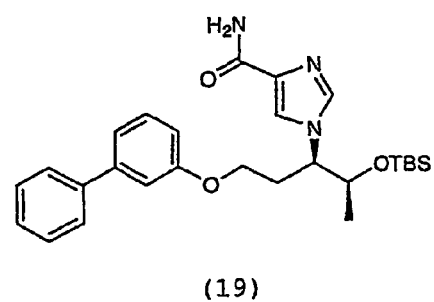
Figure 3:
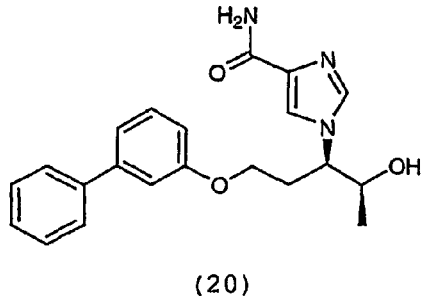
Figure 3:
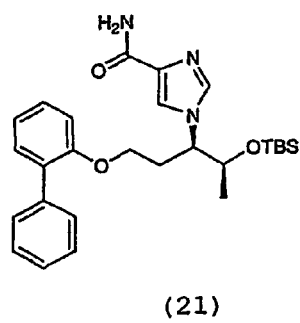
Figure 3:
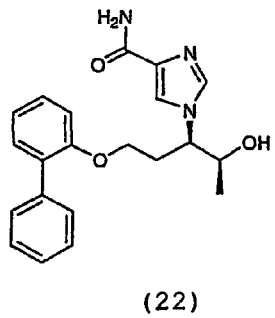
Figure 3:
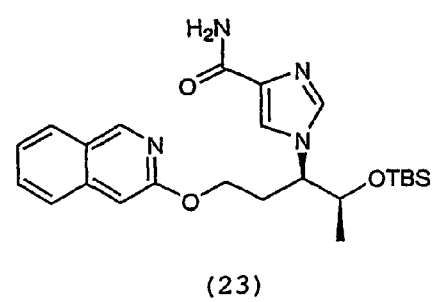
Figure 3:
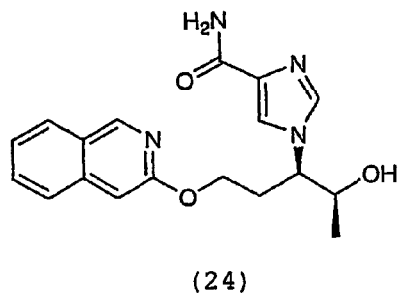
Figure 4:
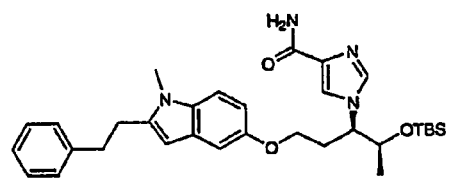
FIG. 4 shows chemical formulae of compound (25) to compound (32).
Figure 4:
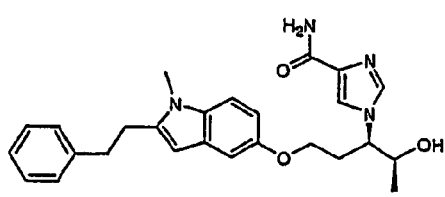
Figure 4:
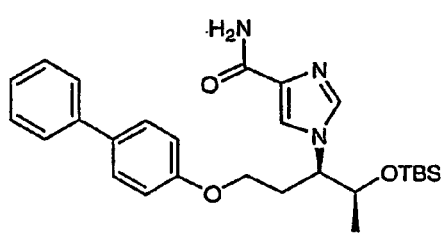
Figure 4:
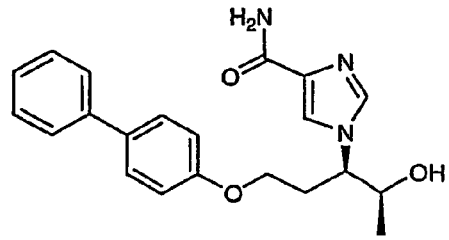
Figure 4:
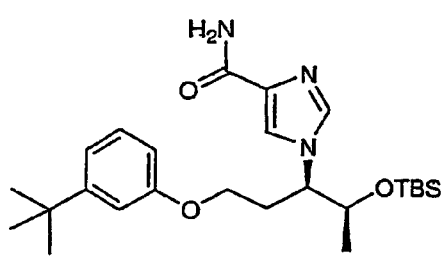
Figure 4:
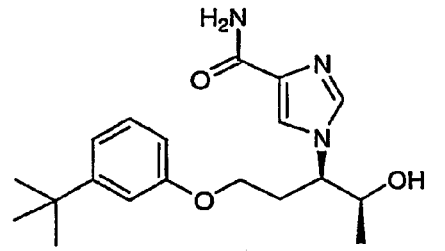
Figure 4:
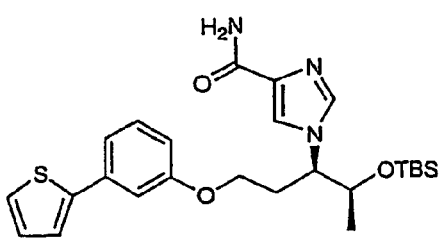
Figure 4:
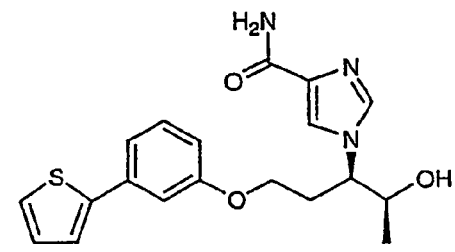
Figure 5:
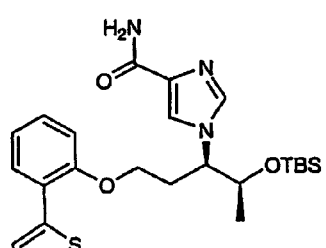
FIG. 5 shows chemical formulae of compound (33) to compound (40).
Figure 5:
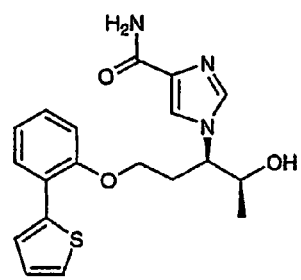
Figure 5:
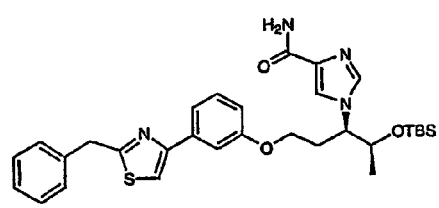
Figure 5:
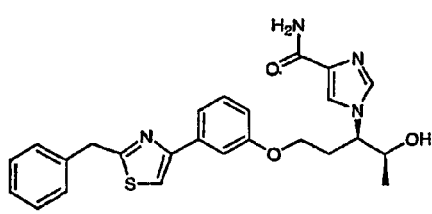
Figure 5:
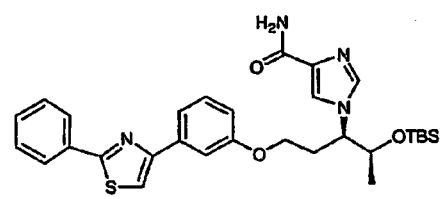
Figure 5:
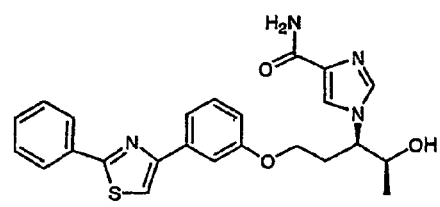
Figure 5:
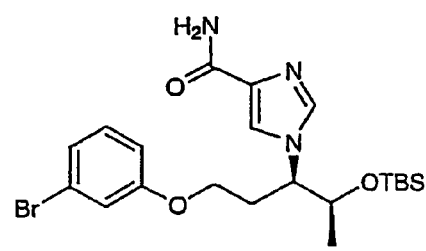
Figure 5:
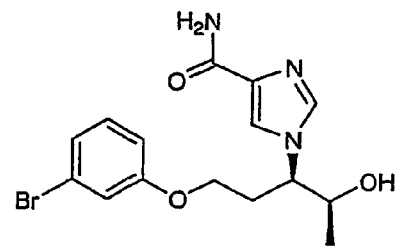
Figure 6:
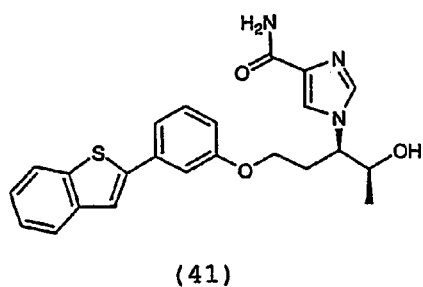
FIG. 6 shows chemical formulae of compound (41) to compound (48).
Figure 6:
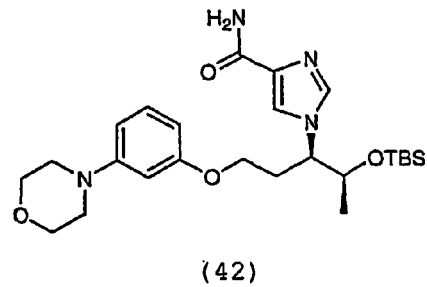
Figure 6:
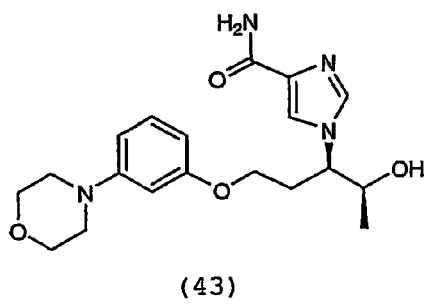
Figure 6:
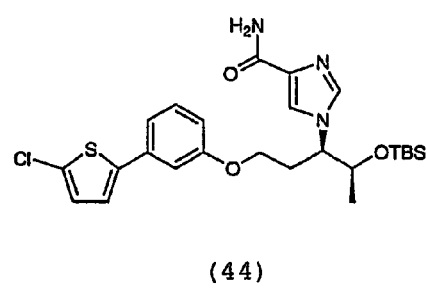
Figure 6:
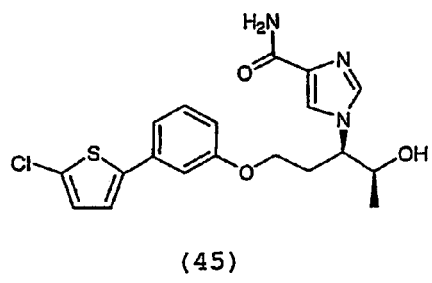
Figure 6:
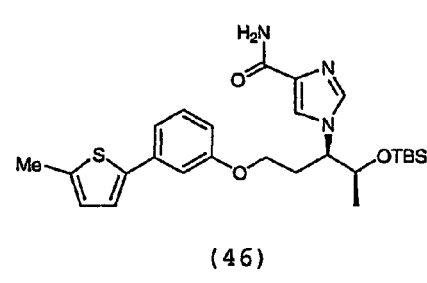
Figure 6:
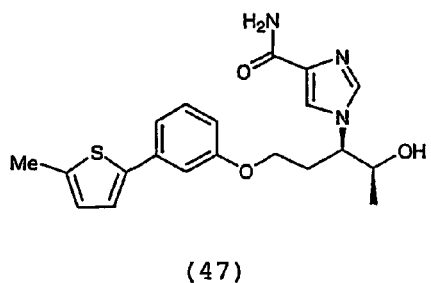
Figure 6:
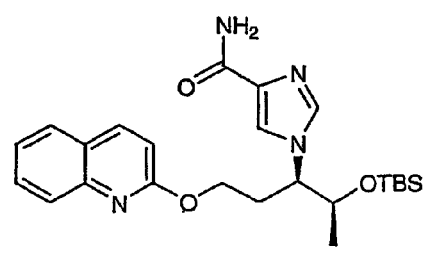
Figure 7:
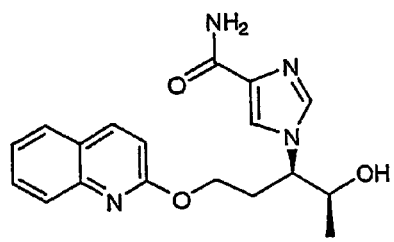
FIG. 7 shows chemical formulae of compound (49) to compound (56).
Figure 7:
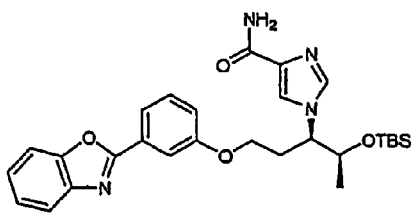
Figure 7:
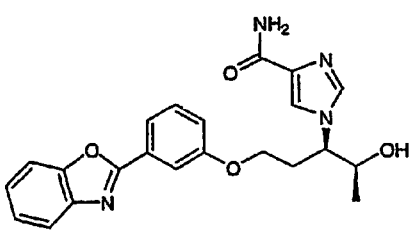
Figure 7:
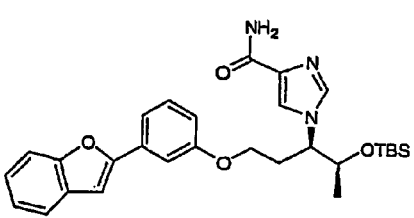
Figure 7:
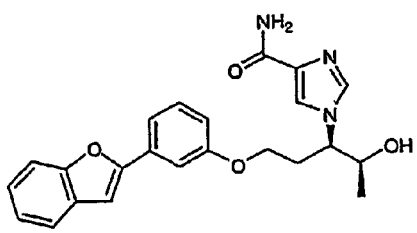
Figure 7:
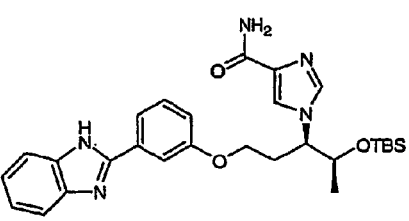
Figure 7:
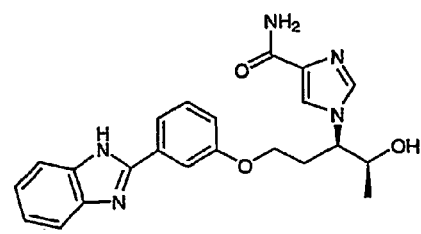
Figure 7:
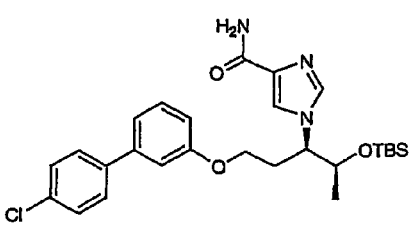
Figure 8:
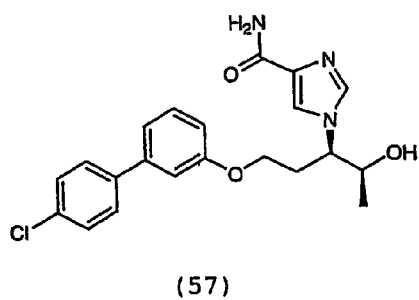
FIG. 8 shows chemical formulae of compound (57) to compound (64).
Figure 8:
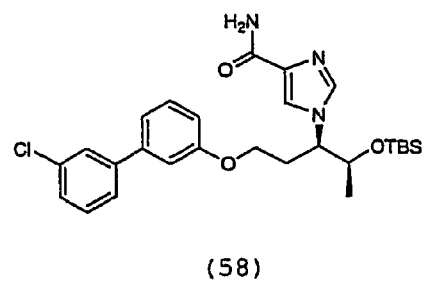
Figure 8:
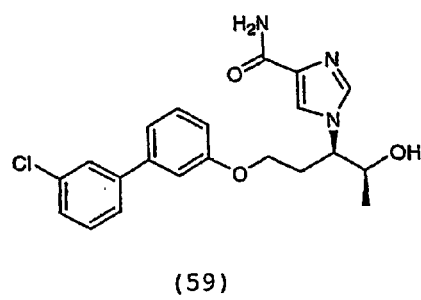
Figure 8:
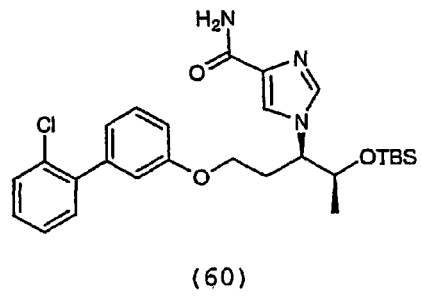
Figure 8:
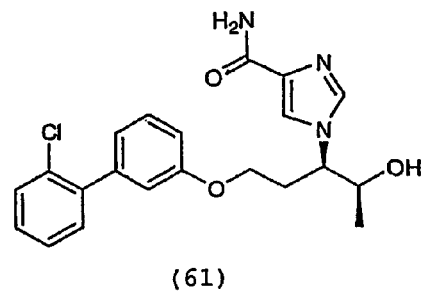
Figure 8:
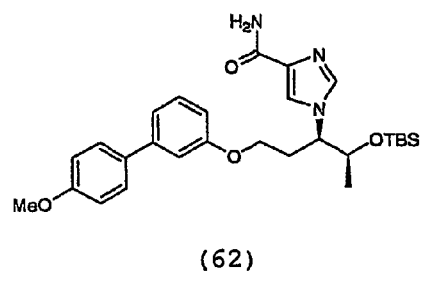
Figure 8:
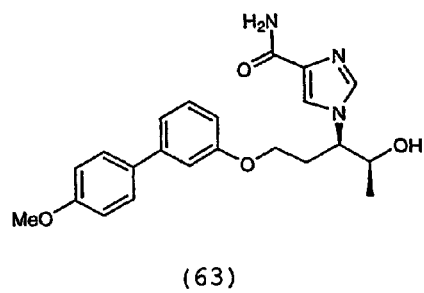
Figure 8:
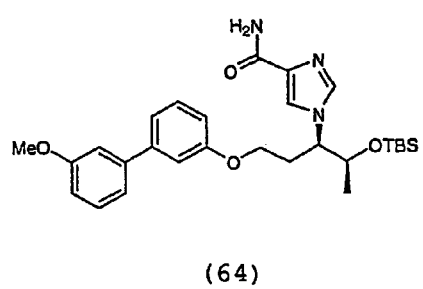
Figure 9:
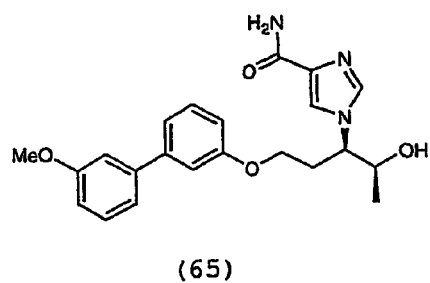
FIG. 9 shows chemical formulae of compound (65) to compound (72).
Figure 9:
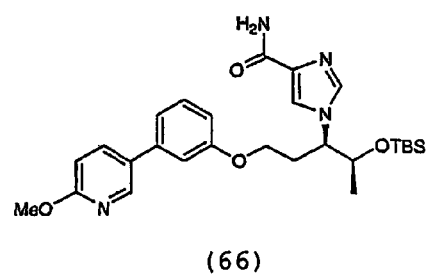
Figure 9:
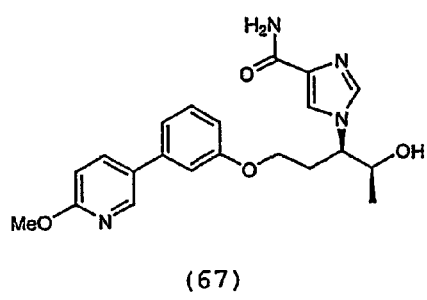
Figure 9:
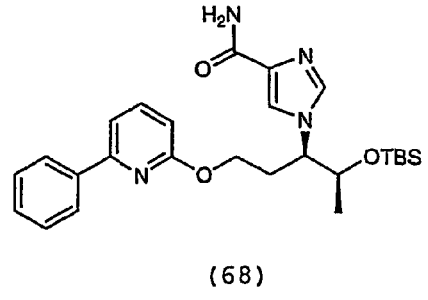
Figure 9:
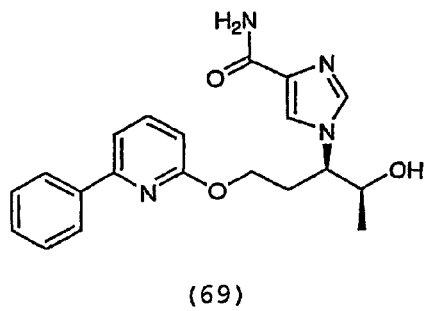
Figure 9:
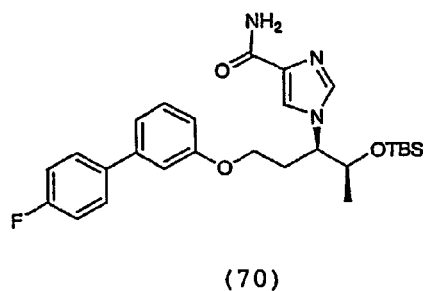
Figure 9:
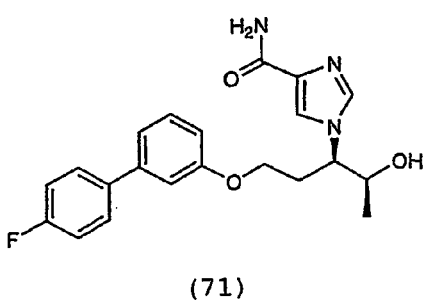
Figure 9:
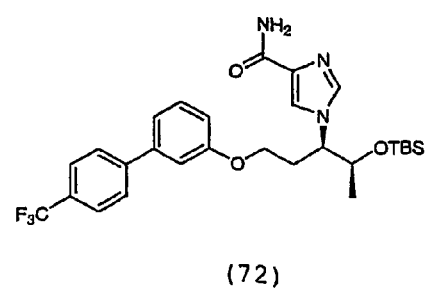
Figure 10:
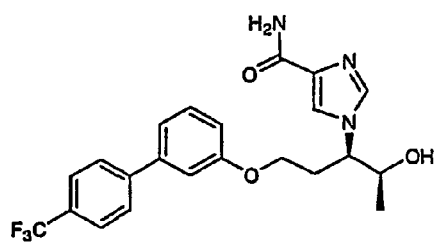
FIG. 10 shows chemical formulae of compound (73) to compound (80).
Figure 10:
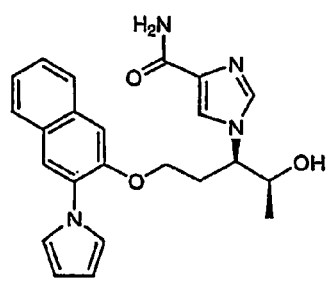
Figure 10:
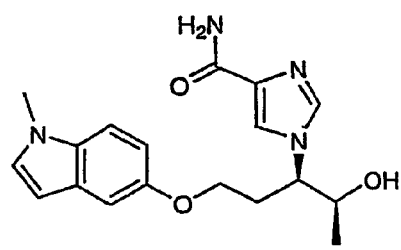
Figure 10:
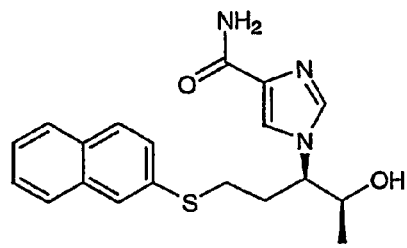
Figure 10:
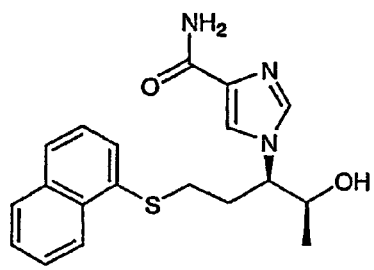
Figure 10:
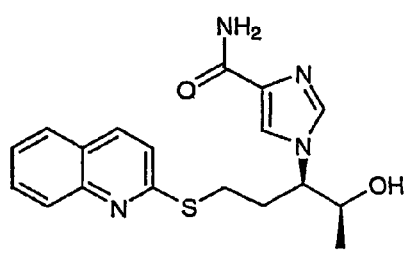
Figure 10:
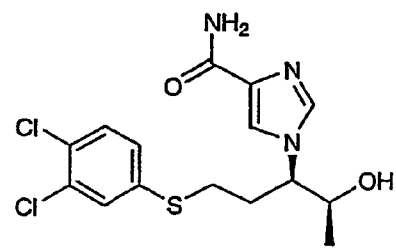
Figure 10:
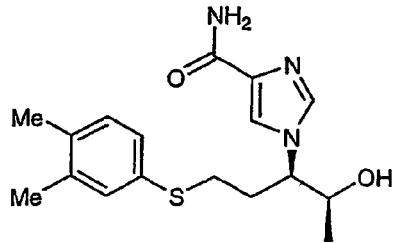
Figure 11:
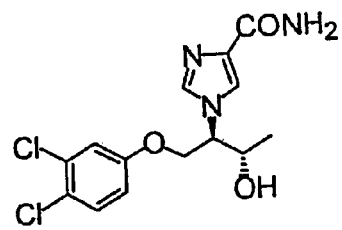
FIG. 11 shows chemical formulae of compound (81) to compound (88).
Figure 11:
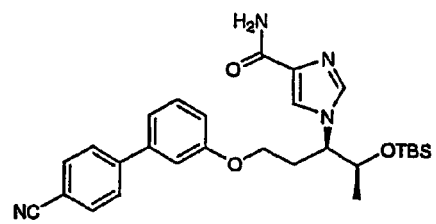
Figure 11:
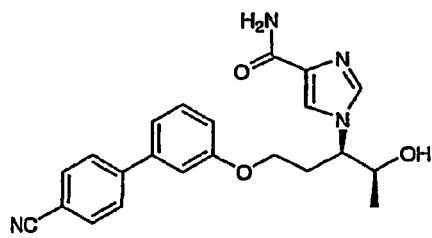
Figure 11:
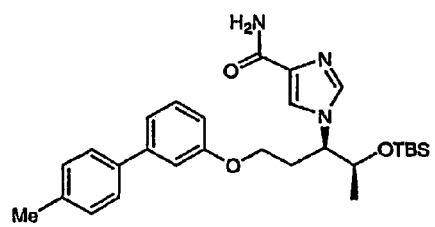
Figure 11:
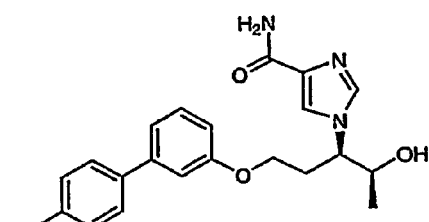
Figure 11:
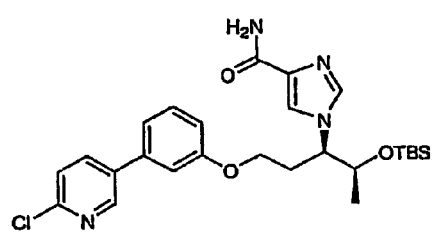
Figure 11:
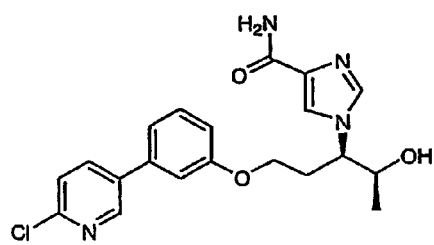
Figure 11:
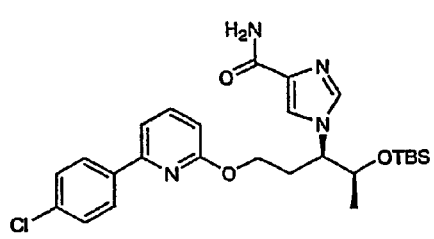
Figure 12:
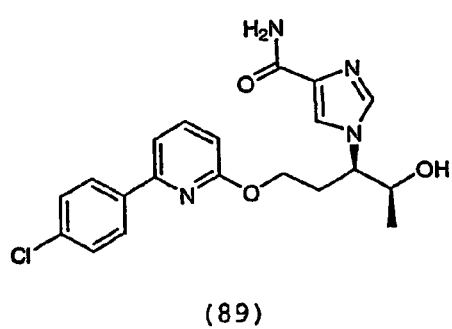
FIG. 12 shows chemical formulae of compound (89) to compound (96).
Figure 12:
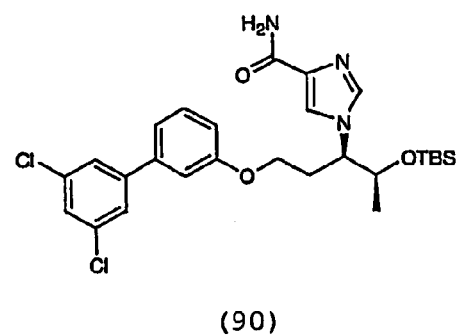
Figure 12:
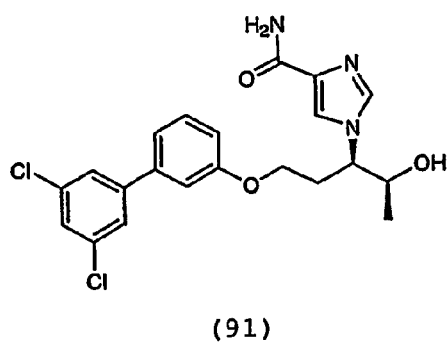
Figure 12:
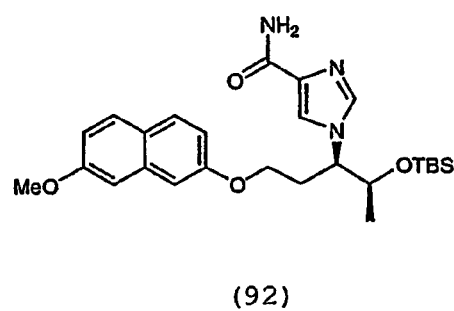
Figure 12:
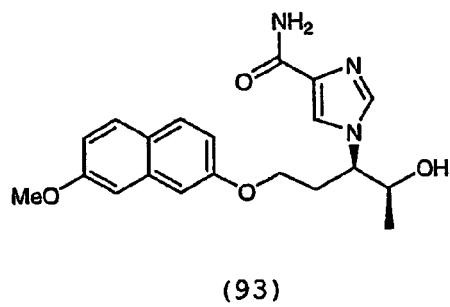
Figure 12:
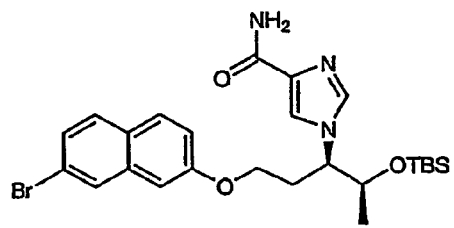
Figure 12:
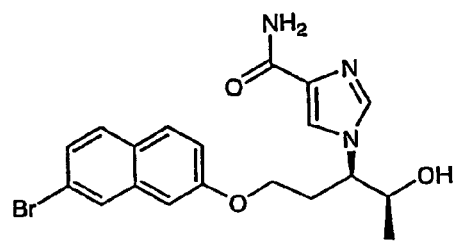
Figure 12:
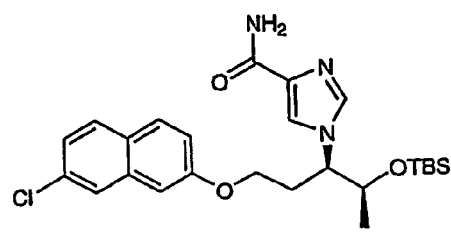
Figure 13:
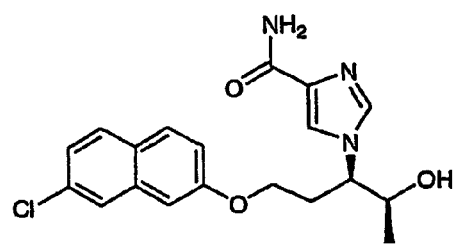
FIG. 13 shows chemical formulae of compound (97) to compound (104).
Figure 13:
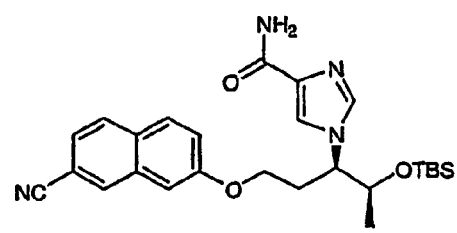
Figure 13:
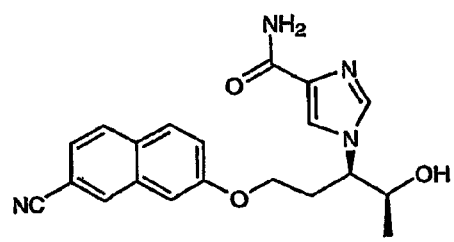
Figure 13:
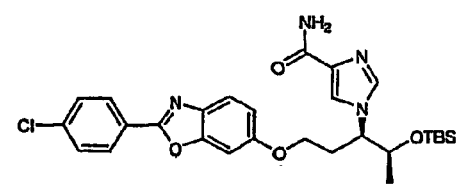
Figure 13:
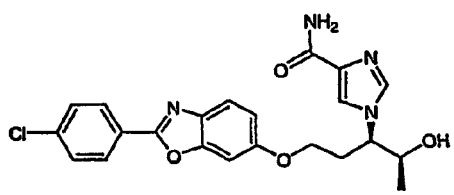
Figure 13:
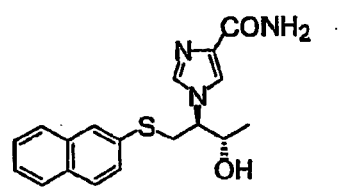
Figure 13:
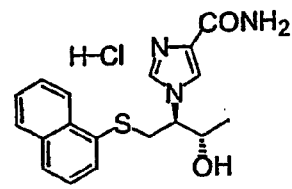
Figure 13:
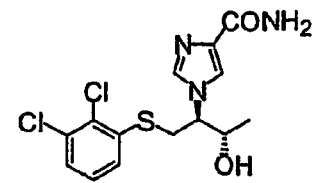

The following Preparation and Examples are given for the purpose of illustrating the present invention in detail, but are not to be construed to limit the scope of the present invention.

EXAMPLE 1

Under $N_2$, to a solution of 6-hydroxyquinoline (43 mg, 0.296 mmol) in DMF (3 ml) was added potassium carbonate (82 mg, 0.593 mmol) at room temperature. The reaction mixture was stirred for 30 minutes. 1-[(2S,3R)-2-benzyloxy-5-methanesulfonyloxy-3-pentyl]imidazole-4-carboxamide was added and the resulting mixture was stirred for 6 h at 70° C. The reaction mixture was poured into water (30 ml) and extracted with ethyl acetate. The organic layer was washed with brine, dried (sodium sulfate) and evaporated in vacuo. The residue was purified by silica gel (8 g) chromatography eluting with chloroform/methanol (100:1 to 30:1) to give 1-[(2S,3R)-2-benzyloxy-5-(6-quinolyloxy)-3-pentyl]imidazole-4-carboxamide (1) (62.5 mg, 48.9%).

IR (KBr, $cm^{-1}$): 3600–2800, 1664, 1597, 1230, 1110

NMR (CDCl$_3$, δ): 1.21 (3H, d, J=6 Hz), 2.15–2.75 (2H, m), 3.60–4.20 (3H, m), 4.30–4.50 (2H, m), 4.67 (1H, d, J=12 Hz), 5.36 (1H, brs), 6.91 (1H, d, J=3 Hz), 6.92 (1H, brs), 7.20–7.40 (7H, m), 7.46 (1H, s), 7.70 (1H, s), 7.99 (2H, d, J=9 Hz), 8.77 (1H, dd, J=4.2 Hz)

MS: 431 (M+H)$^+$ $[α]_D^{22.5}$=+63.50° (C=0.50, EtOH)

EXAMPLE 2

To a solution of 1-[(2S,3R)-2-benzyloxy-5-(6-quinolyloxy)-3-pentyl]imidazole-4-carboxamide (58 mg, 0.135 mmol) in cyclohexene (2.5 ml) and ethanol (5 ml) was added 20% palladium hydroxide on carbon (50 mg). The resulting mixture was stirred at reflux for 8 h. After cooling to room temperature, the mixture was filtered through Celite and washed with ethanol. The filtrate was concentrated in vacuo and then the residue was purified by silica gel (1.5 g) chromatography eluted with chloroform/methanol (50:1 to 10:1) to give 1-[(2S,3R)-2-hydroxy-5-(6-quinolyloxy)-3-pentyl]imidazole-4-carboxamide (2) (39.8 mg, 86.8%).

IR (KBr, $cm^{-1}$): 3700–2800, 1664, 1595, 1232, 1120

NMR (DMSO-d$_6$, δ): 0.94 (3H, d, J=6 Hz), 2.20–2.65 (2H, m), 3.65–4.40 (4H, m), 5.21 (1H, d, J=5 Hz), 7.03 (1H, brs), 7.15–7.55 (4H, m), 7.72 (1H, s), 7.78 (1H, s), 7.90 (1H, d, J=9 Hz), 8.19 (1H, d, J=8 Hz), 8.71 (1H, dd, J=4.2 Hz)

MS: 341 (M+H)$^+$

EXAMPLE 3

To a stirred mixture of 3,4-dichlorophenol (129 mg, 0.791 mmol), 1-[(2S,3R)-2-benzyloxy-5-hydroxy-3-pentyl]imidazole-4-carboxamide (80 mg, 0.264 mmol), and triphenylphosphine (90 mg, 0.343 mmol) in tetrahydrofuran (5 ml) was added dropwise diethyl azodicarboxylate (59.7 mg, 0.343 mmol) at ice-bath temperature. After the mixture was stirred for 2 h at room temperature, the solvent was removed in vacuo. The residue was purified by silica gel (10 g) chromatography eluting with chloroform/methanol (100:1 to 30:1) to give a mixture (120.6 mg, 102%) of 1-[(2S,3R)-2-benzyloxy-5-(3,4-dichlorophenoxy)-3-pentyl]imidazole-4-carboxamide (3) and by-products. This material was used without further purification.

IR (KBr, $cm^{-1}$): 3600–2800, 1664, 1593, 1232, 1124

NMR (CDCl$_3$, δ): 1.17 (3H, d, J=6 Hz), 2.05–2.70 (2H, m), 3.40–4.00 (3H, m), 4.29 (1H, m), 4.42 (1H, d, J=12 Hz), 4.65 (1H, d, J=12 Hz), 5.39 (1H, brs), 6.63 (1H, dd, J=9.3 Hz), 6.88 (1H, d, J=3 Hz), 6.92 (1H, brs), 7.10–7.50 (7H, m), 7.65 (1H, s)

MS: 448 (M+H)$^+$ ($^{35}$Cl×2), 450 (M+H)$^+$ ($^{35}$Cl–$^{37}$Cl), 452 (M+H)$^+$ ($^{37}$Cl×2)

EXAMPLE 4

To an ice cooled solution of 1-[(2S,3R)-2-benzyloxy-5-(3,4-dichlorophenyloxy)-3-pentyl]imidazole-4-carboxamide (59.5 mg, 0.133 mmol) in chloroform (5 ml) was added trimethylsilyl iodide (34.5 mg, 0.173 mmol). After 3 minutes, the ice bath was removed, and then stirred at room temperature overnight. The reaction was quenched by addition of methanol. This mixture was extracted with ethyl acetate, and the extracts were washed with brine, dried (sodium sulfate) and evaporated in vacuo. The residue was purified by silica gel (2.5 g) chromatography eluting with chloroform/methanol (50:1 to 10:1) to give 1-[(2S,3R)-5-(3,4-dichlorophenoxy)-2-hydroxy-3-pentyl]imidazole-4-carboxamide (4) (40.4 mg, 85.0%) as a white amorphous solid.

IR (KBr, $cm^{-1}$): 3600–2800, 1658, 1593, 1234, 1126

NMR (DMSO-d$_6$, δ): 0.91 (3H, d, J=6 Hz), 2.05–2.55 (2H, m), 3.50–4.25 (4H, m), 5.18 (1H, d, J=5 Hz), 6.88 (1H, dd, J=9.3 Hz), 7.02 (1H, brs), 7.15 (1H, d, J=3 Hz), 7.24 (1H, brs), 7.48 (1H, d, J=9 Hz), 7.69 (1H, s), 7.73 (1H, s)

MS: 358 (M+H)$^+$ ($^{35}$Cl×2), 360 (M+H)$^+$ ($^{35}$Cl–$^{37}$Cl), 362 (M+H)$^+$ ($^{37}$Cl×2)

EXAMPLE 5

This compound was prepared by a similar procedure to that of Example 3.

1-[(2S,3R)-2-benzyloxy-5-(2-dibenzofuranyloxy)-3-pentyl]imidazole-4-carboxamide (5).

NMR (CDCl$_3$, δ): 1.20 (3H, d, J=6 Hz), 2.10–2.70 (2H, m) 3.55–4.10 (3H, m), 4.30–4.50 (2H, m), 4.66 (1H, d, J=12 Hz), 5.36 (1H, brs), 6.93 (1H, brs), 6.94 (1H, dd, J=9.3 Hz), 7.15–7.60 (11H, m), 7.71 (1H, s), 7.83 (2H, d, J=8 Hz)

MS: 470 (M+H)+

EXAMPLE 6

This compound was prepared by a similar procedure to that of Example 2.
1-[(2S,3R)-5-(2-dibenzofuranyloxy)-2-hydroxy-3-pentyl]imidazole-4-carboxamide (6).

IR (KBr, cm$^{-1}$): 3600–2800, 1658, 1593, 1234, 1174

NMR (DMSO-d$_6$, δ): 1.00 (3H, d, J=6 Hz), 2.20–2.65 (2H, m) 3.60–4.50 (4H, m), 5.30 (1H, br), 7.01 (1H, dd, J=9.3 Hz), 7.25–7.80 (7H, m), 8.00 (1H, s), 8.09 (1H, d, J=8 Hz), 8.31 (1H, brs)

MS: 380 (M+H)$^+$

EXAMPLE 7

This compound was prepared by a similar procedure to that of Example 3.
1-[(2S,3R)-2-benzyloxy-5-(2-methyl-5-benzothiazolyloxy)-3-pentyl]imidazole-4-carboxamide (7).

NMR (CDCl$_3$, δ): 1.18 (3H, d, J=6 Hz), 2.10–2.75 (2H, m), 2.80 (3H, s), 3.55–4.10 (3H, m), 4.30–4.50 (2H, m), 4.65 (1H, d, J=12 Hz), 5.34 (1H, brs), 6.88 (1H, dd, J=9.2 Hz), 6.91 (1H, brs), 7.10–7.40 (6H, m), 7.45 (1H, s), 7.64 (1H, d, J=9 Hz), 7.67 (1H, s)

MS: 448 (M+H)$^+$ ($^{35}$Cl×2), 450 (M+H)$^+$ ($^{35}$Cl–$^{37}$Cl), 452 (M+H)$^+$ ($^{37}$Cl×2)

EXAMPLE 8

This compound was prepared by a similar procedure to that of Example 2.
1-[(2S,3R)-2-hydroxy-5-(2-methyl-5-benzothiazolyloxy)-3-pentyl]imidazole-4-carboxamide (8).

IR (KBr, cm$^{-1}$): 3700–2800, 1658, 1604, 1454, 1323, 1167, 1082, 1022

NMR (DMSO-d$_6$, δ): 0.93 (3H, d, J=6 Hz), 2.10–2.60 (2H, m), 2.75 (3H, s), 3.55–4.30 (4H, m), 5.18 (1H, d, J=5 Hz) 6.96 (1H, dd, J=9.2 Hz), 7.02 (1H, brs), 7.24 (1H, brs), 7.36 (1H, d, J=2 Hz), 7.70 (1H, s), 7.75 (1H, s), 7.85 (1H, d, J=9 Hz)

MS: 383 (M–H)$^-$, 385 (M+H)$^+$

EXAMPLE 9

This compound was prepared by a similar procedure to that of Example 3.
1-[(2S,3R)-2-benzyloxy-5-(2-fluorenyloxy)-3-pentyl]imidazole-4-carboxamide (9).

IR (KBr, cm$^{-1}$): 3600–2800, 1664, 1604, 1259, 1107

NMR (CDCl$_3$, δ): 1.19 (3H, d, J=6 Hz), 2.05–2.70 (2H, m), 3.50–4.10 (5H, m), 4.30–4.50 (2H, m), 4.65 (1H, d, J=12 Hz), 5.36 (1H, brs), 6.82 (1H, dd, J=8.2 Hz), 6.95 (1H, brs), 6.97 (1H, d, J=2 Hz), 7.18–7.78 (12H, m)

MS: 468 (M+H)$^+$

[α]$_D$$^{22.8}$=+87.30° (C=0.50, EtOH)

EXAMPLE 10

This compound was prepared by a similar procedure to that of Example 2.
1-[(2S,3R)-5-(2-fluorenyloxy)-2-hydroxy-3-pentyl]imidazole-4-carboxamide (10).

IR (KBr, cm$^{-1}$): 3600–2800, 1657, 1583, 1263, 1109

NMR (DMSO-d$_6$, δ): 0.94 (3H, d, J=6 Hz), 2.10–2.60 (2H, m), 3.55–4.30 (6H, m), 5.19 (1H, d, J=4 Hz), 6.88 (1H, dd, J=8.2 Hz), 7.02 (1H, brs), 7.09 (1H, d, J=2 Hz) 7.10–7.40 (3H, m), 7.51 (1H, d, J=8 Hz), 7.60–7.80 (4H, m)

MS: 378 (M+H)$^+$

EXAMPLE 11

This compound was prepared by a similar procedure to that of Example 3.
1-[(2S,3R)-2-benzyloxy-5-(2,3-dichlorophenoxy)-3-pentyl]imidazole-4-carboxamide (11).

IR (KBr, cm$^{-1}$): 3600–2800, 1672, 1265, 1090, 1057

NMR (CDCl$_3$, δ): 1.21 (3H, d, J=6 Hz), 2.05–2.75 (2H, m) 3.40–4.20 (3H, m), 4.40–4.60 (2H, m), 4.65 (1H, d, J=12 Hz), 5.35 (1H, brs), 6.65 (1H, dd, J=6.4 Hz), 6.91 (1H, brs), 7.00–7.40 (7H, m), 7.46 (1H, s), 7.68 (1H, s)

MS: 448 (M+H)$^+$ ($^{35}$Cl×2)

[α]D$^{22.8}$=+100.90° (C=0.50, EtOH)

EXAMPLE 12

This compound was prepared by a similar procedure to that of Example 4.
1-[(2S,3R)-5-(2,3-dichlorophenoxy)-2-hydroxy-3-pentyl]imidazole-4-carboxamide (12).

IR (KBr, cm$^{-1}$): 3600–2800, 1658, 1585, 1450, 1267, 1057, 1028

NMR (DMSO-d$_6$, δ): 0.93 (3H, d, J=6 Hz), 2.10–2.65 (2H, m) 3.60–4.30 (4H, m), 5.20 (1H, d, J=5 Hz), 6.90–7.40 (5H, m), 7.66 (1H, s), 7.73 (1H, s)

MS: 358 (M+H)$^+$ ($^{35}$Cl×2), 360 (M+H)$^+$ ($^{35}$Cl–$^{37}$Cl)

EXAMPLE 13

This compound was prepared by a similar procedure to that of Example 3.
1-[(2S,3R)-2-benzyloxy-5-(7-isoquinolyloxy)-3-pentyl]imidazole-4-carboxamide (13).

IR (KBr, cm$^{-1}$): 3600–2800, 1662, 1590, 1207

NMR (CDCl$_3$, δ): 1.20 (3H, d, J=6 Hz), 2.15–2.75 (2H, m), 3.65–4.50 (5H, m), 4.67 (1H, d, J=12 Hz), 5.37 (1H, brs), 6.92 (1H, brs), 7.06 (1H, d, J=2 Hz), 7.20–7.45 (6H, m), 7.47 (1H, s), 7.57 (1H, d, J=6 Hz), 7.60 (1H, s), 7.72 (1H, d, J=9 Hz), 9.09 (1H, s)

MS: 431 (M+H)$^+$

EXAMPLE 14

This compound was prepared by a similar procedure to that of Example 2.
1-[(2S,3R)-2-hydroxy-5-(7-isoquinolyloxy)-3-pentyl]imidazole-4-carboxamide (14).

IR (KBr, cm$^{-1}$): 3600–2800, 1658, 1593, 1267, 1207, 1142, 1092

NMR (DMSO-d$_6$, δ): 0.95 (3H, d, J=6 Hz), 2.20–2.65 (2H, m), 3.70–4.40 (4H, m), 5.22 (1H, brs), 7.07 (1H, brs), 7.20–7.50 (3H, m), 7.70–7.85 (3H, m), 7.90 (1H, d, J=9 Hz), 8.37 (1H, d, J=6 Hz), 9.18 (1H, s)

MS: 341 (M+H)$^+$

Preparation 1

To a solution of ethyl 1-[(2S,3R)-2-(tert-butyldimethylsilyloxy)-5-hydroxy-3-pentyl]imidazole-4-carboxylate (1.0 g, 2.8 mmol) in methanol (15 ml) was added aqueous 28% NH$_3$ solution (15 ml). And the mixture was heated at 100° C. in a sealed steel tube for 15 h. After cooling, the reaction mixture was concentrated in vacuo. The residue was purified by silica gel (35 g) chromatography eluting with chloroform/methanol (25:1 to 15:1) to give 1-[(2S,3R)-2-(tert-butyldimethylsilyloxy)-5-hydroxy-3-pentyl]imidazole-4-carboxamide (769.5 mg, 83.8%) as a white amorphous solid.

IR (KBr, cm$^{-1}$): 3600–2800, 1664, 1604, 1417, 1261, 1143, 1092, 1058

NMR (DMSO-d$_6$, δ) 0.00 (3H, s), 0.03 (3H, s), 0.86 (9H, s), 0.93 (3H, d, J=6 Hz), 1.80–2.15 (2H, m), 2.95–3.45 (2H, m), 3.90–4.25 (2H, m), 4.55 (1H, t, J=5 Hz), 7.02 (1H, brs), 7.25 (1H, brs), 7.64 (1H, s), 7.67 (1H, s)

MS: 327 (M–H)$^-$

EXAMPLE 15

This compound was prepared by a similar procedure to that of Example 3.

1-[(2S,3R)-5-(6-bromo-2-naphthyloxy)-2-(tert-butyldimethylsilyloxy)-3-pentyl]imidazole-4-carboxamide (15).

NMR (CDCl$_3$, δ): 0.05 (3H, s), 0.08 (3H, s), 0.93 (9H, s), 1.11 (3H, d, J=6 Hz), 2.10–2.70 (2H, m), 3.65–4.35 (4H, m), 5.35 (1H, brs), 6.90 (1H, brs), 6.95 (1H, d, J=2 Hz), 7.09 (1H, dd, J=9.2 Hz), 7.35–7.80 (5H, m), 7.90 (1H, s)

MS: 532 (M+H)$^+$ ($^{79}$Br), 534 (M+H)$^+$ ($^{81}$Br)

EXAMPLE 16

To an ice cooled solution of 1-[(2S,3R)-5-(6-bromo-2-naphthyloxy)-2-(tert-butyldimethylsilyloxy)-3-pentyl]imidazole-4-carboxamide (120 mg, 0.225 mmol) in THF (5 ml) was added dropwise 1.0 M tetra-n-butylammonium fluoride in THF (338 μl). After the addition was completed, the reaction mixture was stirred at ice-bath temperature for 2 hours. The reaction was quenched by addition of 25% aqueous AcONH$_4$ (5 ml) and H$_2$O (10 ml) The resulting mixture was stirred for several minutes and then extracted with ethyl acetate (30 ml). The organic layer was washed with brine, dried (sodium sulfate) and concentrated under reduced pressure. The residue was purified by silica gel (4 g) column chromatography eluting with chloroform/methanol (100:1 to 20:1) to give 1-[(2S,3R)-5-(6-bromo-2-naphthyloxy)-2-hydroxy-3-pentyl]imidazole-4-carboxamide (16) (58.6 mg, 62.2%) as a white solid.

IR (KBr, cm$^{-1}$): 3600–2800, 1655, 1593, 1498, 1261, 1207, 1126, 1086

NMR (DMSO-d$_6$, δ): 0.94 (3H, d, J=6 Hz), 2.10–2.65 (2H, m), 3.60–4.35 (4H, m), 5.20 (1H, d, J=5 Hz), 7.02 (1H, brs), 7.10–7.35 (3H, m), 7.54 (1H, dd, J=9.2 Hz), 7.60–7.90 (4H, m), 8.09 (1H, d, J=2 Hz)

MS: 418 (M+H)$^+$ ($^{79}$Br), 420 (M+H)$^+$ ($^{81}$Br)

EXAMPLE 17

This compound was prepared by a similar procedure to that of Example 15.

1-[(2S,3R)-2-(tert-butyldimethylsilyloxy)-5-(3,4-dimethylphenoxy)-3-pentyl]imidazole-4-carboxamide (17).

NMR (CDCl$_3$, δ): 0.02 (3H, s), 0.06 (3H, s), 0.90 (9H, s), 1.09 (3H, d, J=6 Hz), 2.00–2.60 (8H, m), 3.40–4.30 (4H, m), 5.32 (1H, brs), 6.53 (1H, dd, J=8.3 Hz), 6.60 (1H, d, J=3 Hz), 6.93 (1H, brs), 6.98 (1H, d, J=8 Hz), 7.41 (1H, s), 7.62 (1H, s)

MS: 432 (M+H)$^+$

EXAMPLE 18

This compound was prepared by a similar procedure to that of Example 16.

1-[(2S,3R)-5-(3,4-dimethylphenoxy)-2-hydroxy-3-pentyl]imidazole-4-carboxamide (18).

IR (KBr, cm$^{-1}$): 3600–2800, 1660, 1599, 1500, 1412, 1248, 1119, 1090, 1053

NMR (DMSO-d$_6$, δ): 0.92 (3H, d, J=6 Hz), 2.00–2.55 (8H, m), 3.40–4.30 (4H, m), 5.16 (1H, d, J=5 Hz), 6.55 (1H, dd, J=8, 2.5 Hz), 6.64 (1H, d, J=2.5 Hz), 6.97 (1H, d, J=8 Hz), 7.02 (1H, brs), 7.24 (1H, brs), 7.67 (1H, s) 7.71 (1H, s)

MS: 318 (M+H)$^+$

EXAMPLE 19

This compound was prepared by a similar procedure to that of Example 15.

1-[(2S,3R)-5-(1,1'-biphenyl-3-yloxy)-2-(tert-butyldimethylsilyloxy)-3-pentyl]imidazole-4-carboxamide (19).

NMR (CDCl$_3$, δ): 0.03 (3H, s), 0.06 (3H, s), 0.91 (9H, s), 1.11 (3H, d, J=6 Hz), 2.00–2.65 (2H, m), 3.55–4.35 (4H, m), 5.36 (1H, brs), 6.70–7.05 (3H, m), 7.10–7.75 (9H, m)

MS: 480 (M+H)$^+$

EXAMPLE 20

This compound was prepared by a similar procedure to that of Example 16.

1-[(2S,3R)-5-(1,1'-biphenyl-3-yloxy)-2-hydroxy-3-pentyl]imidazole-4-carboxamide (20).

IR (KBr, cm$^{-1}$): 3600–2800, 1658, 1595, 1473, 1415, 1238 1088

NMR (DMSO-d$_6$, δ): 0.93 (3H, d, J=6 Hz), 2.10–2.60 (2H, m), 3.60–4.35 (4H, m), 5.18 (1H, d, J=5 Hz), 6.75–750 (9H, m), 7.55–7.85 (4H, m)

MS: 366 (M+H)$^+$

EXAMPLE 21

This compound was prepared by a similar procedure to that of Example 15.

1-[(2S,3R)-5-(1,1'-biphenyl-2-yloxy)-2-(tert-butyldimethylsilyloxy)-3-pentyl]imidazole-4-carboxamide (21).

NMR (CDCl$_3$, δ): –0.06 (3H, s), 0.00 (3H, s), 0.87 (9H, s) 0.93 (3H, d, J=6 Hz), 1.85–2.55 (2H, m), 3.30–4.20 (4H, m), 5.30 (1H, brs), 6.80–7.10 (3H, m), 7.15–7.75 (9H, m)

MS: 480 (M+H)$^+$

EXAMPLE 22

This compound was prepared by a similar procedure to that of Example 16.

1-[(2S,3R)-5-(1,1'-biphenyl-2-yloxy)-2-hydroxy-3-pentyl]imidazole-4-carboxamide (22).

IR (KBr, cm$^{-1}$): 3600–2800, 1658, 1593, 1479, 1427, 1261, 1234, 1122, 1088, 1059

NMR (DMSO-d$_6$, δ): 0.86 (3H, d, J=6 Hz), 1.95–2.50 (2H, m), 3.40–4.10 (4H, m), 5.13 (1H, d, J=5 Hz), 6.85–7.10 (3H, m), 7.15–7.70 (10H, m)

MS: 366 (M+H)$^+$

EXAMPLE 23

This compound was prepared by a similar procedure to that of Example 15.

1-[(2S,3R)-2-(tert-butyldimethylsilyloxy)-5-(3-isoquinolyloxy)-3-pentyl]imidazole-4-carboxamide (23).

IR (KBr, cm$^{-1}$): 3600–2800, 1666, 1591, 1261, 1099

NMR (CDCl$_3$, δ): 0.01 (3H, s), 0.06 (3H, s), 0.89 (9H, s), 1.09 (3H, d, J=6 Hz), 2.10–2.70 (2H, m), 3.90–4.50 (4H, m), 5.34 (1H, brs), 6.90 (1H, brs), 6.92 (1H, s), 7.30–7.75 (5H, m), 7.87 (1H, d, J=8 Hz), 8.90 (1H, s)

MS: 455 (M+H)$^+$

EXAMPLE 24

This compound was prepared by a similar procedure to that of Example 16.

1-[(2S,3R)-2-hydroxy-5-(3-isoquinolyloxy)-3-pentyl]imidazole-4-carboxamide (24).

IR (KBr, cm$^{-1}$): 3600–2800, 1660, 1591, 1450, 1267, 1234, 1130, 1090, 1051

NMR (DMSO-d$_6$, δ): 0.93 (3H, d, J=6 Hz), 2.15–2.60 (2H, m) 3.65–4.35 (4H, m), 5.18 (1H, d, J=5 Hz), 7.03 (1H, brs), 7.11 (1H, s), 7.25 (1H, brs), 7.35–7.85 (5H, m), 8.00 (1H, d, J=8 Hz), 9.00 (1H, s)

MS: 341 (M+H)$^+$

Preparation 2

Under N$_2$, to a suspension of benzyltriphenylphosphonium bromide (980 mg, 2.26 mmol) in acetonitrile (10 ml) was added DBU at room temperature. After stirring for 10 min., 5-(benzyloxy)-1-methyl-1H-indole-2-carbaldehyde (500 mg, 1.88 mmol) was added and the mixture was stirred overnight at room temperature. The resulting mixture was filtered and washed with acetonitrile. The filtrate was concentrated in vacuo and then the residue was purified by silica gel (70 g) chromatography eluted with chloroform to give 5-(benzyloxy)-1-methyl-2-(2-phenylethenyl)-1H-indole (221 mg, 34.5%).

IR (KBr, cm$^{-1}$): 3050, 2860, 1612, 1456, 1238, 1029

NMR (CDCl$_3$, δ): 3.79 (3H, s), 5.11 (2H, s), 6.85–7.60 (16H, m)

MS: 340 (M+H)$^+$

Preparation 3

To a solution of 5-(benzyloxy)-1-methyl-2-(2-phenylethenyl)-1H-indole (204 mg, 0.601 mmol) in EtOH (5 ml) and THF (5 ml) was added 10% palladium on carbon (50 mg). The resulting mixture was stirred under hydrogen (2 atm) for 15 h at room temperature. The mixture was filtered through Celite and washed with EtOH. The filtrate was concentrated in vacuo and then the residue was purified by silica gel (4.5 g) chromatography eluted with chloroform to give 1-methyl-2-(2-phenylethyl)-1H-indol-5-ol (110 mg, 72.8%).

NMR (CDCl$_3$, δ): 3.02 (4H, s), 3.57 (3H, s), 4.42 (1H, s) 6.19 (1H, s), 6.73 (1H, dd, J=9.2 Hz), 6.96 (1H, d, J=2 Hz), 7.11 (1H, d, J=9 Hz), 7.15–7.40 (5H, m)

MS: 252 (M+H)$^+$

EXAMPLE 25

This compound was prepared by a similar procedure to that of Example 15.

1-{(2S,3R)-2-(tert-butyldimethylsilyloxy)-5-[1-methyl-2-(2-phenylethyl)-1H-indol-5-yloxy]-3-pentyl}imidazole-4-carboxamide (25).

NMR (CDCl$_3$, δ): 0.02 (3H, s), 0.06 (3H, s), 0.91 (9H, s) 1.10 (3H, d, J=6 Hz), 2.00–2.65 (2H, m), 3.02 (4H, s), 3.56 (3H, s), 3.57–4.40 (4H, m), 5.33 (1H, brs), 6.20 (1H, s), 6.73 (1H, dd, J=9.2 Hz), 6.91 (1H, d, J=2 Hz), 6.94 (1H, brs), 7.11 (1H, d, J=9 Hz), 7.15–7.35 (5H, m), 7.44 (1H, s), 7.64 (1H, s)

MS: 561 (M+H)$^+$

EXAMPLE 26

This compound was prepared by a similar procedure to that of Example 16.

1-{(2S,3R)-2-hydroxy-5-[1-methyl-2-(2-phenylethyl)-1H-indol-5-yloxy]-3-pentyl}imidazole-4-carboxamide (26).

NMR (DMSO-d$_6$, δ): 0.93 (3H, d, J=6 Hz), 2.05–2.65 (2H, m), 2.98 (4H, s), 3.45–4.35 (7H, m), 5.17 (1H, d, J=5 Hz), 6.12 (1H, s), 6.65 (1H, dd, J=9.2 Hz), 6.86 (1H, d, J=2 Hz), 7.03 (1H, brs), 7.10–7.35 (7H, m), 7.69 (1H, s), 7.74 (1H, s)

MS: 447 (M+H)$^+$

EXAMPLE 27

This compound was prepared by a similar procedure to that of Example 15.

1-[(2S,3R)-5-(1,1'-biphenyl-4-yloxy)-2-(tert-butyldimethylsilyloxy)-3-pentyl]imidazole-4-carboxamide (27).

NMR (CDCl$_3$, δ): 0.03 (3H, s), 0.07 (3H, s), 0.90 (9H, s) 1.11 (3H, d, J=6 Hz), 2.00–2.65 (2H, m), 3.55–4.35 (4H, m), 5.35 (1H, brs), 6.87 (2H, d, J=7 Hz), 6.90 (1H, brs), 7.25–7.60 (8H, m), 7.64 (1H, s)

MS: 480 (M+H)$^+$

EXAMPLE 28

This compound was prepared by a similar procedure to that of Example 16.

1-[(2S,3R)-5-(1,1'-biphenyl-4-yloxy)-2-hydroxy-3-pentyl]imidazole-4-carboxamide (28).

mp. 191–193° C.

IR (KBr, cm$^{-1}$): 3600–2800, 1655, 1602, 1485, 1243, 1124, 1084, 1038

NMR (DMSO-d$_6$, δ): 0.93 (3H, d, J=6 Hz), 2.10–2.60 (2H, m), 3.50–4.30 (4H, m), 5.19 (1H, d, J=5 Hz), 6.85–7.10 (3H, m), 7.15–7.65 (8H, m), 7.70 (1H, s), 7.75 (1H, s)

MS: 366 (M+H)$^+$

EXAMPLE 29

This compound was prepared by a similar procedure to that of Example 15.

1-[(2S,3R)-2-(tert-butyldimethylsilyloxy)-5-(3-tert-butylphenoxy)-3-pentyl]imidazole-4-carboxamide.

NMR (CDCl$_3$, δ): 0.02 (3H, s), 0.06 (3H, s), 0.91 (9H, s) 1.10 (3H, d, J=6 Hz), 1.28 (9H, s), 2.00–2.60 (2H, m), 3.55–4.35 (4H, m), 5.36 (1H, brs), 6.50–7.25 (5H, m), 7.43 (1H, s), 7.63 (1H, s)

MS: 460 (M+H)$^+$

EXAMPLE 30

This compound was prepared by a similar procedure to that of Example 16.

1-[(2S,3R)-5-(3-tert-butylphenoxy)-2-hydroxy-3-pentyl]imidazole-4-carboxamide (30).

IR (KBr, cm$^{-1}$): 3600–2800, 1662, 1608, 1572, 1485, 1427, 1271, 1238, 1128, 1093

NMR (DMSO-d$_6$, δ): 0.92 (3H, d, J=6 Hz), 2.05–2.60 (2H, m), 3.50–4.30 (4H, m), 5.17 (1H, d, J=5 Hz), 6.55–7.35 (6H, m), 7.69 (1H, s), 7.74 (1H, s)

MS: 346 (M+H)$^+$

EXAMPLE 31

This compound was prepared by a similar procedure to that of Example 15.

1-{(2S,3R)-2-(tert-butyldimethylsilyloxy)-5-[3-(2-thienyl)phenoxy]-3-pentyl}imidazole-4-carboxamide (31).

NMR (CDCl$_3$, δ): 0.03 (3H, s), 0.07 (3H, s), 0.91 (9H, s), 1.11 (3H, d, J=6 Hz), 2.00–2.65 (2H, m), 3.55–4.35 (4H, m), 5.36 (1H, brs), 6.65–7.35 (8H, m), 7.43 (1H, s), 7.64 (1H, s)

MS: 486 (M+H)$^+$

EXAMPLE 32

This compound was prepared by a similar procedure to that of Example 16.

1-{(2S,3R)-2-hydroxy-5-[3-(2-thienyl)phenoxy]-3-pentyl}imidazole-4-carboxamide (32).

IR (KBr, cm$^{-1}$): 3600–2800, 1657, 1595, 1483, 1419, 1265, 1232, 1090, 1057

NMR (DMSO-d$_6$, δ): 0.93 (3H, d, J=6 Hz), 2.10–2.60 (2H, m) 3.55–4.35 (4H, m), 5.18 (1H, d, J=5. Hz), 6.70–7.60 (9H, m), 7.71 (1H, s), 7.76 (1H, s)

MS: 372 (M+H)$^+$

EXAMPLE 33

This compound was prepared by a similar procedure to that of Example 15.

1-{(2S,3R)-2-(tert-butyldimethylsilyloxy)-5-[2-(2-thienyl)phenoxy]-3-pentyl}imidazole-4-carboxamide (33).

NMR (CDCl$_3$, δ): 0.00 (3H, s), 0.05 (3H, s), 0.91 (9H, s), 1.08 (3H, d, J=6 Hz), 2.00–2.75 (2H, m), 3.55–4.45 (4H, m), 5.31 (1H, brs), 6.75–7.45 (8H, m), 7.55–7.70 (2H, m)

MS: 486 (M+H)$^+$

EXAMPLE 34

This compound was prepared by a similar procedure to that of Example 16.

1-{(2S,3R)-2-hydroxy-5-[2-(2-thienyl)phenoxy]-3-pentyl}imidazole-4-carboxamide (34).

IR (KBr, cm$^{-1}$): 3600–2800, 1658, 1592, 1483, 1446, 1415, 1238, 1119, 1090, 1057

NMR (DMSO-d$_6$, δ): 0.96 (3H, d, J=6 Hz), 2.10–2.70 (2H, m), 3.60–4.40 (4H, m), 5.21 (1H, d, J=5 Hz), 6.90–7.35 (6H, m), 7.50–7.80 (5H, m)

MS: 372 (M+H)$^+$

Preparation 4

To a stirred solution of 2-benzyl-4-(3-methoxyphenyl)thiazole (1.0 g, 3.55 mmol) in CH$_2$Cl$_2$ (20 ml) was added a solution of 1.0 M BBr$_3$ in CH$_2$Cl$_2$ (4.26 ml) at −78° C. The resulting mixture was stirred at −78° C. for 30 min and then allowed to warm up to room temperature. The mixture was quenched with water and extracted with ether. The organic layer was washed with brine, dried (magnesium sulfate) and evaporated in vacuo. The residue was triturated with chloroform and dried under reduced pressure to give 3-(2-benzylthiazol-4-yl)phenol (760 mg, 80%).

IR (KBr, cm$^{-1}$): 3600–2600, 1599, 1498, 1440, 1246, 1176, 1144, 1070

NMR (DMSO-d$_6$, δ): 4.38 (2H, s), 6.65–6.80 (1H, m), 7.10–7.45 (8H, m), 7.86 (1H, s), 9.47 (1H, brs)

MS: 268 (M+H)$^+$

EXAMPLE 35

This compound was prepared by a similar procedure to that of Example 15.

1-{(2S,3R)-5-[3-(2-benzylthiazol-4-yl)phenoxy]-2-(tert-butyldimethylsilyloxy)-3-pentyl}imidazole-4-carboxamide (35).

NMR (CDCl$_3$, δ): 0.03 (3H, s), 0.06 (3H, s), 0.91 (9H, s), 1.11 (3H, d, J=6 Hz), 2.05–2.65 (2H, m), 3.60–4.45 (6H, m), 5.32 (1H, brs), 6.70–7.80 (1H, m), 6.92 (1H, brs), 7.20–7.50 (10H, m), 7.65 (1H, s)

MS: 577 (M+H)$^+$

EXAMPLE 36

This compound was prepared by a similar procedure to that of Example 16.

1-{(2S,3R)-5-[3-(2-benzylthiazol-4-yl)phenoxy]-2-hydroxy-3-pentyl}imidazole-4-carboxamide (36).

IR (KBr, cm$^{-1}$): 3600–2800, 1658, 1592, 1495, 1460, 1415, 1240, 1119, 1090, 1059

NMR (DMSO-d$_6$, δ): 0.94 (3H, d, J=6 Hz), 2.10–2.60 (2H, m), 3.50–4.30 (4H, m), 4.38 (2H, s), 5.18 (1H, d, J=5 Hz), 6.70–7.55 (11H, m), 7.71 (1H, s), 7.76 (1H, s), 7.96 (1H, s)

MS: 463 (M+H)$^+$

EXAMPLE 37

This compound was prepared by a similar procedure to that of Example 15.

1-{(2S,3R)-2-(tert-butyldimethylsilyloxy)-5-[3-(2-phenylthiazol-4-yl)phenoxy]-3-pentyl}imidazole-4-carboxamide (37).

NMR (CDCl$_3$, δ): 0.03 (3H, s), 0.07 (3H, s), 0.92 (9H, s), 1.12 (3H, d, J=6 Hz), 2.00–2.65 (2H, m), 3.60–4.40 (4H, m), 5.34 (1H, brs), 6.70–7.00 (2H, m), 7.20–7.75 (9H, m), 7.95–8.10 (2H, m)

MS: 563 (M+H)$^+$

EXAMPLE 38

This compound was prepared by a similar procedure to that of Example 16.

1-{(2S,3R)-2-hydroxy-5-[3-(2-phenylthiazol-4-yl)phenoxy]-3-pentyl}imidazole-4-carboxamide (38).

IR (KBr, cm$^{1-}$): 3600–2800, 1658, 1593, 1479, 1240, 1169, 1090, 1059

NMR (DMSO-d$_6$, δ): 0.95 (3H, d, J=6 Hz), 2.10–2.65 (2H, m), 3.55–4.35 (4H, m), 5.20 (1H, d, J=5 Hz), 6.75–6.95 (1H, m), 7.03 (1H, brs), 7.25 (1H, brs), 7.35 (1H, t, J=8 Hz), 7.40–7.69 (5H, m), 7.72 (1H, s), 7.77 (1H, s), 7.95–8.10 (2H, m), 8.19 (1H, s)

MS: 449 (M+H)$^+$

EXAMPLE 39

This compound was prepared by a similar procedure to that of Example 15.

1-[(2S,3R)-5-(3-bromophenoxy)-2-(tert-butyldimethylsilyloxy)-3-pentyl]imidazole-4-carboxamide (39).

NMR (CDCl$_3$, δ): 0.02 (3H, s), 0.06 (3H, s), 0.91 (9H, s), 1.09 (3H, d, J=6 Hz), 2.00–2.65 (2H, m), 3.50–4.30 (4H, m), 5.36 (1H, brs), 6.60–7.15 (5H, m), 7.41 (1H, s), 7.62 (1H, s)

MS: 482 (M+H)$^+$ ($^{79}$Br), 484 (M+H)$^+$ ($^{81}$Br)

EXAMPLE 40

This compound was prepared by a similar procedure to that of Example 16.

1-[(2S,3R)-5-(3-bromophenoxy)-2-hydroxy-3-pentyl]imidazole-4-carboxamide (40).

IR (KBr, cm$^{-1}$): 3600–2800, 1664, 1593, 1236, 1092

NMR (DMSO-d$_6$, δ): 0.92 (3H, d, J=6 Hz), 2.05–2.60 (2H, m), 3.50–4.30 (4H, m), 5.18 (1H, d, J=5 Hz), 6.80–7.35 (6H, m), 7.69 (1H, s), 7.74 (1H, s)

MS: 368 (M+H)$^+$ ($^{79}$Br), 370 (M+H)$^+$ ($^{81}$Br)

EXAMPLE 41

To a solution of 1-[(2S,3R)-5-(3-bromophenoxy)-2-hydroxy-3-pentyl]imidazole-4-carboxamide in DME (5 ml) was added Pd(PPh$_3$)$_4$ (29.3 mg, 0.025 mmol)at ambient temperature under N$_2$. After stirring for 20 min., benzothiophene-2-boronic acid (54.2 mg, 0.304 mmol) and a solution of Na$_2$CO$_3$ (40.3 mg, 0.38 mmol) in H$_2$O (1 ml) were added and the mixture was refluxed for 3 h. The mixture was cooled to room temperature and partitioned between ethyl acetate (20 ml) and H$_2$O. The organic layer was washed successively with saturated NaHCO$_3$ aqueous solution, H$_2$O and then brine, dried (sodium sulfate) and evaporated in vacuo. The residue was purified by silica gel chromatography eluting with chloroform/methanol (100:1 to 20:1) to give 1-{(2S,3R)-5-[3-(2-benzo[b]thiophenyl)phenoxy]-2-hydroxy-3-pentyl}imidazole-4-carboxamide (41) (66.9 mg, 62.6%).

IR (KBr, cm$^{-1}$): 3600–2800, 1658, 1594, 1432, 1261, 1171, 1092

NMR (DMSO-d$_6$, δ): 0.94 (3H, d, J=6 Hz), 2.10–2.60 (2H, m), 3.50–4.35 (4H, m), 5.20 (1H, d, J=5 Hz), 6.80–7.50 (8H, m), 7.65–8.05 (5H, m)

MS: 422 (M+H)$^+$

EXAMPLE 42

This compound was prepared by a similar procedure to that of Example 15.

1-{(2S,3R)-2-(tert-butyldimethylsilyloxy)-5-[3-(4-morpholinyl)phenoxy]-3-pentyl}imidazole-4-carboxamide (42).

IR (KBr, cm$^{-1}$): 3600–2800, 1666, 1600, 1259, 1191, 1118

NMR (CDCl$_3$, δ): 0.02 (3H, s), 0.06 (3H, s), 0.91 (9H, s), 1.09 (3H, d, J=6 Hz), 2.00–2.60 (2H, m), 3.13 (4H, t, J=5 Hz), 3.50–4.30 (8H, m), 5.34 (1H, brs), 6.20–6.65 (3H, m), 6.92 (1H, brs), 7.13 (1H, t, J=8 Hz), 7.41 (1H, s), 7.62 (1H, s)

MS: 489 (M+H)$^+$

EXAMPLE 43

This compound was prepared by a similar procedure to that of Example 16.

1-{(2S,3R)-2-hydroxy-5-[3-(4-morpholinyl)phenoxy]-3-pentyl}imidazole-4-carboxamide (43).

IR (KBr, cm$^{-1}$): 3600–2800, 1660, 1600, 1493, 1450, 1261, 1190, 1117

NMR (DMSO-d$_6$, δ): 0.92 (3H, d, J=6 Hz), 2.05–2.55 (2H, m), 3.04 (4H, t, J=5 Hz), 3.55–4.30 (8H, m), 5.16 (1H, brs), 6.20–6.65 (3H, m), 6.90–7.15 (2H, m), 7.24 (1H, brs), 7.68 (1H, s), 7.72 (1H, s)

MS: 375 (M+H)$^+$

Preparation 5

To a solution of 3-iodophenol (1.0 g, 4.55 mmol) in DME (10 ml) was added Pd(PPh$_3$)$_4$ (263 mg, 0.227 mmol) at ambient temperature under N$_2$. After stirring for 20 min., 5-chlorothiophene-2-boronic acid (886 mg, 5.45 mmol) and a solution of Na$_2$CO$_3$ (723 mg, 6.82 mmol) in H$_2$O (3 ml) were added and the mixture was refluxed for 2 h. The mixture was cooled to room temperature and partitioned between ethyl acetate (30 ml) and H$_2$O. The organic layer was washed with saturated NaHCO$_3$ aqueous solution, H$_2$O and then brine, dried (sodium sulfate) and evaporated in vacuo. The residue was purified by silica gel (15 g) chromatography eluting with hexane/ethyl acetate (10:1) to give 3-(5-chloro-2-thienyl)phenol (0.88 g, 91.9%).

IR (KBr, cm$^{-1}$): 3600–2800, 1599, 1454, 1250, 1217, 1088, 787

NMR (CDCl$_3$, δ): 4.87 (1H, s), 6.70–6.80 (1H, m), 6.88 (1H, d, J=4 Hz), 6.98 (1H, t, J=2 Hz), 7.00–7.32 (3H, m)

MS: 209 (M–H)$^-$ ($^{35}$Cl), 211 (M–H)$^-$ ($^{37}$Cl)

EXAMPLE 44

This compound was prepared by a similar procedure to that of Example 15.

1-{(2S,3R)-2-(tert-butyldimethylsilyloxy)-5-[3-(5-chloro-2-thienyl)phenoxy]-3-pentyl}imidazole-4-carboxamide (44).

NMR (CDCl$_3$, δ): 0.03 (3H, s), 0.07 (3H, s), 0.91 (9H, s), 1.11 (3H, d, J=6 Hz), 2.05–2.65 (2H, m), 3.55–4.33 (4H, m), 5.32 (1H, brs), 6.65–7.35 (7H, m), 7.43 (1H, s), 7.64 (1H, s)

MS: 520 (M+H)$^+$ ($^{35}$Cl), 522 (M+H)$^+$ ($^{37}$Cl)

EXAMPLE 45

This compound was prepared by a similar procedure to that of Example 16.

1-{(2S,3R)-5-[3-(5-chloro-2-thienyl)phenoxy]-2-hydroxy-3-pentyl}imidazole-4-carboxamide (45).

IR (KBr, cm$^{-1}$): 3600–2800, 1658, 1593, 1485, 1425, 1265, 1088

NMR (DMSO-d$_6$, δ): 0.93 (3H, d, J=6 Hz), 2.10–2.65 (2H, m), 3.50–4.30 (4H, m), 5.18 (1H, d, J=5 Hz), 6.70–7.45 (8H, m), 7.70 (1H, s), 7.75 (1H, s)

MS: 406 (M+H)$^+$ ($^{35}$Cl), 408 (M+H)$^+$ ($^{37}$Cl)

Preparation 6

This compound was prepared by a similar procedure to that of Preparation 5.

3-(5-Methyl-2-thienyl)phenol.

IR (KBr, cm$^{-1}$): 3600–2800, 1585, 1444, 1223, 1186, 847, 779

NMR (CDCl$_3$, δ): 2.50 (3H, s), 4.81 (1H, s), 6.60–6.80 (2H, m), 6.95–7.30 (4H, m)

MS: 189 (M–H)$^-$

EXAMPLE 46

This compound was prepared by a similar procedure to that of Example 15.

1-{(2S,3R)-2-(tert-butyldimethylsilyloxy)-5-[3-(5-methyl-2-thienyl)phenoxy]-3-pentyl}imidazole-4-carboxamide (46).

NMR (CDCl$_3$, δ): 0.03 (3H, s), 0.06 (3H, s), 0.91 (9H, s), 1.10 (3H, d, J=6 Hz), 2.00–2.65 (5H, m), 3.55–4.35 (4H, m), 5.34 (1H, brs), 6.60–7.30 (7H, m), 7.43 (1H, s), 7.64 (1H, s)

MS: 500 (M+H)$^+$

EXAMPLE 47

This compound was prepared by a similar procedure to that of Example 16.

1-{(2S,3R)-2-hydroxy-5-[3-(5-methyl-2-thienyl)phenoxy]-3-pentyl}imidazole-4-carboxamide (47).

IR (KBr, cm$^{-1}$): 3600–2800, 1658, 1599, 1495, 1427, 1267, 1228, 1090, 1053

NMR (DMSO-d$_6$, δ): 0.93 (3H, d, J=6 Hz), 2.10–2.60 (5H, m), 3.50–4.30 (4H, m), 5.18 (1H, d, J=5 Hz), 6.65–7.35 (8H, m), 7.70 (1H, s), 7.75 (1H, s)

MS: 386 (M+H)$^+$

EXAMPLE 48

This compound was prepared by a similar procedure to that of Example 15.

1-[(2S,3R)-2-(tert-butyldimethylsilyloxy)-5-(2-quinolyloxy)-3-pentyl]imidazole-4-carboxamide (48).

NMR (CDCl$_3$, δ): 0.01 (3H, s), 0.06 (3H, s), 0.88 (9H, s), 1.07 (3H, d, J=6 Hz), 2.10–2.70 (2H, m), 3.90–4.65 (4H, m), 5.46 (1H, brs), 6.83 (1H, d, J=9 Hz), 6.95 (1H, brs), 7.10–7.85 (6H, m), 7.98 (1H, d, J=9 Hz)

MS: 455 (M+H)$^+$

EXAMPLE 49

This compound was prepared by a similar procedure to that of Example 16.

1-[(2S,3R)-2-hydroxy-5-(2-quinolyloxy)-3-pentyl]imidazole-4-carboxamide (49).

IR (KBr, cm$^{-1}$): 3600–2800, 1658, 1608, 1425, 1267, 1238, 1111, 1088

NMR (DMSO-d$_6$, δ): 0.93 (3H, d, J=6 Hz), 2.20–2.45 (2H, m), 3.75–4.45 (4H, m), 5.17 (1H, d, J=5 Hz), 6.95 (1H, d, J=9 Hz), 7.05 (1H, brs), 7.25 (1H, brs), 7.35–7.95 (6H, m), 8.21 (1H, d, J=9 Hz)

MS: 341 (M+H)$^+$

EXAMPLE 50

This compound was prepared by a similar procedure to that of Example 15.

1-{(2S,3R)-5-[3-(2-benzoxazolyl)phenoxy]-2-(tert-butyldimethylsilyloxy)-3-pentyl}imidazole-4-carboxamide (50).

IR (KBr, cm$^{-1}$): 3600–2800, 1666, 1558, 1454, 1242, 1103, 1038

NMR (CDCl$_3$, δ): 0.04 (3H, s), 0.07 (3H, s), 0.92 (9H, s), 1.12 (3H, d, J=6 Hz), 2.05–2.70 (2H, m), 3.65–4.35 (4H, m), 5.33 (1H, brs), 6.80–7.05 (2H, m), 7.30–7.70 (4H, m), 7.52–7.90 (5H, m)

MS: 521 (M+H)$^+$

EXAMPLE 51

This compound was prepared by a similar procedure to that of Example 16.

1-{(2S,3R)-5-[3-(2-benzoxazolyl)phenoxy]-2-hydroxy-3-pentyl}imidazole-4-carboxamide (51).

IR (KBr, cm$^{-1}$): 3600–2800, 1658, 1592, 1554, 1450, 1236, 1088

NMR (DMSO-d$_6$, δ): 0.95 (3H, d, J=6 Hz), 2.10–2.60 (2H, m) 3.55–4.35 (4H, m), 5.20 (1H, d, J=5 Hz), 7.02 (1H, brs), 7.09–7.19 (1H, m), 7.24 (1H, brs), 7.33–7.90 (9H, m)

MS: 407 (M+H)$^+$

EXAMPLE 52

This compound was prepared by a similar procedure to that of Example 15.

1-{(2S,3R)-5-[3-(2-benzofuranyl)phenoxy]-2-(tert-butyldimethylsilyloxy)-3-pentyl}imidazole-4-carboxamide (52).

NMR (CDCl$_3$, δ): 0.04 (3H, s), 0.07 (3H, s), 0.92 (9H, s), 1.12 (3H, d, J=6 Hz), 2.05–2.70 (2H, m), 3.60–4.35 (4H, m), 5.36 (1H, brs), 6.70–6.85 (1H, m), 6.92 (1H, brs), 7.01 (1H, s), 7.15–7.70 (10H, m)

MS: 520 (M+H)$^+$

EXAMPLE 53

This compound was prepared by a similar procedure to that of Example 16.

1-{(2S,3R)-5-[3-(2-benzofuranyl)phenoxy]-2-hydroxy-3-pentyl)imidazole-4-carboxamide (53).

IR (KBr, cm$^{-1}$): 3600–2800, 1658, 1599, 1568, 1450, 1261, 1234, 1090, 1055

NMR (DMSO-d$_6$, δ): 0.95 (3H, d, J=6 Hz), 2.10–2.60 (2H, m) 3.60–4.35 (4H, m), 5.19 (1H, d, J=5 Hz), 6.80–6.95 (1H, m), 7.02 (1H, brs), 7.15–7.53 (7H, m), 7.56–7.85 (4H, m)

MS: 406 (M+H)$^+$

EXAMPLE 54

This compound was prepared by a similar procedure to that of Example 15.

1-{2S,3R}-5-[3-(1H-benzimidazol-2-yl)phenoxy]-2-(tert-butyldimethylsilyloxy)-3-pentyl}imidazole-4-carboxamide (54).

MS: 520 (M+H)$^+$

EXAMPLE 55

This compound was prepared by a similar procedure to that of Example 16.

1-{(2S,3R)-5-[3-(1H-benzimidazol-2-yl)phenoxy]-2-hydroxy-3-pentyl}imidazole-4-carboxamide (55).

IR (KBr, cm$^{-1}$): 3600–2800, 1658, 1599, 1460, 1267, 1236, 1095

NMR (DMSO-d$_6$, δ): 0.95 (3H, d, J=6 Hz), 2.10–2.60 (2H, m), 3.60–4.35 (4H, m), 5.21 (1H, d, J=5 Hz), 6.90–7.30 (5H, m), 7.42 (1H, t, J=8 Hz), 7.50–7.85 (6H, m)

MS: 406 (M+H)$^+$

Preparation 7

This compound was prepared by a similar procedure to that of Preparation 5.

4'-Chloro-1,1'-biphenyl-3-ol.

IR (KBr, cm$^{-1}$): 3600–2800, 1593, 1475, 1292, 1201, 1083, 825, 777

NMR (CDCl$_3$, δ): 4.93 (1H, s), 6.75–6.90 (1H, m), 7.02 (1H, t, J=2 Hz), 7.05–7.60 (6H, m)

MS: 203 (M–H)$^{31}$ ($^{35}$Cl), 205 (M–H)$^-$ ($^{37}$Cl)

EXAMPLE 56

This compound was prepared by a similar procedure to that of Example 15.

1-{(2S,3R)-2-(tert-butyldimethylsilyloxy)-5-[(4'-chloro-1,1'-biphenyl-3-yl)oxy]-3-pentyl}imidazole-4-carboxamide (56).

NMR (CDCl$_3$, δ): 0.03 (3H, s), 0.07 (3H, s), 0.91 (9H, s), 1.11 (3H, d, J=6 Hz), 2.00–2.65 (2H, m), 3.55–4.35 (4H, m), 5.34 (1H, brs), 6.65–7.18 (4H, m), 7.20–7.55 (6H, m), 7.64 (1H, s)

MS: 514 (M+H)$^+$ ($^{35}$Cl), 516 (M+H)$^+$ ($^{37}$Cl)

EXAMPLE 57

This compound was prepared by a similar procedure to that of Example 16.

1-{(2S,3R)-5-[(4'-chloro-1,1'-biphenyl-3-yl)oxy]-2-hydroxy-3-pentyl}imidazole-4-carboxamide (57).

IR (KBr, cm$^{-1}$): 3600–2800, 1658, 1593, 1473, 1263, 1238, 1091, 1060

NMR (DMSO-d$_6$, δ): 0.93 (3H, d, J=6 Hz), 2.10–2.60 (2H, m), 3.55–4.30 (4H, m), 5.17 (1H, d, J=5 Hz), 6.75–7.55 (8H, m), 7.60–7.85 (4H, m)

MS: 400 (M+H)$^+$ ($^{35}$Cl), 402 (M+H)$^+$ ($^{37}$Cl)

Preparation 8

This compound was prepared by a similar procedure to that of Preparation 5.

3'-Chloro-1,1'-biphenyl-3-ol.

IR (KBr, cm$^{-1}$): 3600–2800, 1595, 1466, 1238, 1199, 1092, 1045, 773

NMR (CDCl$_3$, δ): 4.91 (1H, s), 6.75–6.90 (1H, m), 7.03 (1H, t, J=2 Hz), 7.08–7.60 (6H, m)

MS: 203 (M–H)$^-$ ($^{35}$Cl), 205 (M–H)$^-$ ($^{37}$Cl)

EXAMPLE 58

This compound was prepared by a similar procedure to that of Example 15.

1-{(2S,3R)-2-(tert-butyldimethylsilyloxy)-5-[(3'-chloro-1,1'-biphenyl-3-yl)oxy]-3-pentyl}imidazole-4-carboxamide (58).

NMR (CDCl$_3$, δ): 0.03 (3H, s), 0.07 (3H, s), 0.91 (9H, s) 1.11 (3H, d, J=6 Hz), 2.00–2.65 (2H, m), 3.55–4.35 (4H, m), 5.33 (1H, brs), 6.70–7.18 (4H, m), 7.20–7.45 (5H, m), 7.53 (1H, s), 7.64 (1H, s)

MS: 514 (M+H)$^+$ ($^{35}$Cl), 516 (M+H)$^+$ ($^{37}$Cl)

EXAMPLE 59

This compound was prepared by a similar procedure to that of Example 16.

1-{(2S,3R)-5-[(3'-chloro-1,1'-biphenyl-3-yl)oxy]-2-hydroxy-3-pentyl}imidazole-4-carboxamide (59).

IR (KBr, cm$^{-1}$): 3600–2800, 1658, 1593, 1465, 1263, 1205, 1090, 1085, 1045

NMR (DMSO-d$_6$, δ): 0.93 (3H, d, J=6 Hz), 2.10–2.60 (2H, m), 3.55–4.30 (4H, m), 5.18 (1H, d, J=5 Hz), 6.80–7.80 (12H, m)

MS: 400 (M+H)$^+$ ($^{35}$Cl), 402 (M+H)$^+$ ($^{37}$Cl)

Preparation 9

This compound was prepared by a similar procedure to that of Preparation 5.

2'-Chloro-1,1'-biphenyl-3-ol.

IR (KBr, cm$^{-1}$) 3600–2800, 1589, 1462, 1240, 1190, 1078, 1039

NMR (CDCl$_3$, δ): 4.90 (1H, s), 6.75–7.05 (3H, m), 7.15–7.52 (5H, m)

MS: 203 (M–H)$^-$ ($^{35}$Cl), 205 (M–H)$^-$ ($^{37}$Cl)

EXAMPLE 60

This compound was prepared by a similar procedure to that of Example 15.

1-{(2S,3R)-2-(tert-butyldimethylsilyloxy)-5-[(2'-chloro-1,1'-biphenyl-3-yl)oxy]-3-pentyl}imidazole-4-carboxamide (60).

NMR (CDCl$_3$, δ): 0.02 (3H, s), 0.06 (3H, s), 0.91 (9H, s), 1.10 (3H, d, J=6 Hz), 2.00–2.65 (2H, m), 3.55–4.35 (4H, m), 5.33 (1H, brs), 6.75–7.05 (4H, m), 7.20–7.50 (6H, m), 7.63 (1H, s)

MS: 514 (M+H)$^+$ ($^{35}$Cl), 516 (M+H)$^+$ ($^{37}$Cl)

EXAMPLE 61

This compound was prepared by a similar procedure to that of Example 16.

1-{(2S,3R)-5-[(2'-chloro-1,1'-biphenyl-3-yl)oxy]-2-hydroxy-3-pentyl}imidazole-4-carboxamide (61).

IR (KBr, cm$^{-1}$): 3600–2800, 1658, 1589, 1464, 1259, 1203, 1124, 1085, 1045

NMR (DMSO-d$_6$, δ): 0.92 (3H, d, J=6 Hz), 2.10–2.60 (2H, m) 3.55–4.30 (4H, m), 5.1.6 (1H, d, J=5 Hz), 6.80–7.05 (4H, m), 7.23 (1H, brs), 7.28–7.60 (5H, m), 7.69 (1H, s), 7.74 (1H, s)

MS: 400 (M+H)$^+$ ($^{35}$Cl), 402 (M+H)$^+$ ($^{37}$Cl)

EXAMPLE 62

This compound was prepared by a similar procedure to that of Example 15.

1-{(2S,3R)-2-(tert-butyldimethylsilyloxy)-5-[(4'-methoxy-1,1'-biphenyl-3-yl)oxy]-3-pentyl}imidazole-4-carboxamide (62).

IR (KBr, cm$^{-1}$): 3600–2800, 1666, 1602, 1251, 1103, 1034

NMR (CDCl$_3$, δ): 0.02 (3H, s), 0.06 (3H, s), 0.91 (9H, s) 1.10 (3H, d, J=6 Hz), 2.00–2.65 (2H, m), 3.55–4.35 (7H, m), 5.32 (1H, brs), 6.65–7.55 (10H, m), 7.64 (1H, s)

MS: 510 (M+H)$^+$

EXAMPLE 63

This compound was prepared by a similar procedure to that of Example 16.

1-{(2S,3R)-2-hydroxy-5-[(4'-methoxy-1,1'-biphenyl-3-yl)oxy]-3-pentyl}imidazole-4-carboxamide (63).

IR (KBr, cm$^-$): 3600–2800, 1660, 1601, 1479, 1410, 1248, 1205, 1184, 1024

NMR (DMSO-d$_6$, δ): 0.93 (3H, d, J=6 Hz), 2.10–2.60 (2H, m), 3.55–4.30 (7H, m), 5.17 (1H, d, J=5 Hz), 6.70–7.35 (8H, m), 7.57 (2H, d, J=9 Hz), 7.70 (1H, s), 7.75 (1H, s)

MS: 396 (M+H)$^+$

Preparation 10

This compound was prepared by a similar procedure to that of Preparation 5.

3'-Methoxy-1,1'-biphenyl-3-ol.

IR (KBr, cm$^{-1}$: 3600–2800, 1599, 1238, 1161, 1088, 802

NMR (CDCl$_3$, δ): 3.86 (3H, s), 4.88 (1H, s), 6.75–6.95 (2H, m), 7.00–7.40 (6H, m)

MS: 199 (M–H)$^-$

EXAMPLE 64

This compound was prepared by a similar procedure to that of Example 15.

1-{(2S,3R)-2-(tert-butyldimethylsilyloxy)-5-[(3'-methoxy-1,1'-biphenyl-3-yl)oxy]-3-pentyl}imidazole-4-carboxamide (64).

NMR (CDCl$_3$, δ): 0.02 (3H, s), 0.06 (3H, s), 0.91 (9H, s), 1.10 (3H, d, J=6 Hz), 2.00–2.65 (2H, m), 3.60–4.35 (7H, m), 5.32 (1H, brs), 6.70–7.40 (9H, m), 7.43 (1H, s), 7.64 (1H, s)

MS: 510 (M+H)$^+$

EXAMPLE 65

This compound was prepared by a similar procedure to that of Example 16.

1-{(2S,3R)-2-hydroxy-5-[(3'-methoxy-1,1'-biphenyl-3-yl)oxy]-3-pentyl}imidazole-4-carboxamide (65).

IR (KBr, cm$^{-1}$): 3600–2800, 1660, 1599, 1473, 1234, 1090

NMR (DMSO-d$_6$, δ): 0.93 (3H, d, J=6 Hz), 2.10–2.60 (2H, m), 3.55–4.30 (7H, m), 5.19 (1H, d, J=5 Hz), 6.80–7.45 (10H, m), 7.71 (1H, s), 7.75 (1H, S)

MS: 396 (M+H)$^+$

Preparation 11

This compound was prepared by a similar procedure to that of Preparation 5.

3-(2-Methoxy-5-pyridyl)phenol.

IR (KBr, cm$^{-1}$): 3600–2800, 1603, 1240, 1130, 1088, 1038, 791

NMR (CDCl$_3$, δ): 3.99 (3H, s), 5.41 (1H, s), 6.75–6.90 (2H, m), 7.01 (1H, t, J=2 Hz), 7.04–7.15 (1H, m), 7.31 (1H, t, J=8 Hz), 7.78 (1H, dd, J=8.2 Hz), 8.39 (1H, d, J=2 Hz)

MS: 202 (M+H)$^+$

EXAMPLE 66

This compound was prepared by a similar procedure to that of Example 15.

1-{(2S,3R)-2-(tert-butyldimethylsilyloxy)-5-[3-(2-methoxy-5-pyridyl)phenoxy]-3-pentyl}imidazole-4-carboxamide (66).

IR (KBr, cm$^{-1}$): 3600–2800, 1666, 1602, 1284, 1257, 1099, 1027

NMR (CDCl$_3$, δ): 0.03 (3H, s), 0.07 (3H, s), 0.91 (9H, s), 1.11 (3H, d, J=6 Hz), 2.00–2.65 (2H, m), 3.55–4.35 (7H, m), 5.33 (1H, brs), 6.70–7.40 (6H, m), 7.43 (1H, s), 7.64 (1H, s), 7.75 (1H, dd, J=8,3 Hz), 8.35 (1H, d, J=3 Hz)

MS: 511 (M+H)$^+$

EXAMPLE 67

This compound was prepared by a similar procedure to that of Example 16.

1-{(2S,3R)-2-hydroxy-5-[3-(2-methoxy-5-pyridyl)phenoxy]-3-pentyl}imidazole-4-carboxamide (67).

IR (KBr, cm$^{-1}$): 3600–2800, 1660, 1602, 1479, 1282, 1242, 1092, 1024

NMR (DMSO-d$_6$, δ): 0.93 (3H, d, J=6 Hz), 2.10–2.60 (2H, m), 3.55–4.30 (7H, m), 5.19 (1H, d, J=5 Hz), 6.75–7.40 (7H, m), 7.71 (1H, s), 7.75 (1H, s), 7.99 (1H, dd, J=9.3 Hz), 8.46 (1H, d, J=3 Hz)

MS: 397 (M+H)$^+$

EXAMPLE 68

This compound was prepared by a similar procedure to that of Example 15.

1-{(2S,3R)-2-(tert-butyldimethylsilyloxy)-5-[(6-phenyl-2-pyridyl)oxy]-3-pentyl}imidazole-4-carboxamide (68).

NMR (CDCl$_3$, δ): 0.00 (3H, s), 0.04 (3H, s), 0.88 (9H, s) 1.07 (3H, d, J=6 Hz), 2.05–2.70 (2H, m), 3.90–4.60 (4H, m), 5.33 (1H, brs), 6.62 (1H, d, J=8 Hz), 6.91 (1H, brs), 7.25–7.50 (5H, m), 7.60 (1H, d, J=8 Hz), 7.65 (1H, s), 7.88–8.00 (2H, m)

MS: 481 (M+H)$^+$

EXAMPLE 69

This compound was prepared by a similar procedure to that of Example 16.

1-{(2S,3R)-2-hydroxy-5-[(6-phenyl-2-pyridyl)oxy]-3-pentyl}imidazole-4-carboxamide (69).

IR (KBr, cm$^{-1}$): 3600–2800, 1658, 1581, 1444, 1248, 1088

NMR (DMSO-d$_6$, δ): 0.93 (3H, d, J=6 Hz), 2.10–2.60 (2H, m) 3.75–4.45 (4H, m), 5.17 (1H, d, J=5 Hz), 6.71 (1H, d, J=8 Hz), 7.03 (1H, brs), 7.24 (1H, brs), 7.32–7.60 (4H, m), 7.60 (1H, d, J=8 Hz), 7.65–8.10 (5H, m)

MS: 367 (M+H)$^+$

EXAMPLE 70

This compound was prepared by a similar procedure to that of Example 15.

1-{(2S,3R)-2-(tert-butyldimethylsilyloxy)-5-[(4'-fluoro-1,1'-biphenyl-3-yl)oxy]-3-pentyl}imidazole-4-carboxamide (70).

NMR (CDCl$_3$, δ): 0.03 (3H, s), 0.07 (3H, s), 0.91 (9H, s), 1.11 (3H, d, J=6 Hz), 2.00–2.65 (2H, m), 3.60–4.35 (4H, m), 5.33 (1H, brs), 6.70–7.20 (6H, m), 7.24–7.56 (4H, m), 7.64 (1H, s)

MS: 498 (M+H)$^+$

EXAMPLE 71

This compound was prepared by a similar procedure to that of Example 16.

1-{(2S,3R)-5-[(4'-fluoro-1,1'-biphenyl-3-yl)oxy]-2-hydroxy-3-pentyl}imidazole-4-carboxamide (71).

IR (KBr, cm$^{-1}$): 3600–2800, 1658, 1600, 1481, 1234, 1092

NMR (DMSO-d$_6$, δ): 0.93 (3H, d, J=6 Hz), 2.10–2.60 (2H, m) 3.55–4.30 (4H, m), 5.18 (1H, d, J=5 Hz), 6.75–7.40 (8H, m), 7.55–7.85 (4H, m)

MS: 384 (M+H)$^+$

Preparation 12

This compound was prepared by a similar procedure to that of Preparation 5.

4'-trifluoromethyl-1,1'-biphenyl-3-ol.

IR (KBr, cm$^{-1}$): 3600–2800, 1589, 1458, 1408, 1325, 1190, 1134, 1070, 839, 781

NMR (CDCl$_3$, δ): 4.90 (1H, s), 6.80–6.95 (1H, m), 7.07 (1H, t, J=2 Hz), 7.10–7.22 (1H, m), 7.34 (1H, t, J=8 Hz), 7.60–7.75 (4H, m)

MS: 237 (M–H)$^-$

EXAMPLE 72

This compound was prepared by a similar procedure to that of Example 15.

1-[(2S,3R)-2-(tert-butyldimethylsilyloxy)-5-{[4'-(trifluoromethyl)-1,1'-biphenyl-3-yl)oxy}-3-pentyl]imidazole-4-carboxamide (72).

NMR (CDCl$_3$, δ): 0.03 (3H, s), 0.07 (3H, s), 0.91 (9H, s) 1.11 (3H, d, J=6 Hz), 2.10–2.60 (2H, m), 3.65–4.30 (4H, m), 5.33 (1H, brs), 6.82 (1H, m), 6.91 (1H, brs), 7.00 (1H, t, J=2 Hz), 7.17 (1H, m), 7.34 (1H, t, J=8 Hz), 7.43 (1H, s), 7.62–7.72 (5H, m)

MS: 548 (M+H)$^+$

EXAMPLE 73

This compound was prepared by a similar procedure to that of Example 16.

1-[(2S,3R)-2-hydroxy-5-{[4'-(trifluoromethyl)-1,1'-biphenyl-3-yl]oxy}-3-pentyl]imidazole-4-carboxamide (73).

IR (KBr, cm$^{-1}$): 3600–2800, 1658, 1599, 1328, 1165, 1119, 1070

NMR (DMSO-d$_6$, δ): 0.94 (3H, d, J=6 Hz), 2.10–2.60 (2H, m), 3.60–4.35 (4H, m), 5.18 (1H, d, J=5 Hz), 6.85–7.45 (6H, m), 7.63–8.00 (6H, m)

MS: 434 (M+H)$^+$

Preparation 13

This compound was prepared by a similar procedure to that of Example 15.

Ethyl 1-{(2S,3R)-2-(tert-butyldimethylsilyloxy)-5-[3-(1H-pyrrol-1-yl)-2-naphthyloxy]-3-pentyl}imidazole-4-carboxylate.

NMR (CDCl$_3$, δ): −0.04 (3H, s), 0.03 (3H, s), 0.91 (9H, s), 1.08 (3H, d, J=6 Hz), 1.34 (3H, t, J=7 Hz), 2.00–2.65 (2H, m), 3.40–4.40 (6H, m), 6.38 (2H, t, J=2 Hz) 7.06 (2H, t, J=2 Hz), 7.13 (2H, s), 7.30–7.55 (3H, m), 7.65–7.80 (3H, m)

MS: 548 (M+H)$^+$

Preparation 14

This compound was prepared by a similar procedure to that of Example 16.

Ethyl 1-{(2S,3R)-2-hydroxy-5-[3-(1H-pyrrol-1-yl)-2-naphthyloxy]-3-pentyl}imidazole-4-carboxylate.

IR (KBr, cm$^{-1}$): 3600–2800, 1714, 1506, 1236, 1192, 1099

NMR (CDCl$_3$, δ): 1.14 (3H, d, J=6 Hz), 1.34 (3H, t, J=7 Hz), 2.05–2.65 (2H, m), 2.81 (1H, br), 3.40–4.40 (6H, m), 6.39 (2H, t, J=2 Hz), 7.07 (2H, t, J=2 Hz), 7.16 (2H, s), 7.30–7.60 (3H, m), 7.65–7.85 (3H, m)

MS: 434 (M+H)$^+$

EXAMPLE 74

This compound was prepared by a similar procedure to that of Preparation 1.

1-{(2S,3R)-2-hydroxy-5-[3-(1H-pyrrol-1-yl)-2-naphthyloxy]-3-pentyl}imidazole-4-carboxamide (74).

IR (KBr, cm$^{-1}$): 3600–2800, 1658, 1595, 1500, 1463, 1410, 1255, 1097

NMR (DMSO-d$_6$, δ): 0.92 (3H, d, J=6 Hz), 2.10–2.60 (2H, m), 3.50–4.25 (4H, m), 5.18 (1H, d, J=5 Hz), 6.29 (2H, t, J=2 Hz), 7.02 (1H, brs), 7.20 (2H, t, J=2 Hz), 7.24 (1H, brs), 7.35–7.55 (4H, m), 7.72 (1H, s), 7.75–7.95 (3H, m)

MS: 405 (M+H)$^+$

Preparation 15

This compound was prepared by a similar procedure to that of Preparation 13.

Ethyl 1-[(2S,3R)-2-(tert-butyldimethylsilyloxy)-5-(1-methyl-1H-indol-5-yloxy)-3-pentyl]imidazole-4-carboxylate.

NMR (CDCl$_3$, δ): 0.01 (3H, s), 0.06 (3H, s), 0.91 (9H, s), 1.13 (3H, d, J=6 Hz), 1.37 (3H, t, J=7 Hz), 2.00–2.60 (2H, m), 3.55–4.45 (9H, m), 6.35 (1H, d, J=3 Hz), 6.78 (1H, dd, J=9.2 Hz), 6.97 (1H, d, J=2 Hz), 7.01 (1H, d, J=3 Hz), 7.18 (1H, d, J=9 Hz), 7.52 (1H, s), 7.68 (1H, s)

MS: 486 (M+H)$^+$

Preparation 16

This compound was prepared by a similar procedure to that of Example 16.

Ethyl 1-[(2S,3R)-2-hydroxy-5-(1-methyl-1H-indol-5-yloxy)-3-pentyl]imidazole-4-carboxylate.

IR (KBr, cm$^{-1}$): 3600–2800, 1699, 1313, 1234, 1147, 1026

NMR (DMSO-d$_6$, δ): 0.93 (3H, d, J=6 Hz), 1.25 (3H, t, J=7 Hz), 2.10–2.55 (2H, m), 3.45–4.35 (9H, m), 5.18 (1H, d, J=5 Hz), 6.26 (1H, d, J=3 Hz), 6.72 (1H, dd, J=9.2 Hz), 6.94 (1H, d, J=2 Hz), 7.23 (1H, d, J=3 Hz), 7.28 (1H, d, J=9 Hz), 7.77 (1H, s), 7.96 (1H, s)

MS: 372 (M+H)$^+$

EXAMPLE 75

This compound was prepared by a similar procedure to that of Preparation 1.

1-[(2S,3R)-2-hydroxy-5-(1-methyl-1H-indol-5-yloxy)-3-pentyl]imidazole-4-carboxamide (75).

mp. 211–213.5° C.

IR (KBr, cm$^{-1}$): 3600–2800, 1666, 1583, 1495, 1398, 1242, 1151, 1103

NMR (DMSO-d$_6$, δ): 0.93 (3H, d, J=6 Hz), 2.05–2.55 (2H, m) 3.45–4.35 (7H, m), 5.18 (1H, brs), 6.27 (1H, d, J=3 Hz), 6.73 (1H, dd, J=9.2 Hz), 6.94 (1H, d, J=2 Hz), 7.01 (1H, brs), 7.15–7.35 (3H, m), 7.69 (1H, s), 7.74 (1H, s)

MS: 343 (M+H)$^+$

Preparation 17

To a stirred mixture of ethyl 1-[(2S,3R)-2-(tert-butyldimethylsilyloxy)-5-hydroxy-3-pentyl]imidazole-4-carboxylate (500 mg, 1.4 mmol) and methanesulfonyl chloride (321 mg, 2.8 mmol) in dichloromethane (15 ml) was added dropwise triethylamine (284 mg, 2.8 mmol) at ice-bath temperature. After 1 h, the reaction mixture was partitioned between dichloromethane and water. The organic layer was washed with brine, dried (magnesium sulfate), and concentrated in vacuo to give ethyl 1-[(2S,3R)-2-(tert-butyldimethylsilyloxy)-5-methanesulfonyloxy-3-pentyl]imidazole-4-carboxylate (642 mg, 105%) as a syrup. This material was used for the next reaction without further purification.

Preparation 18

To a mixture of ethyl 1-[(2S,3R)-2-(tert-butyldimethylsilyloxy)-5-methanesulfonyloxy-3-pentyl]imidazole-4-carboxylate (160 mg, 0.368 mmol) and 2-naphthalenethiol (118 mg, 0.736 mmol) in DMF (5 ml) was added potassium carbonate (102 mg, 0.736 mmol) at room temperature and the reaction mixture was stirred for 2 hours. The resulting reaction mixture was poured into water (25 ml) and extracted with ethyl acetate. The organic layer was washed with brine, dried (sodium sulfate) and evaporated in vacuo. The residue was purified by silica gel (10 g) chromatography eluting with chloroform/methanol (100:1 to 50:1) to give ethyl 1-[(2S,3R)-2-(tert-butyldimethylsilyloxy)-5-(2-naphthylthio)-3-pentyl]imidazole-4-carboxylate (146 mg, 79.5%).

IR (neat, cm$^{-1}$): 3425, 2954, 2860, 1722, 1591, 1238, 1089

NMR (CDCl$_3$, δ): −0.08 (3H, s), −0.04 (3H, s), 0.78 (9H, s), 1.00 (3H, d, J=6 Hz), 1.39 (3H, t, J=7 Hz), 2.00–2.35 (2H, m), 2.65–3.10 (2H, m), 3.75–4.25 (2H, m), 4.37 (2H, q, J=7 Hz), 7.30–7.55 (4H, m), 7.60 (1H, s), 7.65–7.85 (4H, m)

MS: 499 (M+H)$^+$

Preparation 19

This compound was prepared by a similar procedure to that of Example 16.

Ethyl 1-[(2S,3R)-2-hydroxy-5-(2-naphthylthio)-3-pentyl]imidazole-4-carboxylate.

IR (neat, cm$^{-1}$): 3600–2800, 1720, 1226, 1193, 1126

NMR (DMSO-d$_6$, δ): 0.86 (3H, d, J=6 Hz), 1.27 (3H, t, J=7 Hz), 2.10–2.35 (2H, m), 2.70–2.95 (2H, m), 3.70–4.30 (4H, m), 5.14 (1H, d, J=5 Hz), 7.30–7.55 (3H, m), 7.62–7.80 (6H, m)

MS: 385 (M+H)$^+$

EXAMPLE 76

This compound was prepared by a similar procedure to that of Preparation 1.

1-[(2S,3R)-2-hydroxy-5-(2-naphthylthio)-3-pentyl]imidazole-4-carboxamide (76).

IR (KBr, cm$^{-1}$): 3600–2800, 1657, 1591, 1413, 1261, 1240, 1126, 1097, 1076

NMR (DMSO-d$_6$, δ): 0.87 (3H, d, J=6 Hz), 2.05–2.40 (2H, m) 2.65–3.00 (2H, m), 3.70–4.20 (2H, m), 5.13 (1H, d, J=5 Hz), 7.06 (1H, brs), 7.28 (1H, brs), 7.30–7.60 (3H, m), 7.62–7.95 (6H, m)

MS: 356 (M+H)$^+$

Preparation 20

This compound was prepared by a similar procedure to that of Preparation 18.

Ethyl 1-[(2S,3R)-2-(tert-butyldimethylsilyloxy)-5-(1-naphthylthio)-3-pentyl]imidazole-4-carboxylate.

IR (neat, cm$^{-1}$): 3446, 2956, 2858, 1724, 1236, 1184, 1130

NMR (CDCl$_3$, δ): −0.09 (3H, s), −0.02 (3H, s), 0.82 (9H, s) 0.96 (3H, d, J=6 Hz), 1.39 (3H, t, J=7 Hz), 2.00–2.25 (2H, m), 2.45–3.05 (2H, m), 3.75–4.20 (2H, m), 4.37 (2H, q, J=7 Hz), 7.30–7.62 (6H, m), 7.70–7.90 (2H, m), 8.37 (1H, dd, J=9.2 Hz)

MS: 499 (M+H)$^+$

Preparation 21

This compound was prepared by a similar procedure to that of Example 16.

Ethyl 1-[(2S,3R)-2-hydroxy-5-(1-naphthylthio)-3-pentyl]imidazole-4-carboxylate.

IR (neat, cm$^{-1}$): 3600–2800, 1720, 1223, 1196, 1126

NMR (DMSO-d$_6$, δ): 0.85 (3H, d, J=6 Hz), 1.27 (3H, t, J=7 Hz), 2.05–2.35 (2H, m), 2.65–2.95 (2H, m), 3.65–4.30 (4H, m), 5.14 (1H, d, J=5 Hz), 7.35–7.66 (4H, m), 7.72–8.03 (4H, m), 8.12–8.28 (1H, m)

MS: 385 (M+H)$^+$

EXAMPLE 77

This compound was prepared by a similar procedure to that of Preparation 1.

1-[(2S,3R)-2-hydroxy-5-(1-naphthylthio)-3-pentyl]imidazole-4-carboxamide (77).

IR (KBr, cm$^{-1}$): 3600–2800, 1658, 1593, 1413, 1336, 1261, 1128

NMR (DMSO-d$_6$, δ): 0.85 (3H, d, J=6 Hz), 2.05–2.35 (2H, m), 2.60–2.95 (2H, m), 3.65–4.25 (2H, m), 5.12 (1H, d, J=5 Hz), 7.04 (1H, brs), 7.27 (1H, brs), 7.35–8.03 (8H, m), 8.13–8.28 (1H, m)

MS: 356 (M+H)$^+$

Preparation 22

This compound was prepared by a similar procedure to that of Preparation 18.

Ethyl 1-[(2S,3R)-2-(tert-butyldimethylsilyloxy)-5-(2-quinolylthio)-3-pentyl]imidazole-4-carboxylate.

IR (neat, cm$^{-1}$): 3450, 2954, 2858, 1722, 1238, 1182, 1136, 1091

NMR (CDCl$_3$, δ): −0.06 (3H, s), 0.00 (3H, s), 0.79 (9H, s), 1.04 (3H, d, J=6 Hz), 1.40 (3H, t, J=7 Hz), 2.20–2.60 (2H, m), 2.80–3.50 (2H, m), 3.85–4.25 (2H, m), 4.38 (2H, q, J=7 Hz), 7.18 (1H, d, J=9 Hz), 7.35–7.80 (5H, m), 7.84–8.00 (2H, m)

MS: 500 (M+H)$^+$

Preparation 23

This compound was prepared by a similar procedure to that of Example 16.

Ethyl 1-[(2S,3R)-2-hydroxy-5-(2-quinolylthio)-3-pentyl]imidazole-4-carboxylate.

IR (neat, cm$^{-1}$): 3600–2800, 1718, 1230, 1193, 1132, 1092

NMR (DMSO-d$_6$, δ): 0.90 (3H, d, J=6 Hz), 1.28 (3H, t, J=7 Hz), 2.20–2.42 (2H, m), 2.80–3.30 (2H, m), 3.70–4.35 (4H, m), 5.14 (1H, d, J=5 Hz), 7.34 (1H, d, J=9 Hz), 7.40–7.95 (5H, m), 8.01 (1H, s), 8.14 (1H, d, J=9 Hz)

MS: 386 (M+H)$^+$

EXAMPLE 78

This compound was prepared by a similar procedure to that of Preparation 1.

1-[(2S,3R)-2-hydroxy-5-(2-quinolylthio)-3-pentyl)imidazole-4-carboxamide (78).

IR (KBr, cm$^{-1}$): 3600–2800, 1658, 1593, 1556, 1414, 1261, 1138, 1090

NMR (DMSO-d$_6$, δ): 0.91 (3H, d, J=6 Hz), 2.20–2.42 (2H, m) 2.75–3.30 (2H, m), 3.70–4.25 (2H, m), 5.11 (1H, d, J=5 Hz), 7.08 (1H, brs), 7.31 (1H, brs), 7.33 (1H, d, J=9 Hz), 7.40–7.95 (6H, m), 8.14 (1H, d, J=9 Hz)

MS: 357 (M+H)$^+$

Preparation 24

This compound was prepared by a similar procedure to that of Preparation 18.

Ethyl 1-[(2S,3R)-2-(tert-butyldimethylsilyloxy)-5-(3,4-dichlorophenylthio)-3-pentyl]imidazole-4-carboxylate.

IR (neat, cm$^{-1}$): 3446, 2956, 2858, 1724, 1236, 1184, 1130, 1105, 1027

NMR (CDCl$_3$, δ): −0.04 (3H, s), 0.02 (3H, s), 0.85 (9H, s) 1.03 (3H, d, J=6 Hz), 1.39 (3H, t, J=7 Hz), 1.95–2.35 (2H, m), 2.40–2.97 (2H, m), 3.80–4.15 (2H, m), 4.37 (2H, q, J=7 Hz), 7.09 (1H, dd, J=8.2 Hz), 7.35 (1H, d, J=8 Hz), 7.36 (1H, d, J=2 Hz), 7.50 (1H, s), 7.59 (1H, s)

MS: 517 (M+H)$^+$ ($^{35}$Cl×2), 519 (M+H)$^+$ ($^{35}$Cl–$^{37}$Cl)

Preparation 25

This compound was prepared by a similar procedure to that of Example 16.

Ethyl 1-[(2S,3R)-5-(3,4-dichlorophenylthio)-2-hydroxy-3-pentyl]imidazole-4-carboxylate.

IR (neat, cm$^{-1}$): 3600–2800, 1716, 1232, 1191, 1124, 1027

NMR (DMSO-d$_6$, δ): 0.85 (3H, d, J=6 Hz), 1.27 (3H, t, J=7 Hz), 2.05–2.30 (2H, m), 2.65–2.90 (2H, m), 3.70–4.30 (4H, m), 5.14 (1H, d, J=5 Hz), 7.24 (1H, dd, J=8.2 Hz), 7.50 (1H, d, J=2 Hz), 7.53 (1H, d, J=8 Hz), 7.78 (1H, s), 7.92 (1H, s)

MS: 403 (M+H)$^+$ ($^{35}$Cl×2), 405 (M+H)$^+$ ($^{35}$Cl–$^{37}$Cl)

EXAMPLE 79

This compound was prepared by a similar procedure to that of Preparation 1.

1-[(2S,3R)-5-(3,4-dichlorophenylthio)-2-hydroxy-3-pentyl]imidazole-4-carboxamide (79).

IR (KBr, cm$^{-1}$): 3600–2800, 1660, 1594, 1456, 1414, 1263, 1126, 1101

NMR (DMSO-d$_6$, δ): 0.86 (3H, d, J=6 Hz), 2.05–2.30 (2H, m) 2.65–2.90 (2H, m), 3.70–4.15 (2H, m), 5.13 (1H, d, J=5 Hz), 7.03 (1H, brs), 7.24 (1H, dd, J=8.2 Hz), 7.25 (1H, brs), 7.51 (1H, d, J=2 Hz), 7.53 (1H, d, J=8 Hz), 7.70 (1H, s), 7.72 (1H, s)

MS: 374 (M+H)$^+$ ($^{35}$Cl×2), 376 (M+H)$^+$ ($^{35}$Cl–$^{37}$Cl)

Preparation 26

This compound was prepared by a similar procedure to that of Preparation 18.

Ethyl 1-[(2S,3R)-2-(tert-butyldimethylsilyloxy)-5-(3,4-dimethylphenylthio)-3-pentyl]imidazole-4-carboxylate.

IR (neat, cm$^{-1}$): 3448, 2954, 2858, 1724, 1234, 1184, 1130, 1105, 1025

NMR (CDCl$_3$, δ)s: −0.06 (3H, s), 0.01 (3H, s), 0.84 (9H, s), 1.01 (3H, d, J=6 Hz), 1.39 (3H, t, J=7 Hz), 1.95–2.30 (8H, m), 2.35–2.95 (2H, m), 3.80–4.20 (2H, m), 4.37 (2H, q, J=7 Hz), 7.00–7.15 (1H, m), 7.44 (1H, s), 7.56 (1H, s)

MS: 477 (M+H)$^+$

Preparation 27

This compound was prepared by a similar procedure to that of Example 16.

Ethyl 1-[(2S,3R)-5-(3,4-dimethylphenylthio)-2-hydroxy-3-pentyl]imidazole-4-carboxylate.

IR (neat, cm$^{-1}$): 3600–2800, 1716, 1230, 1192, 1124, 1027

NMR (DMSO-d$_6$, δ): 0.86 (3H, d, J=6 Hz), 1.27 (3H, t, J=7 Hz), 2.00–2.30 (8H, m), 2.50–2.75 (2H, m), 3.65–4.30 (4H, m), 5.12 (1H, d, J=5 Hz), 6.90–7.10 (3H, m), 7.75 (1H, s), 7.89 (1H, s)

MS: 363 (M+H)$^+$

EXAMPLE 80

This compound was prepared by a similar procedure to that of Preparation 1.

1-[(2S,3R)-5-(3,4-dimethylphenylthio)-2-hydroxy-3-pentyl]imidazole-4-carboxamide (80).

IR (KBr, cm$^{-1}$): 3600–2800, 1658, 1595, 1489, 1415, 1263, 1238, 1126, 1093

NMR (DMSO-d$_6$, δ): 0.86 (3H, d, J=6 Hz), 2.00–2.25 (8H, m), 2.50–2.75 (2H, m), 3.70–4.15 (2H, m), 5.10 (1H, d, J=5 Hz), 6.95–7.12 (4H, m), 7.25 (1H, brs), 7.67 (2H, s)

MS: 334 (M+H)$^+$

Preparation 28

To a suspension of (2R,3S)-2-amino-1,3-butanediol 4-methylbenzenesulfonate (2.3 g) in nitromethane (32 mL) was added triethylamine (1.1 mL) and triethyl orthoformate (1.3 mL). The mixture was stirred at 110° C. for 0.5 hour and cooled in an ice-bath. A mixture of ethyl α-amino-α-cyanoacetate 4-methylbenzenesulfonate (2.0 g), triethylamine (1.0 mL) and acetonitrile (32 mL) was added to the reaction mixture, and the whole was stirred at 100° C. for 8 hours. The mixture was concentrated in vacuo and the residue was purified by column chromatography on silica gel (gradient elution; 10:1 to 5:1 chloroform-methanol containing 1% ammonium hydroxide) to give the crude product, which was further purified by column chromatography on silica gel (gradient elution; 20:1 to 10:1 to 5:1 ethyl acetate-1% ammonium hydroxide/methanol) to give ethyl 5-amino-1-[(1R,2S)-2-hydroxy-1-(hydroxymethyl)propyl]-1H-imidazole-4-carboxylate (1.0 g).

NMR (DMSO-d$_6$); 0.93 (3H, d, J=6 Hz), 1.23 (3H, t, J=7 Hz), 3.8–4.1 (4H, m), 4.12 (2H, q, J=7 Hz), 4.9–5.0 (1H, m), 5.17 (1H, d, J=5 Hz), 5.89 (2H, br s), 7.17 (1H, s)

Preparation 29

To a refluxing solution of isoamyl nitrite (1.5 mL) in tetrahydrofuran (4.6 mL) was added a solution of ethyl 5-amino-1-[(1R,2S)-2-hydroxy-1-(hydroxymethyl)propyl]-1H-imidazole-4-carboxylate (0.92 g) in tetrahydrofuran (23 mL) dropwise over 45 minutes, and the mixture was refluxed for 75 minutes. The reaction mixture was cooled to ambient temperature and concentrated in vacuo. The residue was purified by column chromatography on silica gel (gradient elution; 10:1 to 5:1 chloroform-1% ammonium hydroxide/methanol) to give ethyl 1-[(1R,2S)-2-hydroxy-1-(hydroxymethyl)propyl]-1H-imidazole-4-carboxylate (0.50 g).

NMR (DMSO-d$_6$); 0.88 (3H, d, J=6 Hz), 1.26 (3H, t, J=7 Hz), 3.7–4.1 (4H, m), 4.21 (2H, q, J=7 Hz), 4.86 (1H, br s) 5.07 (1H, br s), 7.72 (1H, d, J=1 Hz), 7.88 (1H, d, J=1 Hz)

Preparation 30

A mixture of ethyl 1-[(1R,2S)-2-hydroxy-1-(hydroxymethyl)propyl]-1H-imidazole-4-carboxylate (0.88 g), 4-chlorophenylsulfonyl chloride (1.2 g) and pyridine (8.8 mL) was stirred at 4° C. for 3 days. The mixture was poured into water, and extracted with ethyl acetate. The extract was washed with brine, dried over anhydrous sodium sulfate, and concentrated in vacuo. The residue was purified by column chromatography on silica gel (gradient elution; 50:1 to 25:1 chloroform-methanol) to give ethyl 1-[(1R,2S)-1-({[4-chlorophenyl]sulfonyl}oxy)methyl)-2-hydroxypropyl]-1H-imidazole-4-carboxylate (0.89 g).

NMR (DMSO-d$_6$); 0.84 (3H, d, J=6 Hz), 1.27 (3H, t, J=7 Hz), 3.8–4.0 (1H, m), 4.21 (2H, q, J=7 Hz), 4.3–4.4 (1H, m), 4.54 (2H, d, J=6 Hz), 5.39 (1H, d, J=5 Hz), 7.6–7.9 (6H, m)

Preparation 31

A mixture of 3,4-dichlorophenol (1.0 g), cesium carbonate (2.1 g) and N,N-dimethylformamide (6 mL) was stirred at 80° C. for an hour. To the mixture was added a solution of ethyl 1-[(1R,2S)-1-({[4-chlorophenyl]sulfonyl}oxy)methyl]-2-hydroxypropyl]-1H-imidazole-4-carboxylate (0.52 g) in N,N-dimethylformamide (6 mL). The reaction mixture was stirred at 80° C. overnight, cooled to ambient temperature and diluted with ethyl acetate. The precipitate was filtered off and the filtrate was successively washed with 1 N sodium hydroxide, water and brine, dried over anhydrous sodium sulfate, and concentrated in vacuo. The residue was purified by column chromatography on silica gel (elution; 25:1 chloroform-methanol) to give the crude product, which was further purified by recrystallization from 1:1 n-hexane-ethyl acetate (4 mL) to give ethyl 1-{(1R,2S)-1-[(3,4-dichlorophenoxy)methyl]-2-hydroxypropyl}-1H-imidazole-4-carboxylate (0.25 g).

mp: 101–103° C.

NMR (DMSO-d$_6$); 0.96 (3H, d, J=6 Hz), 1.25 (3H, t, J=7 Hz), 4.0–4.1 (1H, m), 4.20 (2H, q, J=7 Hz), 4.4–4.6 (3H, m), 5.3–5.4 (1H, br m), 6.93 (1H, dd, J=2 Hz, 9 Hz), 7.24 (1H, d, J=2 Hz), 7.51 (1H, d, J=9 Hz), 7.87 (1H, d, J=1 Hz), 8.03 (1H, s)

EXAMPLE 81

A mixture of ethyl 1-{(1R,2S)-1-[(3,4-dichlorophenoxy)methyl]-2-hydroxypropyl}-1H-imidazole-4-carboxylate (0.23 g), 28% ammonium hydroxide (12 mL) and 1,2-dimethoxyethane (6 mL) was heated at 100° C. in the stainless steel bottle for 24 hours. After cooling, the reaction mixture was concentrated in vacuo and the residue was purified by column chromatography on silica gel (gradient elution; 20:1 to 10:1 chloroform-methanol) to give the product, which was recrystallized from 1:5 n-hexane-ethyl acetate (12 mL) to give 1-{(1R,2S)-1-[(3,4-dichlorophenoxy)methyl]-2-hydroxypropyl}-1H-imidazole-4-carboxamide (81) (0.13 g).

mp: 115–121° C.

APCIMS: 344, 346 (M+H)

IR (KBr): 3328, 1664 cm$^{-1}$

NMR (DMSO-d$_6$); 0.95 (3H, d, J=6 Hz), 3.9–4.1 (1H, m), 4.3–4.6 (3H, m), 5.34 (1H, d, J=5 Hz), 6.94 (1H, dd, J=2 Hz, 9 Hz), 7.05 (1H, br, s), 7.25 (1H, d, J=2 Hz), 7.26 (1H, br, s), 7.51 (1H, d, J=9 Hz), 7.79 (1H, s), 7.80 (1H, s)

Preparation 32

This compound was prepared by a similar procedure to that of Preparation 5.

3'-hydroxy-1,1'-biphenyl-4-carbonitrile.

IR (KBr, cm$^{-1}$): 3500–2800, 2231, 1591, 1477, 1303, 1203, 839, 779

NMR (CDCl$_3$, δ): 5.10 (1H, s), 6.80–7.40 (4H, m), 7.55–7.80 (4H, m)

MS: 218 (M+Na)$^+$

EXAMPLE 82

This compound was prepared by a similar procedure to that of Example 15.

1-{(2S,3R)-2-(tert-butyldimethylsilyloxy)-5-[(4'-cyano-1,1'-biphenyl-3-yl)oxy]-3-pentyl}imidazole-4-carboxamide (82).

NMR (CDCl$_3$, δ): 0.03 (3H, s), 0.07 (3H, s), 0.91 (9H, s), 1.11 (3H, d, J=6 Hz), 2.05–2.70 (2H, m), 3.60–4.35 (4H, m), 5.38 (1H, brs), 6.75–7.00 (3H, m), 7.10–7.45 (3H, m), 7.55–7.80 (5H, m)

MS: 505 (M+H)$^+$

EXAMPLE 83

This compound was prepared by a similar procedure to that of Example 16.

1-{(2S,3R)-5-[(4'-cyano-1,1'-biphenyl-3-yl)oxy]-2-hydroxy-3-pentyl}imidazole-4-carboxamide (83).

IR (KBr, cm$^{-1}$): 3600–2800, 2240, 1658, 1595, 1209, 839

NMR (DMSO-d$_6$, δ): 0.94 (3H, d, J=6 Hz), 2.10–2.60 (2H, m) 3.60–4.30 (4H, m), 5.19 (1H, d, J=5 Hz), 6.85–7.45 (6H, m), 7.60–8.00 (6H, m)

MS: 391 (M+H)$^+$

Preparation 33

This compound was prepared by a similar procedure to that of Preparation 5.

4'-methyl-1,1'-biphenyl-3-ol.

IR (KBr, cm$^{-1}$): 3600–2800, 1595, 1481, 1296, 1192, 879, 775

NMR (CDCl$_{3, δ}$): 2.39 (3H, s), 4.83 (1H, s), 6.70–6.90 (1H, m), 6.95–7.55 (7H, m)

MS: 183 (M–H)$^-$

EXAMPLE 84

This compound was prepared by a similar procedure to that of Example 15.

1-{(2S,3R)-2-(tert-butyldimethylsilyloxy)-5-[(4'-methyl-1,1'-biphenyl-3-yl)oxy]-3-pentyl}imidazole-4-carboxamide (84).

NMR (CDCl$_3$, δ): 0.02 (3H, s), 0.06 (3H, s), 0.91 (9H, s) 1.10 (3H, d, J=6 Hz), 2.00–2.65 (5H, m), 3.55–4.35 (4H, m), 5.32 (1H, brs), 6.70–7.50 (10H, m), 7.64 (1H, s)

MS: 494 (M+H)$^+$

EXAMPLE 85

This compound was prepared by a similar procedure to that of Example 16.

1-{(2S,3R)-2-hydroxy-5-[(4'-methyl-1,1'-biphenyl-3-yl)oxy]-3-pentyl}imidazole-4-carboxamide (85).

IR (KBr, cm$^{-1}$): 3600–2800, 1658, 1595, 1479, 1410, 1263, 1090, 781

NMR (DMSO-d$_6$, δ): 0.94 (3H, d, J=6 Hz), 2.10–2.60 (5H, m) 3.55–4.35 (4H, m), 5.19 (1H, brs), 6.70–7.40 (8H, m), 7.57 (2H, d, J=8 Hz), 7.71 (1H, s), 7.76 (1H, s)

MS: 380 (M+H)$^+$

Preparation 34

This compound was prepared by a similar procedure to that of Preparation 5.

3-(6-chloro-3-pyridyl)phenol.

IR (KBr, cm$^{-1}$): 3500–2700, 1599, 1454, 1238, 1111

NMR (CDCl$_3$, δ): 5.85 (1H, s), 6.80–7.15 (3H, m), 7.25–7.50 (2H, m), 7.84 (1H, dd, J=8,3 Hz), 8.62 (1H, d, J=3 Hz)

MS: 204 (M–H)$^-$ ($^{35}$Cl), 206 (M–H)$^-$ ($^{37}$Cl)

EXAMPLE 86

This compound was prepared by a similar procedure to that of Example 15.

1-{(2S,3R)-2-(tert-butyldimethylsilyloxy)-5-[3-(6-chloro-3-pyridyl)phenoxy]-3-pentyl}imidazole-4-carboxamide (86).

NMR (CDCl$_3$, δ): 0.02 (3H, s), 0.07 (3H, s), 0.91 (9H, s), 1.10 (3H, d, J=6 Hz), 2.05–2.70 (2H, m), 3.60–4.35 (4H, m), 5.35 (1H, brs), 6.75–7.00 (3H, m), 7.11 (1H, d, J=8 Hz), 7.25–7.50 (3H, m), 7.64 (1H, s), 7.80 (1H, dd, J=8, 2 Hz), 8.56 (1H, d, J=2 Hz)

MS: 515 (M+H)$^+$ ($^{35}$Cl), 517 (M+H)$^+$ ($^{37}$Cl)

EXAMPLE 87

This compound was prepared by a similar procedure to that of Example 16.

1-{(2S,3R)-5-[3-(6-chloro-3-pyridyl)phenoxy]-2-hydroxy-3-pentyl}imidazole-4-carboxamide (87).

mp. 166–168° C.

IR (KBr, cm$^{-1}$): 3600–2800, 1652, 1592, 1456, 1236, 1105

NMR (DMSO-d$_6$, δ): 0.93 (3H, d, J=6 Hz), 2.10–2.60 (2H, m) 3.55–4.35 (4H, m), 5.19 (1H, d, J=5 Hz), 6.93 (1H, dd, J=8, 1 Hz), 7.03 (1H, brs), 7.10–7.45 (4H, m), 7.59 (1H, d, J=8 Hz), 7.71 (1H, s), 7.75 (1H, s), 8.14 (1H, dd, J=8, 2 Hz), 8.72 (1H, d, J=2 Hz)

MS: 401 (M+H)$^+$ ($^{35}$Cl), 403 (M+H)$^+$ ($^{37}$Cl)

Preparation 35

This compound was prepared by a similar procedure to that of Preparation 5.

2-(4-chlorophenyl)-6-methoxypyridine.

IR (KBr, cm$^{-1}$): 2976, 2943, 1579, 1464, 1254, 1020, 793

NMR (CDCl$_3$, δ): 4.03 (3H, s), 6.70 (1H, d, J=8 Hz), 7.20–7.70 (4H, m), 7.90–8.05 (2H, m)

MS: 220 (M+H)$^+$ ($^{35}$Cl), 222 (M+H)$^+$ ($^{37}$Cl)

Preparation 36

To a stirred solution of 2-(4-chlorophenyl)-6-methoxypyridine (450 mg, 2.05 mmol) in chlorobenzene (5 ml) was added AlCl$_3$ (1.09 g, 8.19 mmol) at room temperature. The resulting mixture was stirred under reflux for 10 min. The mixture was quenched with crushed ice under ice bath temperature and partitioned between ethyl acetate (20 ml) and HClaq. The organic layer was washed with water and brine, dried (magnesium sulfate) and evaporated in vacuo.

The residue was triturated with hexane and dried under reduced pressure to give 6-(4-chlorophenyl)-2(1H)-pyridinone (382 mg, 91%) as a white solid.

IR (KBr, cm$^{-1}$): 3600–2600, 1672, 1616, 1491, 1090, 791

NMR (DMSO-d$_6$, δ): 6.35–6.70 (2H, m), 7.35–7.75 (5H, m), 11.65 (1H, br)

MS: 228 (M+Na)$^+$ ($^{35}$Cl), 230 (M+Na)$^+$ ($^{37}$Cl)

EXAMPLE 88

This compound was prepared by a similar procedure to that of Example 15.

1-((2S,3R)-2-(tert-butyldimethylsilyloxy)-5-{[6-(4-chlorophenyl)-2-pyridyl]oxy}-3-pentyl)imidazole-4-carboxamide (88).

NMR (CDCl$_3$, δ): 0.02 (3H, s), 0.04 (3H, s), 0.88 (9H, s), 1.07 (3H, d, J=6 Hz), 2.05–2.70 (2H, m), 3.85–4.65 (4H, m), 5.38 (1H, brs), 6.64 (1H, d, J=8 Hz), 6.93 (1H, brs), 7.20–7.75 (6H, m), 7.87 (2H, d, J=8 Hz)

MS: 515 (M+H)$^+$ ($^{35}$Cl), 517 (M+H)$^+$ ($^{37}$Cl)

EXAMPLE 89

This compound was prepared by a similar procedure to that of Example 16.

1-((2S,3R)-2-hydroxy-5-{[6-(4-chlorophenyl)-2-pyridyl]oxy}-3-pentyl)imidazole-4-carboxamide (89).

IR (KBr, cm$^{-1}$): 3600–2800, 1662, 1591, 1444, 1251, 1092, 1020, 800

NMR (DMSO-d$_6$, δ): 0.93 (3H, d, J=6 Hz), 2.10–2.60 (2H, m), 3.75–4.45 (4H, m), 5.18 (1H, d, J=5 Hz), 6.73 (1H, d, J=8 Hz), 7.06 (1H, brs), 7.27 (1H, brs), 7.45–7.90 (6H, m), 8.01 (2H, d, J=9 Hz)

MS: 401 (M+H)$^+$ ($^{35}$Cl), 403 (M+H)$^+$ ($^{37}$Cl)

EXAMPLE 90

This compound was prepared by a similar procedure to that of Example 15.

1-{(2S,3R)-2-(tert-butyldimethylsilyloxy)-5-[(3',5'-dichloro-1,1'-biphenyl-3-yl)oxy]-3-pentyl}imidazole-4-carboxamide (90).

NMR (CDCl$_3$, δ): 0.03 (3H, s), 0.07 (3H, s), 0.91 (9H, s), 1.11 (3H, d, J=6 Hz), 2.05–2.65 (2H, m), 3.60–4.35 (4H, m), 5.35 (1H, brs), 6.70–7.00 (3H, m), 7.10 (1H, d, J=8 Hz), 7.25–7.50 (5H, m), 7.64 (1H, s)

EXAMPLE 91

This compound was prepared by a similar procedure to that of Example 16.

1-{(2S,3R)-5-[(3',5'-dichloro-1,1'-biphenyl-3-yl)oxy]-2-hydroxy-3-pentyl}imidazole-4-carboxamide (91).

IR (KBr, cm$^{-1}$): 3600–2800, 1657, 1591, 1558, 1236, 1092, 850, 795

NMR (DMSO-d$_6$, δ): 0.93 (3H, d, J=6 Hz), 2.10–2.60 (2H, m), 3.50–4.35 (4H, m), 5.19 (1H, d, J=5 Hz), 6.92 (1H, d, J=8, 1 Hz), 7.02 (1H, brs), 7.15–7.45 (4H, m), 7.50–7.80 (5H, m)

MS: 434 (M+H)$^+$ ($^{35}$Cl), 436 (M+H)$^+$ ($^{37}$Cl)

EXAMPLE 92

This compound was prepared by a similar procedure to that of Example 15.

1-[(2S,3R)-2-(tert-butyldimethylsilyloxy)-5-(7-methoxy-2-naphthyloxy)-3-pentyl]imidazole-4-carboxamide (92).

NMR (CDCl$_3$, δ): 0.03 (3H, s), 0.06 (3H, s), 0.91 (9H, s), 1.11 (3H, d, J=6 Hz), 2.10–2.65 (2H, m), 3.65–4.35 (7H, m), 5.34 (1H, brs), 6.80–7.05 (5H, m), 7.44 (1H, s), 7.55–7.70 (3H, m)

MS: 484 (M+H)$^+$

EXAMPLE 93

This compound was prepared by a similar procedure to that of Example 16.

1-[(2S,3R)-2-hydroxy-5-(7-methoxy-2-naphthyloxy)-3-pentyl]imidazole-4-carboxamide (93).

IR (KBr, cm$^{-1}$): 3600–2800, 1633, 1259, 1219, 1157, 1029, 835

NMR (DMSO-d$_6$, δ): 0.95 (3H, d, J=6 Hz), 2.10–2.60 (2H, m), 3.60–4.35 (7H, m), 5.20 (1H, d, J=5 Hz), 6.80–7.35 (6H, m), 6.60–7.85 (4H, m)

MS: 370 (M+H)$^+$

EXAMPLE 94

This compound was prepared by a similar procedure to that of Example 15.

1-[(2S,3R)-5-(7-bromo-2-naphthyloxy)-2-(tert-butyldimethylsilyloxy)-3-pentyl]imidazole-4-carboxamide (94).

NMR (CDCl$_3$, δ): 0.03 (3H, s), 0.07 (3H, s), 0.91 (9H, s), 1.11 (3H, d, J=6 Hz), 2.05–2.75 (2H, m), 3.60–4.35 (4H, m), 5.34 (1H, brs), 6.89 (1H, d, J=2 Hz), 6.90 (1H, brs), 7.07 (1H, dd, J=9.2 Hz), 7.34–7.75 (5H, m), 7.83 (1H, s)

MS: 532 (M+H)$^+$ ($^{79}$Br), 534 (M+H)$^+$ ($^{81}$Br)

EXAMPLE 95

This compound was prepared by a similar procedure to that of Example 16.

1-](2S,3R)-5-(7-bromo-2-naphthyloxy)-2-hydroxy-3-pentyl]imidazole-4-carboxamide (95).

IR (KBr, cm$^{-1}$): 3600–2800, 1682, 1649, 1244, 1128, 1087, 837

(DMSO-d$_6$, δ): 0.94 (3H, d, J=6 Hz), 2.10–2.65 (2H, m), 3.60–4.35 (4H, m), 5.20 (1H, d, J=5 Hz), 7.02 (1H, brs), 7.08–7.35 (3H, m), 7.43 (1H, dd, J=8.2 Hz), 7.60–7.90 (4H, m), 8.02 (1H, d, J=2 Hz)

MS: 418 (M+H)$^+$ ($^{79}$Br)

EXAMPLE 96

This compound was prepared by a similar procedure to that of Example 15.

1-[(2S,3R)-2-(tert-butyldimethylsilyloxy)-5-(7-chloro-2-naphthyloxy)-3-pentyl]imidazole-4-carboxamide (96).

IR (KBr, cm$^{-1}$): 3600–2800, 1664, 1250, 1092, 835

NMR (CDCl$_3$, δ): 0.03 (3H, s), 0.07 (3H, s), 0.91 (9H, s), 1.11 (3H, d, J=6 Hz), 2.05–2.70 (2H, m), 3.60–4.35 (4H, m), 5.36 (1H, brs), 6.89 (1H, d, J=2 Hz), 6.90 (1H, brs), 7.06 (1H, dd, J=9, 2 Hz), 7.15–7.35 (1H, m), 7.43 (1H, s), 7.55–7.75 (4H, m)

MS: 488 (M+H)$^+$ ($^{35}$Cl), 490 (M+H)$^+$ ($^{37}$Cl)

EXAMPLE 97

This compound was prepared by a similar procedure to that of Example 16.

1-[(2S,3R)-5-(7-chloro-2-naphthyloxy)-2-hydroxy-3-pentyl]imidazole-4-carboxamide (97).

mp. 139–141° C.

IR (KBr, cm$^{-1}$): 3600–2800, 1662, 1620, 1246, 1211, 1082, 839

NMR (DMSO-d$_6$, δ): 0.94 (3H, d, J=6 Hz), 2.10–2.65 (2H, m), 3.60–4.35 (4H, m), 5.20 (1H, d, J=5 Hz), 6.90–7.40 (5H, m), 7.60–7.95 (5H, m)

MS: 374 (M+H)$^+$ ($^{35}$Cl), 376 (M+H)$^+$ ($^{37}$Cl)

EXAMPLE 98

This compound was prepared by a similar procedure to that of Example 15.

1-[(2S,3R)-2-(tert-butyldimethylsilyloxy)-5-(7-cyano-2-naphthyloxy)-3-pentyl]imidazole-4-carboxamide (98).

NMR (CDCl$_3$, δ): 0.04 (3H, s), 0.08 (3H, s), 0.92 (9H, s), 1.12 (3H, d, J=6 Hz), 2.05–2.75 (2H, m), 3.60–4.35 (4H, m), 5.37 (1H, brs), 6.91 (1H, brs), 7.01 (1H, d, J=2 Hz), 7.22 (1H, dd, J=9.2 Hz), 7.45 (1H, s), 7.47 (1H, d, J=9 Hz), 7.65 (1H, s), 7.74 (1H, d, J=9 Hz), 7.82 (1H, d, J=9 Hz), 8.04 (1H, s)

MS: 479 (M+H)$^+$

EXAMPLE 99

This compound was prepared by a similar procedure to that of Example 16.

1-[(2S,3R)-5-(7-cyano-2-naphthyloxy)-2-hydroxy-3-pentyl]imidazole-4-carboxamide (99).

IR (KBr, cm$^{-1}$): 3600–2800, 2225, 1658, 1599, 1263, 1217, 1126, 1092, 842

NMR (DMSO-d$_6$, δ): 0.94 (3H, d, J=6 Hz), 2.10–2.65 (2H, m), 3.60–4.35 (4H, m), 5.20 (1H, brs), 7.05 (1H, brs), 7.15–7.45 (3H, m), 7.60 (1H, dd, J=8,1 Hz), 7.70–8.10 (4H, m), 8.36 (1H, s)

MS: 365 (M+H)$^+$

EXAMPLE 100

This compound was prepared by a similar procedure to that of Example 15.

1-((2S,3R)-2-(tert-butyldimethylsilyloxy)-5-{[2-(4-chlorophenyl)-1,3-benzoxazol-6-yl]oxy}-3-pentyl)imidazole-4-carboxamide (100).

IR (KBr, cm$^{-1}$): 3600–2800, 1666, 1592, 1481, 1261, 1145, 1095, 835

NMR (CDCl$_3$, δ): 0.04 (3H, s), 0.07 (3H, s), 0.92 (9H, s), 1.12 (3H, d, J=6 Hz), 2.05–2.70 (2H, m), 3.60–4.35 (4H, m), 5.35 (1H, brs), 6.80–7.05 (3H, m), 7.35–7.70 (5H, m), 8.12 (2H, d, J=9 Hz)

MS: 555 (M+H)$^+$ ($^{35}$Cl), 557 (M+H)$^+$ ($^{37}$Cl)

EXAMPLE 101

This compound was prepared by a similar procedure to that of Example 16.

1-((2S,3R)-5-{[2-(4-chlorophenyl)-1,3-benzoxazol-6-yl]oxy}-2-hydroxy-3-pentyl)imidazole-4-carboxamide (101).

IR (KBr, cm$^{-1}$): 3600–2800, 1654, 1617, 1481, 1267, 1146, 1053, 827

NMR (DMSO-d$_6$, δ): 0.94 (3H, d, J=6 Hz), 2.10–2.70 (2H, m), 3.60–4.35 (4H, m), 5.20 (1H, d, J=5 Hz), 6.80–7.45 (4H, m), 7.50–7.90 (5H, m), 8.12 (2H, d, J=8 Hz)

MS: 441 (M+H)$^+$ ($^{35}$Cl), 443 (M+H)$^+$ ($^{37}$Cl)

REFERENCE EXAMPLE 1

Under N$_2$, a cold (−75° C.) solution of oxalyl chloride (285 mg, 2.24 mmol) in CH$_2$Cl$_2$ (10 ml) was treated with DMSO (0.215 ml, 3.03 mmol) and stirred for 10 min. A solution of ethyl 1-[(2S,3R)-2-(tert-butyldimethylsilyloxy)-5-hydroxy-3-pentyl]imidazole-4-carboxylate (400 mg, 1.12 mmol) in CH$_2$Cl$_2$ (5 ml) was slowly added, the resulting mixture was stirred for 50 min at −75 to −45° C. and finally treated with triethylamine (0.59 ml). The reaction mixture was allowed to warm to 0° C., hydrolyzed with water (10 ml) and extracted with CH$_2$Cl$_2$ (20 ml×2). The combined organic layers were dried over sodium sulfate and evaporated in vacuo. The residue was purified by silica gel (13 g) chromatography eluting with chloroform/methanol (100:1) to give ethyl 1-[(2S,3R)-2-(tert-butyldimethylsilyloxy)-5-oxo-3-pentyl]imidazole-4-carboxylate (370 mg, 93%) as a colorless syrup.

IR (neat, cm$^{-1}$): 3435, 2958, 2860, 1722, 1709, 1547, 1238, 1092, 1034

NMR (CDCl$_3$, δ): −0.01 (3H, s), 0.04 (3H, s), 0.91 (9H, s), 1.09 (3H, d, J=6 Hz), 1.38 (3H, t, J=7 Hz), 3.00–3.13 (1H, m), 3.85–4.60 (5H, m), 7.56 (1H, s), 7.64 (1H, s)

MS: 377 (M+Na)$^+$

REFERENCE EXAMPLE 2

Under N$_2$, to a suspension of 2-naphthylmethyltriphenylphosphonium bromide (355 mg, 0.733 mmol) in THF (8 ml) and DMSO (4 ml) was added t-BuOK at room temperature. After stirring for 20 min., the mixture was cooled to 5–7° C. in an ice bath and then ethyl 1-[(2S,3R)-2-(tert-butyldimethylsilyloxy)-5-oxo-3-pentyl]imidazole-4-carboxylate (130 mg, 0.367 mmol) in THF (6 ml) was added. The mixture was stirred for 1 h at room temperature. The reaction mixture was poured into water (25 ml) and extracted with ethyl acetate. The organic layer was washed with brine, dried (sodium sulfate) and evaporated in vacuo. The residue was purified by silica gel (15 g) chromatography eluting with chloroform/methanol (100:1 to 50:1) to give ethyl 1-[(2S,3R)-2-(tert-butyldimethylsilyloxy)-6-(2-naphthyl)-5-hexen-3-yl]]imidazole-4-carboxylate (130 mg, 74.1%).

NMR (CDCl$_3$, δ): −0.03–0.08 (6H, m), 0.70–1.45 (15H, s), 2.60–3.20 (2H, m), 3.80–4.40 (4H, m), 5.35–6.75 (2H, m), 7.20–7.90 (9H, m)

MS: 479 (M+H)$^+$

REFERENCE EXAMPLE 3

This compound was prepared by a similar procedure to that of Preparation 3.

Ethyl 1-[(2S,3R)-2-(tert-butyldimethylsilyloxy)-6-(2-naphthyl)-3-hexyl]imidazole-4-carboxylate.

IR (neat, cm$^{-1}$): 3375, 2941, 2860, 1724, 1232, 1182, 1124, 1031

NMR (CDCl$_3$, δ): −0.05 (3H, s), 0.00 (3H, s), 0.83 (9H, s), 0.97 (3H, d, J=6 Hz), 1.39 (3H, t, J=7 Hz), 1.60–2.15 (4H, m), 2.77 (2H, t, J=7 Hz), 3.75–4.00 (2H, m), 4.36 (2H, q, J=7 Hz), 7.15–7.60 (6H, m), 7.70–7.87 (3H, m)

MS: 481 (M+H)$^+$

REFERENCE EXAMPLE 4

This compound was prepared by a similar procedure to that of Example 16.

Ethyl 1-[(2S,3R)-2-hydroxy-6-(2-naphthyl)-3-hexyl]imidazole-4-carboxylate.

IR (neat, cm$^{-1}$): 3600–2800, 1718, 1234, 1188, 1124, 1028

NMR (DMSO-d$_6$, δ): 0.87 (3H, d, J=6 Hz), 1.15–1.65 (5H, m), 1.70–2.10 (2H, m), 2.60–2.85 (2H, m), 3.65–4.10 (2H, m), 4.20 (2H, q, J=7 Hz), 5.07 (1H, d, J=5 Hz), 7.20–7.50 (3H, m), 7.61 (1H, s), 7.70–7.95 (5H, m)

MS: 367 (M+H)$^+$

REFERENCE EXAMPLE 5

This compound was prepared by a similar procedure to that of Preparation 1.

1-[(2S,3R)-2-hydroxy-6-(2-naphthyl)-3-hexyl]imidazole-4-carboxamide.

IR (KBr, cm$^{-1}$): 3600–2800, 1658, 1593, 1412, 1261, 1240, 1124, 1093

NMR (DMSO-d$_6$, δ): 0.87 (3H, d, J=6 Hz), 1.15–1.60 (2H, m), 1.70–2.10 (2H, m), 2.55–2.85 (2H, m), 3.65–4.10 (2H, m), 5.06 (1H, d, J=5 Hz), 7.02 (1H, brs), 7.24 (1H, brs), 7.31 (1H, d, J=8 Hz), 7.35–7.90 (8H, m)

MS: 338 (M+H)$^+$

REFERENCE EXAMPLE 6

A mixture of 2-naphthol (1.4 g), cesium carbonate (3.2 g) and N,N-dimethylformamide (10 mL) was stirred at 60° C. for half an hour. To the mixture was added a solution of ethyl 1-[(1R,2S)-1-({[4-chlorophenyl]sulfonyl}oxy)methyl]-2-hydroxypropyl]-1H-imidazole-4-carboxylate (0.81 g) in N,N-dimethylformamide (10 mL). The reaction mixture was stirred at 60° C. for 4 hours, cooled to ambient temperature and diluted with ethyl acetate. The precipitate was filtered off and the filtrate was succesively washed with 1 N sodium hydroxide, water and brine, dried over anhydrous sodium sulfate, and concentrated in vacuo. The residue was purified by column chromatography on silica gel (elution; 25:1 chloroform-methanol) to give the crude product, which was further purified by recrystallization from ethanol to give ethyl 1-{(1R,2S)-2-hydroxy-1-[(2-naphthyloxy)methyl]propyl}-1H-imidazole-4-carboxylate (0.13 g).

The mother liquor and the mixed fractions were combined and purified by column chromatography on silica gel (gradient elution; 50:1 to 25:1 chloroform-methanol) to give the additional product (0.14 g).

mp: 191–192° C.

NMR (DMSO-d$_6$); 1.00 (3H, d, J=6 Hz), 1.25 (3H, t, J=7 Hz), 4.0–4.1 (1H, m), 4.20 (2H, q, J=7 Hz), 4.4–4.7 (3H, m), 5.39 (1H, d, J=5 Hz), 7.0–7.2 (1H, m), 7.3–7.5 (3H, m), 7.7–7.9 (3H, m), 7.91 (1H, d, J=1 Hz), 8.08 (1H, d, J=1 Hz)

REFERENCE EXAMPLE 7

A mixture of ethyl 1-{(1R,2S)-2-hydroxy-1-[(2-naphthyloxy)methyl]propyl}-1H-imidazole-4-carboxylate (0.25 g), 28% ammonium hydroxide (14 mL) and 1,2-dimethoxyethane (7 mL) was heated at 100° C. in the stainless steel bottle for 24 hours. After cooling, the reaction mixture was concentrated in vacuo and the residue was purified by column chromatography on silica gel (gradient elution; 20:1 to 10:1 chloroform-methanol) to give the product, which was recrystallized from 5:1 ethyl acetate-ethanol (6 mL) to give ethyl 1-{(1R,2S)-2-hydroxy-1-[(2-naphthyloxy)methyl]propyl}-1H-imidazole-4-carboxamide (0.12 g).

mp: 162–164° C.

APCIMS: 326 (M+H)

IR (KBr): 3318, 1666 cm$^{-1}$

NMR (DMSO-d$_6$); 1.00 (3H, d, J=6 Hz), 3.9–4.2 (1H, m), 4.4–4.7 (3H, m), 5.38 (1H, d, J=5 Hz), 7.0–7.2 (1H, m), 7.06 (1H, br, s), 7.2–7.5 (4H, m), 7.28 (1H, br, s), 7.7–7.9 (4H, m)

Preparation 37

To a mixture of ethyl 1-[(1R,2S)-1-({[4-chlorophenyl]sulfonyl)}oxy)methyl]-2-hydroxypropyl]-1H-imidazole-4-carboxylate (0.32 g), 2-naphthalenethiol (0.19 g) and N,N-dimethylformamide (5 mL) was added cesium carbonate (0.38 g) and the reaction mixture was stirred at ambient temperature overnight. The mixture was partitioned between ethyl acetate and water. The organic layer was separated, washed with brine, dry over Na$_2$SO$_4$, and concentrated in vacuo. The residue was purified by column chromatography on silica gel (elution; 25:1 chloroform-methanol) to give the product, which was triturated with 1:1 n-hexane-ethyl acetate (10 mL) to give ethyl 1-{(1R,2S)-2-hydroxy-1-[(2-naphthylthio)methyl]propyl}-1H-imidazole-4-carboxylate (0.19 g).

mp: 117–120° C.

NMR (DMSO-d$_6$); 0.92 (3H, d, J=6 Hz), 1.24 (3H, t, J=7 Hz), 3.5–4.1 (3H, m), 4.1–4.3 (1H, m), 4.17 (2H, q, J=7 Hz), 5.35 (1H, d, J=5 Hz), 7.3–7.6 (3H, m), 7.7–7.9 (5H, m), 7.98 (1H, s)

EXAMPLE 102

A mixture of ethyl 1-{(1R,2S)-2-hydroxy-1-[(2-naphthylthio)methyl]propyl}-1H-imidazole-4-carboxylate (0.18 g), 28% ammonium hydroxide (20 mL) and 1,2-dimethoxyethane (10 mL) was heated at 100° C. in the stainless steel bottle for 24 hours. After cooling, the reaction mixture was concentrated in vacuo and the residue was purified by column chromatography on silica gel (elution; 10:1 chloroform-1% ammonium hydroxide/methanol) to give the product, which was recrystallized from 3:7 n-hexane-ethyl acetate (10 mL) to give 1-{(1R,2S)-2-hydroxy-1-[(2-naphthylthio)methyl]propyl}-1H-imidazole-4-carboxamide (102) (90 mg).

mp: >108° C. (dec.)

APCIMS: 342 (M+H)

NMR (DMSO-d$_6$); 0.92 (3H, d, J=6 Hz), 3.4–4.2 (4H, m), 5.34 (1H, d, J=5 Hz), 7.05 (1H, br, s), 7.26 (1H, br, s), 7.4–7.6 (3H, m), 7.71 (1H, s), 7.7–7.9 (5H, m)

Preparation 38

A mixture of ethyl 1-[(1R,2S)-1-({[4-chlorophenyl]sulfonyl}oxy)methyl)-2-hydroxypropyl]-1H-imidazole-4-carboxylate (0.25 g), 1-naphthalenethiol (0.14 g), cesium carbonate (0.30 g) and N,N-dimethylformamide (5 mL) was stirred at ambient temperature for 1.5 hours. The mixture was partitioned between ethyl acetate and water. The organic layer was separated, washed with brine, dried over Na$_2$SO$_4$, and concentrated in vacuo. The residue was purified by column chromatography on silica gel (gradient elution; 50:1 to 25:1 chloroform-methanol) to give the product, which was triturated with 10:1 diisopropyl ether-ethanol (11 mL) to give ethyl 1-{(1R,2S)-2-hydroxy-1-[(1-naphthylthio)methyl]propyl}-1H-imidazole-4-carboxylate (0.19 g).

mp: 110–115° C.

NMR (DMSO-d$_6$); 0.87 (3H, d, J=6 Hz), 1.26 (3H, t, J=7 Hz), 3.5–4.0 (3H, m), 4.0–4.3 (1H, m), 4.20 (2H, q, J=7 Hz), 5.31 (1H, d, J=5 Hz), 7.4–7.6 (4H, m), 7.78 (1H, s), 7.8–7.9 (1H, m), 7.9–8.2 (2H, m), 7.97 (1H, d, J=1 Hz)

EXAMPLE 103

A mixture of ethyl 1-{(1R,2S)-2-hydroxy-1-[(1-naphth-ylthio)methyl]propyl}-1H-imidazole-4-carboxylate (0.18 g), 28% ammonium hydroxide (5 mL) and 1,2-dimethoxyethane (10 mL) was heated at 100° C. in the stainless steel bottle for 24 hours. After cooling, the reaction mixture was concentrated in vacuo and the residue was purified by column chromatography on silica gel (gradient elution; 15:1 to 10:1 chloroform-methanol) to give 1-[(2R,3S)-1-(1-naphthylthio)-3-hydroxy-2-butyl]imidazol-4-carboxamide. The product was dissolved in MeOH (5 mL) and treated with a solution of 4 N hydrogen chloride in ethyl acetate (1 mL). The mixture was concentrated in vacuo and the residue was recrystallized from 5:1 ethyl acetate-methanol (6 mL) to give 1-{(1R,2S)-2-hydroxy-1-[(1-naphthylthio)methyl]propyl}-1H-imidazole-4-carboxamide hydrochloride (103) (0.11 g).

mp: >168° C. (dec.)

MS: 342 (M (free)+H), 364 (M (free)+Na)

NMR (DMSO-$d_6$); 1.00 (3H, d, J=6 Hz), 3.3–4.0 (2H, m), 4.0–4.1 (1H, m), 4.3–4.5 (1H, m), 4.8–6.6 (1H, br m), 7.4–7.7 (5H, m), 7.82 (1H, br, s), 7.8–8.2 (3H, m), 8.20 (1H, br, s), 8.29 (1H, d, J=1 Hz), 9.09 (1H, s)

Preparation 39

A mixture of ethyl 1-[(1R,2S)-1-({[4-chlorophenyl]sulfonyl}oxy)methyl]-2-hydroxypropyl]-1H-imidazole-4-carboxylate (0.30 g), 2,3-dichlorobenzenethiol (0.19 g), cesium carbonate (0.36 g) and N,N-dimethylformamide (5 mL) was stirred at ambient temperature for 2 hours. The mixture was partitioned between ethyl acetate and water. The organic layer was separated, washed with brine, dried over $Na_2SO_4$, and concentrated in vacuo. The residue was purified by column chromatography on silica gel (gradient elution; 50:1 to 25:1 chloroform-methanol) to give the product, which was triturated with 1:1 diisopropyl ether-ethyl acetate (10 mL) to give ethyl 1-{(1R,2S)-1-{[(2,3-dichlorophenyl)thio]methyl}-2-hydroxypropyl}-1H-imidazole-4-carboxylate (0.18 g).

mp: 141–143° C.

NMR (DMSO-$d_6$); 0.92 (3H, d, J=6 Hz), 1.26 (3H, t, J=7 Hz), 3.5–4.3 (4H, m), 4.20 (2H, q, J=7 Hz), 5.43 (1H, d, J=5 Hz), 7.3–7.5 (3H, m), 7.81 (1H, s), 8.01 (1H, d, J=1 Hz)

EXAMPLE 104

A mixture of ethyl 1-{(1R,2S)-1-{[(2,3-dichlorophenyl)thio]methyl}-2-hydroxypropyl}-1H-imidazole-4-carboxylate (0.17 g), 28% ammonium hydroxide (10 mL) and 1,2-dimethoxyethane (20 mL) was heated at 100° C. in the stainless steel bottle for 24 hours. After cooling, the reaction mixture was concentrated in vacuo and the residue was purified by column chromatography on silica gel (elution; 10:1 chloroform-1% ammonium hydroxide/methanol) to give the product, which was recrystallized from 1:1 n-hexane-ethyl acetate (10 mL) to give 1-{(1R,2S)-1-{[(2,3-dichlorophenyl)thio]methyl}-2-hydroxypropyl}-1H-imidazole-4-carboxamide (104) (0.10 g).

mp: >120° C. (dec.)

APCIMS: 359, 361 (M+H)

IR (KBr): 3322, 1662 $cm^{-1}$

NMR (DMSO-$d_6$); 0.92 (3H, d, J=6 Hz), 3.4–4.2 (4H, m), 5.42 (1H, d, J=5 Hz), 7.06 (1H, br, s), 7.27 (1H, br, s), 7.3–7.5 (3H, m), 7.74 (1H, s), 7.80 (1H, s)

INDUSTRIAL APPLICABILITY

Novel imidazole compounds having pharmaceutical activity such as ADA inhibiting activity are provided. These compounds are useful in immunomodulation, especially immunosuppression, antiinflammation and treatment and prevention of various diseases for which Ado is effective. Such diseases include autoimmune diseases, inflammation, organ or tissue allo- or xeno-transplant rejection, leukemias, and diseases that arise from, or are aggravated by, insufficient blood flow through a particular organ or portion thereof. These compounds or their prodrugs or salts can be administered to patients in need of the treatment in an effective amount to elevate adenosine concentration.

The invention claimed is:

1. A compound of the formula

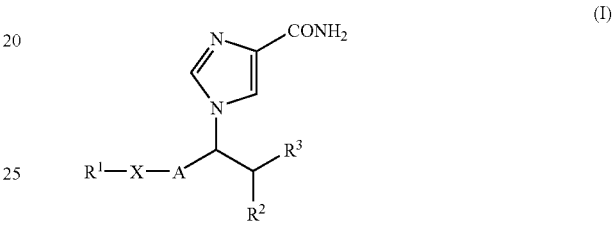

wherein $R^1$ is aryl or heterocyclic group which is optionally substituted with substituent(s);

$R^2$ is lower alkyl;

$R^3$ is hydroxy or protected hydroxy;

—A— is lower alkylene; and

—X— is —O— or —S—;

provided that when —X— is —O—, then $R^1$ is aryl which is substituted with substituent(s), or heterocyclic group which is optionally substituted with substituent(s), or a salt thereof.

2. The compound according to claim 1, wherein $R^1$ is (1) aryl optionally substituted with substituent(s) selected from the group consisting of lower alkyl, halogen, optionally substituted aryl, optionally substituted heterocyclic group, lower alkoxy, and cyano, (2) condensed heterocyclic group optionally substituted with substituent(s) selected from the group consisting of lower alkyl, optionally substituted aryl, and aryl(lower)alkyl, or (3) unsaturated heteromonocyclic group containing 1 to 4 nitrogen atoms which is optionally substituted with optionally substituted aryl.

3. The compound according to claim 2, wherein the substituent(s) of optionally substituted aryl and optionally substituted heterocyclic group are selected from the group consisting of lower alkyl, halo(lower)alkyl, lower alkoxy, halogen, aryl, aryl(lower)alkyl, and cyano.

4. The compound according to claim 1, wherein -A- is methylene or ethylene.

5. The compound according to claim 1, wherein $R^2$ is methyl.

6. The compound according to claim 1, which is a compound selected from the group consisting of:

(1) 1-[(2S,3R)-2-benzyloxy-5-(6-quinolyloxy)-3-pentyl]imidazole-4-carboxamide;

(2) 1-[(2S,3R)-2-hydroxy-5-(6-quinolyloxy)-3-pentyl]imidazole-4-carboxamide;

(3) 1-[(2S,3R)-2-benzyloxy-5-(3,4-dichlorophenoxy)-3-pentyl]imidazole-4-carboxamide;

(4) 1-[(2S,3R)-5-(3,4-dichlorophenoxy)-2-hydroxy-3-pentyl]imidazole-4-carboxamide;

(5) 1-[(2S,3R)-2-benzyloxy-5-(2-dibenzofuranyloxy)-3-pentyl]imidazole-4-carboxamide;
(6) 1-[(2S,3R)-5-(2-dibenzofuranyloxy)-2-hydroxy-3-pentyl]imidazole-4-carboxamide;
(7) 1-[(2S,3R)-2-benzyloxy-5-(2-methyl-5-benzothiazolyloxy)-3-pentyl]imidazole-4-carboxamide;
(8) 1-[(2S,3R)-2-hydroxy-5-(2-methyl-5-benzothiazolyloxy)-3-pentyl]imidazole-4-carboxamide;
(9) 1-[(2S,3R)-2-benzyloxy-5-(2-fluorenyloxy)-3-pentyl]imidazole-4-carboxamide;
(10) 1-[(2S,3R)-5-(2-fluorenyloxy)-2-hydroxy-3-pentyl]imidazole-4-carboxamide;
(11) 1-[(2S,3R)-2-benzyloxy-5-(2,3-dichlorophenoxy)-3-pentyl]imidazole-4-carboxamide;
(12) 1-[(2S,3R)-5-(2.3-dichlorophenoxy)-2-hydroxy-3-pentyl]imidazole-4-carboxamide;
(13) 1-[(2S,3R)-2-benzyloxy-5-(7-isoquinolyloxy)-3-pentyl]imidazole-4-carboxamide;
(14) 1-[(2S,3R)-2-hydroxy-5-(7-isoquinolyloxy)-3-pentyl]imidazole-4-carboxamide;
(15) 1-[(2S,3R)-5-(6-bromo-2-naphthyloxy)-2-(tert-butyldimethylsilyloxy)-3-pentyl]imidazole-4-carboxamide;
(16) 1-[(2S,3R)-5-(6-bromo-2-naphthyloxy)-2-hydroxy-3-pentyl]imidazole-4-carboxamide;
(17) 1-[(2S,3R)-2-(tert-butyldimethylsilyloxy)-5-(3,4-dimethylphenoxy)-3-pentyl]imidazole-4-carboxamide;
(18) 1-[(2S,3R)-5-(3,4-dimethylphenoxy)-2-hydroxy-3-pentyl]imidazole-4-carboxamide;
(19) 1-[(2S,3R)-5-(1,1'-biphenyl-3-yloxy)-2-(tert-butyldimethylsilyloxy)-3-pentyl]imidazole-4-carboxamide (19);
(20) 1-[(2S,3R)-5-(1,1'-biphenyl-3-yloxy)-2-hydroxy-3-pentyl]imidazole-4-carboxamide;
(21) 1-[(2S,3R)-5-(1,1'-biphenyl-2-yloxy)-2-(tert-butyldimethylsilyloxy)-3-pentyl]imidazole-4-carboxamide;
(22) 1-[(2S,3R)-5-(1,1'-biphenyl-2-yloxy)-2-hydroxy-3-pentyl]imidazole-4-carboxamide;
(23) 1-[(2S,3R)-2-(tert-butyldimethylsilyloxy)-5-(3-isoquinolyloxy)-3-pentyl]imidazole-4-carboxamide;
(24) 1-[(2S,3R)-2-hydroxy-5-(3-isoquinolyloxy)-3-pentyl]imidazole-4-carboxamide;
(25) 1-{(2S,3R)-2-(tert-butyldimethylsilyloxy)-5-[1-methyl-2-(2-phenylethyl)-1H-indol-5-yloxy]-3-pentyl}imidazole-4-carboxamide;
(26) 1-{(2S,3R)-2-hydroxy-5-[1-methyl-2-(2-phenylethyl)-1H-indol-5-yloxy]-3-pentyl}imidazole-4-carboxamide;
(27) 1-[(2S,3R)-5-(1,1'-biphenyl-4-yloxy)-2-(tert-butyldimethylsilyloxy)-3-pentyl]imidazole-4-carboxamide;
(28) 1-[(2S,3R)-5-(1,1'-biphenyl-4-yloxy)-2-hydroxy-3-pentyl]imidazole-4-carboxamide;
(29) 1-[(2S,3R)-2-(tert-butyldimethylsilyloxy)-5-(3-tert-butylphenoxy)-3-pentyl]imidazole-4-carboxamide;
(30) 1-[(2S,3R)-5-(3-tert-butylphenoxy)-2-hydroxy-3-pentyl]imidazole-4-carboxamide;
(31) 1-{(2S,3R)-2-(tert-butyldimethylsilyloxy)-5-[3-(2-thienyl)phenoxy]-3-pentyl}imidazole-4-carboxamide;
(32) 1-{(2S,3R)-2-hydroxy-5-[3-(2-thienyl)phenoxy]-3-pentyl}imidazole-4-carboxamide;
(33) 1-{(2S,3R)-2-(tert-butyldimethylsilyloxy)-5-[2-(2-thienyl)phenoxy]-3-pentyl}imidazole-4-carboxamide;
(34) 1-{(2S,3R)-2-hydroxy-5-[2-(2-thienyl)phenoxy]-3-pentyl}imidazole-4-carboxamide;
(35) 1-{(2S,3R)-5-[3-(2-benzylthiazol-4-yl)phenoxy]-2-(tert-butyldimethylsilyloxy)-3-pentyl}imidazole-4-carboxamide;
(36) 1-{(2S,3R)-5-[3-(2-benzylthiazol-4-yl)phenoxy]-2-hydroxy-3-pentyl}imidazole-4-carboxamide;
(37) 1-{(2S,3R)-2-(tert-butyldimethylsilyloxy)-5-[3-(2-phenylthiazol-4-yl)phenoxy]-3-pentyl}imidazole-4-carboxamide;
(38) 1-{(2S,3R)-2-hydroxy-5-[3-(2-phenylthiazol-4-yl)phenoxy]3-pentyl}imidazole-4-carboxamide;
(39) 1-[(2S,3R)-5-(3-bromophenoxy)-2-(tert-butyldimethylsilyloxy)-3-pentyl]imidazole-4-carboxamide;
(40) 1-[(2S,3R)-5-(3-bromophenoxy)-2-hydroxy-3-pentyl]imidazole-4-carboxamide;
(41) 1-{(2S,3R)-5-[3-(2-benzo[b]thiophenyl)phenoxy]-2-hydroxy-3-pentyl}imidazole-4-carboxamide;
(42) 1-{(2S,3R)-2-(tert-butyldimethylsilyloxy)-5-[3-(4-morpholinyl)phenoxy]-3-pentyl}imidazole-4-carboxamide;
(43) 1-{(2S,3R)-2-hydroxy-5-[3-(4-morpholinyl)phenoxy]-3-pentyl}imidazole-4-carboxamide;
(44) 1-{(2S,3R)-2-(tert-butyldimethylsilyloxy)-5-[3-(5-chloro-2-thienyl)phenoxy]-3-pentyl}imidazole-4-carboxamide;
(45) 1-{(2 S,3R)-5-[3-(5-chloro-2-thienyl)phenoxy]-2-hydroxy-3-pentyl}imidazole-4-carboxamide;
(46) 1-{(2S,3R)-2-(tert-butyldimethylsilyloxy)-5-[3-(5-methyl-2-thienyl)phenoxy]-3-pentyl}imidazole-4-carboxamide;
(47) 1-{(2S,3R)-2-hydroxy-5-[3-(5-methyl-2-thienyl)phenoxy]-3-pentyl}imidazole-4-carboxamide;
(48) 1-[(2S,3R)-2-(tert-butyldimethylsilyloxy)-5-(2-quinolyloxy)-3-pentyl]imidazole-4-carboxamide;
(49) 1-[(2S,3R)-2-hydroxy-5-(2-quinolyloxy)-3-pentyl]imidazole-4-carboxamide;
(50) 1-{(2S,3R)-5-[3-(2-benzoxazolyl)phenoxy]-2-(tert-butyldimethylsilyloxy)-3-pentyl}imidazole-4-carboxamide;
(51) 1-{(2S,3R)-5-[3-(2-benzoxazolyl)phenoxy]-2-hydroxy-3-pentyl}imidazole-4-carboxamide;
(52) 1-{(2S,3R)-5-[3-(2-benzofuranyl)phenoxy]-2-(tert-butyldimethylsilyloxy)-3-pentyl}imidazole-4-carboxamide;
(53) 1-{(2 S,3R)-5-[3-(2-benzofuranyl)phenoxy]-2-hydroxy-3-pentyl}imidazole-4-carboxamide;
(54) 1-{2S,3R}-5-[3-(1H-benzimidazol-2-yl)phenoxy]-2-(tert-butyldimethylsilyloxy)-3-pentyl}imidazole-4-carboxamide;
(55) 1-{(2S,3R)-5-[3-(1 H-benzimidazol-2-yl)phenoxy]-2-hydroxy-3-pentyl}imidazole-4-carboxamide;
(56) 1-{(2S,3R)-2-(tert-butyldimethylsilyloxy)-5-[(4'-chloro-1,1'-biphenyl-3-yl)oxy]-3-pentyl}imidazole-4-carboxamide;
(57) 1-{(2S,3R)-5-[(4'-chloro-1,1'-biphenyl-3-yl)oxy]-2-hydroxy-3-pentyl}imidazole-4-carboxamide;
(58) 1-{(2S,3R)-2-(tert-butyldimethylsilyloxy)-5-[(3'-chloro-1,1'-biphenyl-3-yl)oxy]-3-pentyl}imidazole-4-carboxamide;
(59) 1-{(2S,3R)-5-[(3'-chloro-1,1'-biphenyl-3-yl)oxy]-2-hydroxy-3-pentyl}imidazole-4-carboxamide;
(60) 1-{(2S,3R)-2-(tert-butyldimethylsilyloxy)-5-[(2'-chloro-1,1'-biphenyl-3-yl)oxy]-3-pentyl}imidazole-4-carboxamide;
(61) 1-{(2S,3R)-5-[(2'-chloro-1,1'-biphenyl-3-yl)oxy]-2-hydroxy-3-pentyl}imidazole-4-carboxamide;

(62) 1-{(2S,3R)-2-(tert-butyldimethylsilyloxy)-5-[(4'-methoxy-1,1'-biphenyl-3-yl)oxy]-3-pentyl}imidazole-4-carboxamide;
(63) 1-{(2S,3R)-2-hydroxy-5-[(4'-methoxy-1,1'-biphenyl-3-yl)oxy]-3-pentyl}imidazole-4-carboxamide;
(64) 1-{(2S,3R)-2-(tert-butyldimethylsilyloxy)-5-[(3'-methoxy-1,1'-biphenyl-3-yl)oxy]-3-pentyl}imidazole-4-carboxamide;
(65) 1-{(2S,3R)-2-hydroxy-5-[(3'-methoxy-1,1'-biphenyl-3-yl)oxy]-3-pentyl}imidazole-4-carboxamide;
(66) 1-{(2S,3R)-2-(tert-butyldimethylsilyloxy)-5-[3-(2-methoxy-5-pyridyl)phenoxy]-3-pentyl}imidazole-4-carboxamide;
(67) 1-{(2S,3R)-2-hydroxy-5-[3-(6-methoxy-3-pyridyl)phenoxy]-3-pentyl}imidazole-4-carboxamide;
(68) 1-{(2S,3R)-2-(tert-butyldimethylsilyloxy)-5-[(6-phenyl-2-pyridyl)oxy]-3-pentyl}imidazole-4-carboxamide;
(69) 1-{(2S,3R)-2-hydroxy-5-[(6-phenyl-2-pyridyl)oxy]-3-pentyl}imidazole-4-carboxamide;
(70) 1-{(2S,3R)-2-(tert-butyldimethylsilyloxy)-5-[(4'-fluoro-1,1'-biphenyl-3-yl)oxy]-3-pentyl}imidazole-4-carboxamide;
(71) 1-{(2S,3R)-5-[(4'-fluoro-1,1'-biphenyl-3-yl)oxy]-2-hydroxy-3-pentyl}imidazole-4-carboxamide;
(72) 1-[(2S,3R)-2-(tert-butyldimethylsilyloxy)-5-{[4'-(trifluoromethyl)-1,1'-biphenyl-3-yl]oxy}-3-pentyl]imidazole-4-carboxamide;
(73) 1-[(2S,3R)-2-hydroxy-5-{[4'-(trifluoromethyl)-1,1'-biphenyl-3-yl]oxy}-3-pentyl]imidazole-4-carboxamide;
(74) 1-{(2S,3R)-2-hydroxy-5-[3-(1H-pyrrol-1-yl)-2-naphthyloxy]-3-pentyl}imidazole-4-carboxamide;
(75) 1-[(2S,3R)-2-hydroxy-5-(1-methyl-1H-indol-5-yl)oxy-3-pentyl]imidazole-4-carboxamide;
(76) 1-[(2S,3R)-2-hydroxy-5-(2-naphthylthio)-3-pentyl]imidazole-4-carboxamide;
(77) 1-[(2S,3R)-2-hydroxy-5-(1-naphthylthio)-3-pentyl]imidazole-4-carboxamide;
(78) 1-[(2S,3R)-2-hydroxy-5-(2-quinolylthio)-3-pentyl]imidazole-4-carboxamide;
(79) 1-[(2S,3R)-5-(3,4-dichlorophenylthio)-2-hydroxy-3-pentyl]imidazole-4-carboxamide;
(80) 1-[(2S,3R)-5-(3,4-dimethylphenylthio)-2-hydroxy-3-pentyl]imidazole-4-carboxamide;
(81) 1-{(1R,2S)-1-[(3,4-dichlorophenoxy)methyl]-2-hydroxypropyl}-1H-imidazole-4-carboxamide;
(82) 1-{(2S,3R)-2-(tert-butyldimethylsilyloxy)-5-[(4'-cyano-1,1'-biphenyl-3-yl)oxy]-3-pentyl }imidazole-4-carboxamide;
(83) 1-{(2S,3R)-5-[(4'-cyano-1,1'-biphenyl-3-yl)oxy]-2-hydroxy-3-pentyl}imidazole-4-carboxamide;
(84) 1-{(2S,3R)-2-(tert-butyldimethylsilyloxy)-5-[(4'-methyl-1,1'-biphenyl-3-yl)oxy]-3-pentyl}imidazole-4-carboxamide;
(85) 1-{(2S,3R)-2-hydroxy-5-[(4'-methyl-1,1'-biphenyl-3-yl)oxy]-3-pentyl}imidazole-4-carboxamide;
(86) 1-{(2S,3R)-2-(tert-butyldimethylsilyloxy)-5-[3-(6-chloro-3-pyridyl)phenoxy]-3-pentyl}imidazole-4-carboxamide;
(87) 1-{(2S,3R)-5-[3-(6-chloro-3-pyridyl)phenoxy]-2-hydroxy-3-pentyl}imidazole-4-carboxamide;
(88) 1-((2S,3R)-2-(tert-butyldimethylsilyloxy)-5-{[6-(4-chlorophenyl)-2-pyridyl]oxy}-3-pentyl)imidazole-4-carboxamide;
(89) 1-((2S,3R)-2-hydroxy-5-{[6-(4-chlorophenyl)-2-pyridyl]oxy}-3-pentyl)imidazole-4-carboxamide;
(90) 1-{(2S,3R)-2-(tert-butyldimethylsilyloxy)-5-[(3',5'-dichloro-1,1'-biphenyl-3-yl)oxy]-3-pentyl}imidazole-4-carboxamide;
(91) 1-{(2S,3R)-5-[(3',5'-dichloro-1,1'-biphenyl-3-yl)oxy]-2-hydroxy-3-pentyl}imidazole-4-carboxamide;
(92) 1-[(2S,3R)-2-(tert-butyldimethylsilyloxy)-5-(7-methoxy-2-naphthyloxy)-3-pentyl]imidazole-4-carboxamide;
(93) 1-[(2S,3R)-2-hydroxy-5-(7-methoxy-2-naphthyloxy)-3-pentyl]imidazole-4-carboxamide;
(94) 1-[(2S,3R)-5-(7-bromo-2-naphthyloxy)-2-(tert-butyldimethylsilyloxy)-3-pentyl]imidazole-4-carboxamide;
(95) 1-[(2S,3R)-5-(7-bromo-2-naphthyloxy)-2-hydroxy-3-pentyl]imidazole-4-carboxamide;
(96) 1-[(2S,3R)-2-(tert-butyldimethylsilyloxy)-5-(7-chloro-2-naphthyloxy)-3-pentyl]imidazole-4-carboxamide;
(97) 1-[(2S,3R)-5-(7-chloro-2-naphthyloxy)-2-hydroxy-3-pentyl]imidazole-4-carboxamide;
(98) 1-[(2S,3R)-2-(tert-butyldimethylsilyloxy)-5-(7-cyano-2-naphthyloxy)-3-pentyl]imidazole-4-carboxamide;
(99) 1-[(2S,3R)-5-(7-cyano-2-naphthyloxy)-2-hydroxy-3-pentyl]imidazole-4-carboxamide;
(100) 1-((2S,3R)-2-(tert-butyldimethylsilyloxy)-5-{[2-(4-chlorophenyl)-1,3-benzoxazol-6-yl]oxy}-3-pentyl)imidazole-4-carboxamide;
(101) 1-((2S,3R)-5-{[2-(4-chlorophenyl)-1,3-benzoxazol-6-yl]oxy}-2-hydroxy-3-pentyl)imidazole-4-carboxamide;
(102) 1-{(1R,2S)-2-hydroxy-1-[(2-naphthylthio)methyl]propyl}-1H-imidazole-4-carboxamide;
(103) 1-{(1R,2S)-2-hydroxy-1-[(1-naphthylthio)methyl]propyl}-1H-imidazole-4-carboxamide hydrochloride; and
(104) 1-{(1R,2S)-1-{[(2,3-dichlorophenyl)thio]methyl}-2-hydroxypropyl}-1H-imidazole-4-carboxamide.

7. The compound according to claim 1, which is a compound selected from the group consisting of:
(20) 1-[(2S,3R)-5-(1,1'-biphenyl-3-yloxy)-2-hydroxy-3-pentyl]imidazole-4-carboxamide;
(41) 1-{(2S,3R)-5-[3-(2-benzo[b]thiophenyl)phenoxy]-2-hydroxy-3-pentyl}imidazole-4-carboxamide;
(53) 1-{(2S,3R)-5-[3-(2-benzofuranyl)phenoxy]-2-hydroxy-3-pentyl}imidazole-4-carboxamide;
(57) 1-{(2S,3R)-5-[(4'-chloro-1,1'-biphenyl-3-yl)oxy]-2-hydroxy-3-pentyl}imidazole-4-carboxamide;
(59) 1-{(2S,3R)-5-[(3'-chloro-1,1'-biphenyl-3-yl)oxy]-2-hydroxy-3-pentyl}imidazole-4-carboxamide;
(63) 1-{(2S,3R)-2-hydroxy-5-[(4'-methoxy-1,1'-biphenyl-3-yl)oxy]-3-pentyl}imidazole-4-carboxamide;
(85) 1-{(2S,3R)-2-hydroxy-5-[(4'-methyl-1,1'-biphenyl-3-yl)oxy]-3-pentyl}imidazole-4-carboxamide;
(89) 1-((2S,3R)-2-hydroxy-5-{[6-(4-chlorophenyl)-2-pyridyl]oxy}-3-pentyl)imidazole-4-carboxamide;
(91) 1-{(2S,3R)-5-[(3',5'-dichloro-1,1'-biphenyl-3-yl)oxy]-2-hydroxy-3-pentyl}imidazole-4-carboxamide;
(95) 1-[(2S,3R)-5-(7-bromo-2-naphthyloxy)-2-hydroxy-3-pentyl]imidazole-4-carboxamide; and
(97) 1-[(2S,3R)-5-(7-chloro-2-naphthyloxy)-2-hydroxy-3-pentyl]imidazole-4-carboxamide.

8. A pharmaceutical composition comprising the compound of claim 1 as an active ingredient and a pharmaceutically acceptable, substantially non-toxic carrier or excipient.

9. A pharmaceutical composition having an adenosine deaminase inhibiting activity, which comprises the compound of claim 1 as an active ingredient and a pharmaceutically acceptable, substantially non-toxic carrier or excipient.

10. A method for treating, inflammatory conditions, which comprises administering the compound wherein the inflammatory condition is selected from the group consisting of rheumatoid arthritis, rheumatoid spondylitis, osteoarthritis, gouty arthritis, sunburn, eczema, conjunctivitis, asthma, and bronchitis compound of claim 1 to a mammal in need of the compound.

11. A method for preparing a medicament, which comprises:
    mixing the compound of claim 1 as an active ingredient with a pharmaceutically acceptable, substantially non-toxic carrier or excipient.

12. A process for producing the compound of claim 1, the process comprising any of the following steps (1) to (3):

(1) reacting a compound of formula (II)

$R^1$—OH  (II)

wherein $R^1$ is as defined above, with a compound of formula (III)

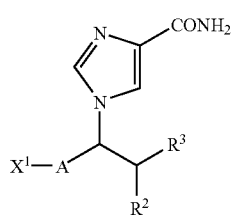
    (III)

wherein $R^2$, $R^3$, and -A- are as defined above, and $X^1$ is hydroxy or a leaving group, provided that $R^3$ is not hydroxy;

(2) reacting a compound of formula (I-1)

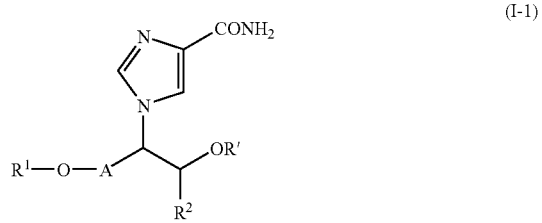
    (I-1)

wherein $R^1$, $R^2$, and -A- are as defined above, and R' is hydroxy protective group, with a deprotecting agent; or (3) reacting a compound of formula (IV)

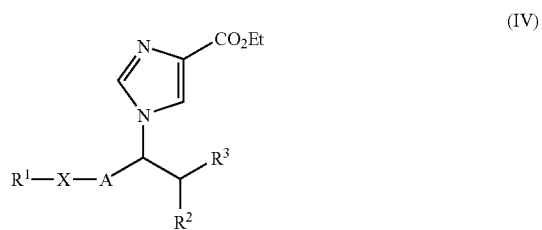
    (IV)

wherein $R^1$, $R^2$, $R^3$, -A-, and —X— are as defined above, with aqueous ammonia solution.

* * * * *

UNITED STATES PATENT AND TRADEMARK OFFICE
CERTIFICATE OF CORRECTION

| | | |
|---|---|---|
| PATENT NO. | : 7,064,144 B2 | Page 1 of 1 |
| APPLICATION NO. | : 10/483336 | |
| DATED | : June 20, 2006 | |
| INVENTOR(S) | : Tadashi Terasaka et al. | |

It is certified that error appears in the above-identified patent and that said Letters Patent is hereby corrected as shown below:

Col. 47 Claim 10 line 2, insert --of claim 1 to a mammal in need of the compound;-- after the word "compound".

Col. 47 Claim 10, line 6, delete "compound of claim 1 to a mammal in need of the" after the word "bronchitis";

Col. 47 Claim 10, line 7, delete "compound".

Signed and Sealed this

Twenty-first Day of April, 2009

JOHN DOLL
*Acting Director of the United States Patent and Trademark Office*